(12) United States Patent
Koike et al.

(10) Patent No.: US 10,808,253 B2
(45) Date of Patent: Oct. 20, 2020

(54) PEPTIDE TAG AND TAGGED PROTEIN INCLUDING SAME

(71) Applicant: IDEMITSU KOSAN CO., LTD., Chiyoda-ku (JP)

(72) Inventors: Kazuyoshi Koike, Sodegaura (JP); Eiji Takita, Sodegaura (JP); Koichi Kaneda, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 16/066,468

(22) PCT Filed: Dec. 28, 2016

(86) PCT No.: PCT/JP2016/089139
§ 371 (c)(1),
(2) Date: Jun. 27, 2018

(87) PCT Pub. No.: WO2017/115853
PCT Pub. Date: Jul. 6, 2017

(65) Prior Publication Data
US 2019/0024094 A1    Jan. 24, 2019

(30) Foreign Application Priority Data

Dec. 28, 2015  (JP) ................................ 2015-256396
Aug. 3, 2016   (JP) ................................ 2016-153265

(51) Int. Cl.
| | | |
|---|---|---|
| C07K 4/00 | (2006.01) | |
| C07K 14/00 | (2006.01) | |
| C07K 7/08 | (2006.01) | |
| C07K 7/06 | (2006.01) | |
| C12N 15/62 | (2006.01) | |
| C07K 14/565 | (2006.01) | |
| C07K 14/475 | (2006.01) | |
| C12N 15/09 | (2006.01) | |
| C07K 19/00 | (2006.01) | |
| C12N 5/10 | (2006.01) | |
| C12P 21/00 | (2006.01) | |
| C07K 14/435 | (2006.01) | |
| C12N 9/24 | (2006.01) | |
| C12P 21/02 | (2006.01) | |

(52) U.S. Cl.
CPC ................ *C12N 15/62* (2013.01); *C07K 4/00* (2013.01); *C07K 7/06* (2013.01); *C07K 7/08* (2013.01); *C07K 14/00* (2013.01); *C07K 14/43504* (2013.01); *C07K 14/475* (2013.01); *C07K 14/565* (2013.01); *C07K 19/00* (2013.01); *C12N 5/10* (2013.01); *C12N 9/248* (2013.01); *C12N 15/09* (2013.01); *C12P 21/00* (2013.01); *C12P 21/02* (2013.01); *C07K 2319/40* (2013.01); *C07K 2319/50* (2013.01); *C07K 2319/60* (2013.01); *C12Y 302/01* (2013.01)

(58) Field of Classification Search
None
See application file for complete search history.

(56) References Cited

U.S. PATENT DOCUMENTS

| | | | | |
|---|---|---|---|---|
| 6,686,333 | B1 * | 2/2004 | Kashanchi | C07K 14/005 424/93.6 |
| 2009/0137004 | A1 * | 5/2009 | Uversky | C07K 14/00 435/69.7 |
| 2011/0033389 | A1 * | 2/2011 | Chen | C07K 16/087 424/9.6 |
| 2011/0041220 | A1 | 2/2011 | Ohto et al. | |
| 2011/0231960 | A1 | 9/2011 | Sawada et al. | |
| 2014/0329742 | A1 * | 11/2014 | Dock | A61K 38/26 514/5.2 |

FOREIGN PATENT DOCUMENTS

| | | |
|---|---|---|
| JP | 2009-201437 A | 9/2009 |
| JP | 5273438 B2 | 8/2013 |
| JP | 5360727 B2 | 12/2013 |
| WO | WO 2009/133882 A1 | 11/2009 |

OTHER PUBLICATIONS

Argiolas et al., "Amino Acid Sequence of Bumblebee MCD Peptide: A New Mast Cell Degranulating Peptide From the Venom of the Bumblebee *Megabombus pennsylvanicus*", Peptides, 1985, pp. 413-436 (Year: 1985).*
GenBank: CAN98496.1; conjugal transfer protein; 2016; pp. 1-2 (Year: 2016).*
UniProtKB/Swiss-Prot: P17656.1; Cuticle collagen 2, 2006, pp. 1-2 (Year: 2006).*
UniProtKB/Swiss-Prot: Q9HX66; Probable ATP-dependent RNA helicase, 2006, p. 1 (Year: 2006).*
UniProtKB/Swiss-Prot: Q9AB24; TPR domain protein, 2006, p. 1 (Year: 2006).*
GenBank: KDB11109.1; RNA polymerase i specific transcription initiation factor of the organism [*Ustilaginoidea virens*], 2014, p. 1 (Year: 2014).*

(Continued)

*Primary Examiner* — Lianko G Garyu
(74) *Attorney, Agent, or Firm* — Oblon, McClelland, Maier & Neustadt, L.L.P.

(57) ABSTRACT

A peptide comprising the sequence shown below is added as a peptide tag to a useful protein, followed by allowing its expression.

$$X_m(PY_n)_q PZ_r$$

In this formula, X, Y, and Z each represent an amino acid residue independently selected from the group consisting of R, G, S, K, T, L, N, Q, and H, with the proviso that at least one Y represents K, L, N, Q, H, or R. m represents an integer of 0 to 5; n represents 1, 2, or 3; q represents an integer of 1 to 10; and r represents an integer of 0 to 10.

13 Claims, 11 Drawing Sheets

Specification includes a Sequence Listing.

(56) References Cited

OTHER PUBLICATIONS

Extended European Search Report dated May 22, 2019 in Patent Application No. 16881827.6, 8 pages.
Wu, D. et al. "High-level secretory expression of metchnikowin in *Escherichia coli*" Protein Expression and Purification, vol. 91, No. 1, XP 055586621. 2013. pp. 49-53.
"Uncharacterized protein from Candida parapsilosis" Database UniProt, https://www.uniprot.org/uniprot/G8B5T8.txt, XP002791092, 2012, 2 Pages.
International Search Report dated Apr. 4, 2017 in PCT/JP2016/089139, 2 pages.
International Preliminary Report on Patentability and Written Opinion dated Jul. 12, 2018 in PCT/JP2016/089139 (submitting English translation only),12 pages.
Nierman, W.C., et al., Accession No. Q9AB24, Definition: TPR Domain Protein, Jun. 1, 2001, Retrieved from the internet: URL: http://www.uniprot.org/uniprot/Q4AB24.txt?version=1 , 1 page.
Smith, D.B., et al., "Single-step purification of polypeptides expressed in *Escherichia coli* as fusions with glutathione S-transferase" Gene, vol. 67, 1988, pp. 31-40.
Marblestone, J.G., et al., "Comparison of SUMO fusion technology with traditional gene fusion systems: Enhanced expression and solubility with SUMO", Protein Science, vol. 15, 2006, pp. 182-189.
Guan, C.D., et al., "Vectors that facilitate the expression and purification of foreign peptides in *Escherichia coli* by fusion to maltose-binding protein", Gene, vol. 67, 1988, pp. 21-30.
Maina, C.V., et al., "An *Escherichia coli* vector to express and purify foreign proteins by fusion to and separation from maltose-binding protein", Gene, vol. 74, 1988, pp. 365-373.

* cited by examiner

SEQUENCE LISTING

```
<160> NUMBER OF SEQ ID NOS: 186

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
```

```
              115                 120                 125
Glu Asp Gly Ser Pro Arg Ile Gly Gln Ile Phe Lys Gln Thr Tyr Ser
    130                 135                 140
Lys Phe Asp Thr Asn Ser His Asn Asp Asp Ala Leu Leu Lys Asn Tyr
145                 150                 155                 160
Gly Leu Leu Tyr Cys Phe Arg Lys Asp Met Asp Lys Val Glu Thr Phe
                165                 170                 175
Leu Arg Ile Val Gln Cys Arg Ser Val Glu Gly Ser Cys Gly Phe
                180                 185                 190

<210> SEQ ID NO 2
<211> LENGTH: 165
<212> TYPE: PRT
<213> ORGANISM: Homo sapiens

<400> SEQUENCE: 2

Ser Tyr Asn Leu Leu Gly Phe Leu Gln Arg Ser Ser Asn Phe Gln Ser
1               5                   10                  15
Gln Lys Leu Leu Trp Gln Leu Asn Gly Arg Leu Glu Tyr Cys Leu Lys
                20                  25                  30
Asp Arg Met Asn Phe Asp Ile Pro Glu Glu Ile Lys Gln Leu Gln Gln
                35                  40                  45
Phe Gln Lys Glu Asp Ala Ala Leu Thr Ile Tyr Glu Met Leu Gln Asn
        50                  55                  60
Ile Phe Ala Ile Phe Arg Gln Asp Ser Ser Ser Thr Gly Trp Asn Glu
65                  70                  75                  80
Thr Ile Val Glu Asn Leu Leu Ala Asn Val Tyr His Gln Ile Asn His
                85                  90                  95
Leu Lys Thr Val Leu Glu Glu Lys Leu Glu Lys Glu Asp Phe Thr Arg
                100                 105                 110
Gly Lys Leu Met Ser Ser Leu His Leu Lys Arg Tyr Tyr Gly Arg Ile
            115                 120                 125
Leu His Tyr Leu Lys Ala Lys Glu Tyr Ser His Cys Ala Trp Thr Ile
        130                 135                 140
Val Arg Val Glu Ile Leu Arg Asn Phe Tyr Phe Ile Asn Arg Leu Thr
145                 150                 155                 160
Gly Tyr Leu Arg Asn
                165

<210> SEQ ID NO 3
<211> LENGTH: 573
<212> TYPE: DNA
<213> ORGANISM: Homo sapiens

<400> SEQUENCE: 3
ttcccaacca ttcccttatc caggcttttt gacaacgcta tgctccgcgc ccatcgtctg      60
caccagctgg cctttgacac ctaccaggag tttgaagaag cctatatccc aaaggaacag     120
aagtattcat tcctgcagaa cccccagacc tccctctgtt tctcagagtc tattccgaca     180
ccctccaaca gggaggaaac acaacagaaa tccaacctag agctgctccg catctccctg     240
ctgctcatcc agtcgtggct ggagcccgtg cagttcctca ggagtgtctt cgccaacagc     300
ctggtgtacg gcgcctctga cagcaacgtc tatgacctcc taaggaccct agaggaaggc     360
atccaaacgc tgatggggag gctggaagat ggcagccccc ggatcgggca gatcttcaag     420
cagacctaca gcaagttcga cacaaactca cacaacgatg acgcactact caagaactac     480
```

```
gggctgctct actgcttcag gaaggacatg gacaaggtcg agacattcct gcgcatcgtg    540
cagtgccgct ctgtggaggg cagctgtggc ttc                                573
```

<210> SEQ ID NO 4
<211> LENGTH: 495
<212> TYPE: DNA
<213> ORGANISM: Homo sapiens

<400> SEQUENCE: 4

```
agctacaact tgcttggatt cctacaaaga agcagcaatt ttcagtctca gaagctcctg     60
tggcaattga atgggaggct tgaatactgc ctcaaggaca ggatgaactt tgacatccct    120
gaggagatta agcagctgca gcagttccag aaggaggacg ccgcattgac catctatgag    180
atgctccaga acatctttgc tattttcaga caagattcat ctagcactgg ctggaatgag    240
actattgttg agaacctcct ggctaatgtc tatcatcaga taaaccatct gaagacagtc    300
ctggaagaaa aactggagaa agaagatttc accaggggaa aactcatgag cagtctgcac    360
ctgaaaagat attatgggag gattctgcat tacctgaagg ccaaggagta cagtcactgt    420
gcctggacca tagtcagagt ggaaatccta aggaactttt acttcattaa cagacttaca    480
ggttacctcc gaaac                                                     495
```

<210> SEQ ID NO 5
<211> LENGTH: 19
<212> TYPE: PRT
<213> ORGANISM: Saccharomyces cerevisiae

<400> SEQUENCE: 5

```
Met Leu Leu Gln Ala Phe Leu Phe Leu Leu Ala Gly Phe Ala Ala Lys
1               5                   10                  15

Ile Ser Ala
```

<210> SEQ ID NO 6
<211> LENGTH: 12
<212> TYPE: PRT
<213> ORGANISM: Artificial Sequence
<220> FEATURE:
<223> OTHER INFORMATION: HN tag

<400> SEQUENCE: 6

```
His Asn His Asn His Asn His Asn His Asn His Asn
1               5                   10
```

<210> SEQ ID NO 7
<211> LENGTH: 137
<212> TYPE: DNA
<213> ORGANISM: Artificial Sequence
<220> FEATURE:
<223> OTHER INFORMATION: SUC2SP-6xHN-cloning site

<400> SEQUENCE: 7

```
atgcttttgc aagccttcct tttcctcttg gctggtttcg ccgccaagat ttctgcccat     60
aatcataatc ataatcataa tcataatcat aatggcggcc gcgtcgacgg ccagggtggc    120
cctcgagggc gcgccaa                                                   137
```

<210> SEQ ID NO 8
<211> LENGTH: 41
<212> TYPE: DNA
<213> ORGANISM: Artificial Sequence
<220> FEATURE:
<223> OTHER INFORMATION: 6XHN-hGHF

<400> SEQUENCE: 8
ataatcataa tggcggccgc ttcccaacca ttcccttatc c                41

<210> SEQ ID NO 9
<211> LENGTH: 47
<212> TYPE: DNA
<213> ORGANISM: Artificial Sequence
<220> FEATURE:
<223> OTHER INFORMATION: hGHR-stopCYCt

<400> SEQUENCE: 9
gatgcggccc tctagattgg cgcgcctcag aagccacagc tgccctc          47

<210> SEQ ID NO 10
<211> LENGTH: 4
<212> TYPE: PRT
<213> ORGANISM: Artificial Sequence
<220> FEATURE:
<223> OTHER INFORMATION: FXa recognition sequence

<400> SEQUENCE: 10

Ile Glu Gly Arg
1

<210> SEQ ID NO 11
<211> LENGTH: 50
<212> TYPE: DNA
<213> ORGANISM: Artificial Sequence
<220> FEATURE:
<223> OTHER INFORMATION: 6XHN-RS-hGHF

<400> SEQUENCE: 11
atcataatca taatggcggc cgcagatcct tcccaaccat tcccttatcc        50

<210> SEQ ID NO 12
<211> LENGTH: 12
<212> TYPE: PRT
<213> ORGANISM: Artificial Sequence
<220> FEATURE:
<223> OTHER INFORMATION: ECM29SC

<400> SEQUENCE: 12

Arg Ser Pro Glu Ser Gly Ala Gly Ser Pro Arg Ser
1               5                   10

<210> SEQ ID NO 13
<211> LENGTH: 86
<212> TYPE: DNA
<213> ORGANISM: Artificial Sequence
<220> FEATURE:
<223> OTHER INFORMATION: 6XHN-ECM29SC-hGHF

<400> SEQUENCE: 13
atcataatca taatggcggc cgcttgggtt ctgaatctga tgattctgaa ggttctatta    60
aacaattccc aaccattccc ttatcc                                        86

<210> SEQ ID NO 14
<211> LENGTH: 14
<212> TYPE: PRT
<213> ORGANISM: Artificial Sequence
<220> FEATURE:
<223> OTHER INFORMATION: ECM29ON

<400> SEQUENCE: 14

```
Leu Gly Ser Glu Ser Asp Asp Ser Glu Gly Ser Ile Lys Gln
1               5                   10
```

<210> SEQ ID NO 15
<211> LENGTH: 80
<212> TYPE: DNA
<213> ORGANISM: Artificial Sequence
<220> FEATURE:
<223> OTHER INFORMATION: 6XHN-ECM29ON-hGHF

<400> SEQUENCE: 15

```
atcataatca taatggcggc cgcagatccc ctgaatctgg tgctggttct cctagatcct    60
tcccaaccat tcccttatcc                                                80
```

<210> SEQ ID NO 16
<211> LENGTH: 14
<212> TYPE: PRT
<213> ORGANISM: Artificial Sequence
<220> FEATURE:
<223> OTHER INFORMATION: Anjam-N

<400> SEQUENCE: 16

```
Gly Pro Gly Pro Ser Arg Gly Ser Asp Ile Lys Leu Thr Ser
1               5                   10
```

<210> SEQ ID NO 17
<211> LENGTH: 86
<212> TYPE: DNA
<213> ORGANISM: Artificial Sequence
<220> FEATURE:
<223> OTHER INFORMATION: 6XHN-Anjam-hGHF

<400> SEQUENCE: 17

```
atcataatca taatggcggc cgcggtcctg gtccttctag aggttctgat attaaattga    60
cttctttccc aaccattccc ttatcc                                         86
```

<210> SEQ ID NO 18
<211> LENGTH: 12
<212> TYPE: PRT
<213> ORGANISM: Artificial Sequence
<220> FEATURE:
<223> OTHER INFORMATION: PG12v5

<400> SEQUENCE: 18

```
Arg Trp Pro Gly Ser Gly Pro Gly Trp Pro Arg Ser
1               5                   10
```

<210> SEQ ID NO 19
<211> LENGTH: 80
<212> TYPE: DNA
<213> ORGANISM: Artificial Sequence
<220> FEATURE:
<223> OTHER INFORMATION: 6XHN-PG12v5-hGHF

<400> SEQUENCE: 19

```
atcataatca taatggcggc cgcagatggc ctggtttggg tcctggttgg cctacttcct    60
tcccaaccat tcccttatcc                                                80
```

<210> SEQ ID NO 20
<211> LENGTH: 12
<212> TYPE: PRT
<213> ORGANISM: Artificial Sequence
<220> FEATURE:
<223> OTHER INFORMATION: PG12v7

<400> SEQUENCE: 20

Pro Ser Gly Pro Ser Gly Pro Gly Ser Pro Thr Ser
1               5                   10

<210> SEQ ID NO 21
<211> LENGTH: 80
<212> TYPE: DNA
<213> ORGANISM: Artificial Sequence
<220> FEATURE:
<223> OTHER INFORMATION: 6XHN-PG12v7-hGHF

<400> SEQUENCE: 21
atcataatca taatggcggc cgcccttccg gtccttctgg tcctggttct cctacttcct      60
tcccaaccat tcccttatcc                                                  80

<210> SEQ ID NO 22
<211> LENGTH: 12
<212> TYPE: PRT
<213> ORGANISM: Artificial Sequence
<220> FEATURE:
<223> OTHER INFORMATION: PG12

<400> SEQUENCE: 22

Arg Ser Pro Gly Ser Gly Pro Gly Ser Pro Arg Ser
1               5                   10

<210> SEQ ID NO 23
<211> LENGTH: 80
<212> TYPE: DNA
<213> ORGANISM: Artificial Sequence
<220> FEATURE:
<223> OTHER INFORMATION: 6XHN-PG12-hGHF

<400> SEQUENCE: 23
atcataatca taatggcggc cgcagatccc ctggttctgg tcctggttct cctagatcct      60
tcccaaccat tcccttatcc                                                  80

<210> SEQ ID NO 24
<211> LENGTH: 78
<212> TYPE: DNA
<213> ORGANISM: Artificial Sequence
<220> FEATURE:
<223> OTHER INFORMATION: hGHR-PG12-stopCYCt

<400> SEQUENCE: 24
ggccctctag attggcgcgc ctcaggatct aggagaacca ggaccagaac cagggatct       60 gaagccacag ctgccctc                                                    78

<210> SEQ ID NO 25
<211> LENGTH: 12
<212> TYPE: PRT
<213> ORGANISM: Artificial Sequence
<220> FEATURE:
<223> OTHER INFORMATION: PX12-20

<400> SEQUENCE: 25

Arg Lys Pro Gly Lys Gly Pro Gly Lys Pro Arg Ser
1               5                   10

<210> SEQ ID NO 26
<211> LENGTH: 80
<212> TYPE: DNA
<213> ORGANISM: Artificial Sequence
<220> FEATURE:

<223> OTHER INFORMATION: 6XHN-PX12-20-hGHF

<400> SEQUENCE: 26

```
atcataatca taatggcggc cgcagaaaac ctggtaaagg tcctggtaaa cctagatcct    60
tcccaaccat tcccttatcc                                                80
```

<210> SEQ ID NO 27
<211> LENGTH: 80
<212> TYPE: DNA
<213> ORGANISM: Artificial Sequence
<220> FEATURE:
<223> OTHER INFORMATION: hGHR-PX12-20-stopCYCt

<400> SEQUENCE: 27

```
gcggccctct agattggcgc gcctcaggat ctaggtttac caggaccttt accaggtttt    60
ctgaagccac agctgccctc                                                80
```

<210> SEQ ID NO 28
<211> LENGTH: 12
<212> TYPE: PRT
<213> ORGANISM: Artificial Sequence
<220> FEATURE:
<223> OTHER INFORMATION: PX12-20v2

<400> SEQUENCE: 28

```
Arg Lys Pro Gly Lys Gly Pro Gly Lys Pro Arg Lys
1               5                   10
```

<210> SEQ ID NO 29
<211> LENGTH: 77
<212> TYPE: DNA
<213> ORGANISM: Artificial Sequence
<220> FEATURE:
<223> OTHER INFORMATION: 6XHN-PX12-20v2-hGHF

<400> SEQUENCE: 29

```
ataatcataa tggcggccgc agaaaacctg gtaaaggtcc tggtaaacct agaaaattcc    60
caaccattcc cttatcc                                                   77
```

<210> SEQ ID NO 30
<211> LENGTH: 12
<212> TYPE: PRT
<213> ORGANISM: Artificial Sequence
<220> FEATURE:
<223> OTHER INFORMATION: PX12-20v3

<400> SEQUENCE: 30

```
Arg Lys Pro Gly Lys Gly Pro Gly Lys Pro Thr Ser
1               5                   10
```

<210> SEQ ID NO 31
<211> LENGTH: 77
<212> TYPE: DNA
<213> ORGANISM: Artificial Sequence
<220> FEATURE:
<223> OTHER INFORMATION: 6XHN-PX12-20v3-hGHF

<400> SEQUENCE: 31

```
ataatcataa tggcggccgc agaaaacctg gtaaaggtcc tggtaaacct acttccttcc    60
caaccattcc cttatcc                                                   77
```

<210> SEQ ID NO 32
<211> LENGTH: 12

```
<212> TYPE: PRT
<213> ORGANISM: Artificial Sequence
<220> FEATURE:
<223> OTHER INFORMATION: PX12-20v4

<400> SEQUENCE: 32

Arg Lys Pro Gly Lys Gly Pro Gly Lys Pro Leu Ser
 1               5                  10

<210> SEQ ID NO 33
<211> LENGTH: 77
<212> TYPE: DNA
<213> ORGANISM: Artificial Sequence
<220> FEATURE:
<223> OTHER INFORMATION: 6XHN-PX12-20v4-hGHF

<400> SEQUENCE: 33
ataatcataa tggcggccgc agaaaacctg gtaaaggtcc tggtaaacct ttgtccttcc    60
caaccattcc cttatcc                                                  77

<210> SEQ ID NO 34
<211> LENGTH: 12
<212> TYPE: PRT
<213> ORGANISM: Artificial Sequence
<220> FEATURE:
<223> OTHER INFORMATION: PX12-20v5

<400> SEQUENCE: 34

Thr Lys Pro Gly Lys Gly Pro Gly Lys Pro Thr Ser
 1               5                  10

<210> SEQ ID NO 35
<211> LENGTH: 77
<212> TYPE: DNA
<213> ORGANISM: Artificial Sequence
<220> FEATURE:
<223> OTHER INFORMATION: 6XHN-PX12-20v5-hGHF

<400> SEQUENCE: 35
ataatcataa tggcggccgc actaaacctg gtaaaggtcc tggtaaacct acttccttcc    60
caaccattcc cttatcc                                                  77

<210> SEQ ID NO 36
<211> LENGTH: 12
<212> TYPE: PRT
<213> ORGANISM: Artificial Sequence
<220> FEATURE:
<223> OTHER INFORMATION: PX12-20v6

<400> SEQUENCE: 36

Lys Lys Pro Gly Lys Gly Pro Gly Lys Pro Lys Lys
 1               5                  10

<210> SEQ ID NO 37
<211> LENGTH: 77
<212> TYPE: DNA
<213> ORGANISM: Artificial Sequence
<220> FEATURE:
<223> OTHER INFORMATION: 6XHN-PX12-20v6-hGHF

<400> SEQUENCE: 37
ataatcataa tggcggccgc aaaaaacctg gtaaaggtcc tggtaaacct aaaaaattcc    60
caaccattcc cttatcc                                                  77
```

```
<210> SEQ ID NO 38
<211> LENGTH: 12
<212> TYPE: PRT
<213> ORGANISM: Artificial Sequence
<220> FEATURE:
<223> OTHER INFORMATION: PX12-20v7

<400> SEQUENCE: 38

Arg Lys Pro Lys Lys Lys Pro Lys Lys Pro Arg Ser
1               5                   10

<210> SEQ ID NO 39
<211> LENGTH: 77
<212> TYPE: DNA
<213> ORGANISM: Artificial Sequence
<220> FEATURE:
<223> OTHER INFORMATION: 6XHN-PX12-20v7-hGHF

<400> SEQUENCE: 39
ataatcataa tggcggccgc agaaaaccta aaaaaaaacc taaaaaacct agatccttcc    60
caaccattcc cttatcc                                                  77

<210> SEQ ID NO 40
<211> LENGTH: 12
<212> TYPE: PRT
<213> ORGANISM: Artificial Sequence
<220> FEATURE:
<223> OTHER INFORMATION: PX12-20v8

<400> SEQUENCE: 40

Arg Lys Pro Gly Lys Gly Pro Gly Ser Pro Arg Ser
1               5                   10

<210> SEQ ID NO 41
<211> LENGTH: 77
<212> TYPE: DNA
<213> ORGANISM: Artificial Sequence
<220> FEATURE:
<223> OTHER INFORMATION: 6XHN-PX12-20v8-hGHF

<400> SEQUENCE: 41
ataatcataa tggcggccgc agatccctg gtaaaggtcc tggtaaacct agatccttcc    60
caaccattcc cttatcc                                                  77

<210> SEQ ID NO 42
<211> LENGTH: 12
<212> TYPE: PRT
<213> ORGANISM: Artificial Sequence
<220> FEATURE:
<223> OTHER INFORMATION: PX12-20v9

<400> SEQUENCE: 42

Arg Lys Pro Gly Ser Gly Pro Gly Lys Pro Arg Ser
1               5                   10

<210> SEQ ID NO 43
<211> LENGTH: 77
<212> TYPE: DNA
<213> ORGANISM: Artificial Sequence
<220> FEATURE:
<223> OTHER INFORMATION: 6XHN-PX12-20v9-hGHF

<400> SEQUENCE: 43
ataatcataa tggcggccgc agaaaacctg gttctggtcc tggtaaacct agatccttcc    60
caaccattcc cttatcc                                                  77
```

<210> SEQ ID NO 44
<211> LENGTH: 12
<212> TYPE: PRT
<213> ORGANISM: Artificial Sequence
<220> FEATURE:
<223> OTHER INFORMATION: PX12-29

<400> SEQUENCE: 44

Arg Lys Pro Gly Lys Pro Lys Gly Lys Pro Thr Ser
1               5                   10

<210> SEQ ID NO 45
<211> LENGTH: 77
<212> TYPE: DNA
<213> ORGANISM: Artificial Sequence
<220> FEATURE:
<223> OTHER INFORMATION: 6XHN-PX12-29-hGHF

<400> SEQUENCE: 45
ataatcataa tggcggccgc agaaaacctg gtaaacctaa aggtaaacct acttccttcc      60
caaccattcc cttatcc                                                    77

<210> SEQ ID NO 46
<211> LENGTH: 12
<212> TYPE: PRT
<213> ORGANISM: Artificial Sequence
<220> FEATURE:
<223> OTHER INFORMATION: PX12-32

<400> SEQUENCE: 46

Arg Gln Pro Gly Gln Gly Pro Gly Gln Pro Arg Ser
1               5                   10

<210> SEQ ID NO 47
<211> LENGTH: 77
<212> TYPE: DNA
<213> ORGANISM: Artificial Sequence
<220> FEATURE:
<223> OTHER INFORMATION: 6XHN-PX12-32-hGHF

<400> SEQUENCE: 47
ataatcataa tggcggccgc agacaacctg gtcaaggtcc tggtcaacct agatccttcc      60
caaccattcc cttatcc                                                    77

<210> SEQ ID NO 48
<211> LENGTH: 12
<212> TYPE: PRT
<213> ORGANISM: Artificial Sequence
<220> FEATURE:
<223> OTHER INFORMATION: PX12-33

<400> SEQUENCE: 48

Arg Asn Pro Gly Asn Gly Pro Gly Asn Pro Arg Ser
1               5                   10

<210> SEQ ID NO 49
<211> LENGTH: 77
<212> TYPE: DNA
<213> ORGANISM: Artificial Sequence
<220> FEATURE:
<223> OTHER INFORMATION: 6XHN-PX12-33-hGHF

<400> SEQUENCE: 49
ataatcataa tggcggccgc agaaatcctg gtaatggtcc tggtaatcct agatccttcc      60

-continued

```
caaccattcc cttatcc                                                    77
```

<210> SEQ ID NO 50
<211> LENGTH: 12
<212> TYPE: PRT
<213> ORGANISM: Artificial Sequence
<220> FEATURE:
<223> OTHER INFORMATION: PX12-36

<400> SEQUENCE: 50

Arg Leu Pro Gly Leu Gly Pro Gly Leu Pro Arg Ser
1               5                   10

<210> SEQ ID NO 51
<211> LENGTH: 77
<212> TYPE: DNA
<213> ORGANISM: Artificial Sequence
<220> FEATURE:
<223> OTHER INFORMATION: 6XHN-PX12-36-hGHF

<400> SEQUENCE: 51

```
ataatcataa tggcggccgc agattgcctg gtttgggtcc tggtttgcct agatccttcc     60
caaccattcc cttatcc                                                    77
```

<210> SEQ ID NO 52
<211> LENGTH: 12
<212> TYPE: PRT
<213> ORGANISM: Artificial Sequence
<220> FEATURE:
<223> OTHER INFORMATION: PX12-38

<400> SEQUENCE: 52

Arg Arg Pro Gly Arg Gly Pro Gly Arg Pro Arg Ser
1               5                   10

<210> SEQ ID NO 53
<211> LENGTH: 77
<212> TYPE: DNA
<213> ORGANISM: Artificial Sequence
<220> FEATURE:
<223> OTHER INFORMATION: 6XHN-PX12-38-hGHF

<400> SEQUENCE: 53

```
ataatcataa tggcggccgc agaagacctg gtagaggtcc tggtagacct agatccttcc     60
caaccattcc cttatcc                                                    77
```

<210> SEQ ID NO 54
<211> LENGTH: 12
<212> TYPE: PRT
<213> ORGANISM: Artificial Sequence
<220> FEATURE:
<223> OTHER INFORMATION: PX12-28

<400> SEQUENCE: 54

Arg Ser Pro Lys Ser Lys Pro Lys Ser Pro Arg Ser
1               5                   10

<210> SEQ ID NO 55
<211> LENGTH: 77
<212> TYPE: DNA
<213> ORGANISM: Artificial Sequence
<220> FEATURE:
<223> OTHER INFORMATION: 6XHN-PX12-28-hGHF

<400> SEQUENCE: 55
ataatcataa tggcggccgc agatccccta aatctaaacc taaatctcct agatccttcc    60
caaccattcc cttatcc                                                    77

<210> SEQ ID NO 56
<211> LENGTH: 12
<212> TYPE: PRT
<213> ORGANISM: Artificial Sequence
<220> FEATURE:
<223> OTHER INFORMATION: PX12-39

<400> SEQUENCE: 56

Arg Ser Pro Gly Ser Gly Pro Gly Ser Pro Thr Ser
1               5                   10

<210> SEQ ID NO 57
<211> LENGTH: 77
<212> TYPE: DNA
<213> ORGANISM: Artificial Sequence
<220> FEATURE:
<223> OTHER INFORMATION: 6XHN-PX12-39-hGHF

<400> SEQUENCE: 57
ataatcataa tggcggccgc agatcccctg gttctggtcc tggttctcct acttccttcc    60
caaccattcc cttatcc                                                    77

<210> SEQ ID NO 58
<211> LENGTH: 17
<212> TYPE: PRT
<213> ORGANISM: Artificial Sequence
<220> FEATURE:
<223> OTHER INFORMATION: PX17-20

<400> SEQUENCE: 58

Arg Lys Pro Gly Lys Gly Pro Gly Lys Pro Arg Lys Pro Gly Lys Arg
1               5                   10                  15

Ser

<210> SEQ ID NO 59
<211> LENGTH: 92
<212> TYPE: DNA
<213> ORGANISM: Artificial Sequence
<220> FEATURE:
<223> OTHER INFORMATION: 6XHN-PX17-20-hGHF

<400> SEQUENCE: 59
ataatcataa tggcggccgc agaaaacctg gtaaaggtcc tggtaaacct agaaaacctg    60
gtaaaagatc cttcccaacc attcccttat cc                                   92

<210> SEQ ID NO 60
<211> LENGTH: 17
<212> TYPE: PRT
<213> ORGANISM: Artificial Sequence
<220> FEATURE:
<223> OTHER INFORMATION: PX17-20v2

<400> SEQUENCE: 60

Arg Lys Pro Gly Lys Gly Pro Gly Lys Pro Arg Ser Pro Gly Ser Arg
1               5                   10                  15

Ser

<210> SEQ ID NO 61
<211> LENGTH: 92

```
<212> TYPE: DNA
<213> ORGANISM: Artificial Sequence
<220> FEATURE:
<223> OTHER INFORMATION: 6XHN-PX17-20v2-hGHF

<400> SEQUENCE: 61
ataatcataa tggcggccgc agaaaacctg gtaaaggtcc tggtaaacct agatcccctg    60
gttctagatc cttcccaacc attcccttat cc                                 92

<210> SEQ ID NO 62
<211> LENGTH: 16
<212> TYPE: PRT
<213> ORGANISM: Artificial Sequence
<220> FEATURE:
<223> OTHER INFORMATION: PX12-20Xa

<400> SEQUENCE: 62

Arg Lys Pro Gly Lys Gly Pro Gly Lys Pro Arg Ser Ile Glu Gly Arg
1               5                   10                  15

<210> SEQ ID NO 63
<211> LENGTH: 89
<212> TYPE: DNA
<213> ORGANISM: Artificial Sequence
<220> FEATURE:
<223> OTHER INFORMATION: 6XHN-PX12-20Xa-hGHF

<400> SEQUENCE: 63
ataatcataa tggcggccgc agaaaacctg gtaaaggtcc tggtaaacct agatccattg    60
aaggtagatt cccaaccatt cccttatcc                                     89

<210> SEQ ID NO 64
<211> LENGTH: 11
<212> TYPE: PRT
<213> ORGANISM: Artificial Sequence
<220> FEATURE:
<223> OTHER INFORMATION: PK11v1

<400> SEQUENCE: 64

Arg Lys Pro Gly Lys Gly Pro Gly Lys Pro Arg
1               5                   10

<210> SEQ ID NO 65
<211> LENGTH: 74
<212> TYPE: DNA
<213> ORGANISM: Artificial Sequence
<220> FEATURE:
<223> OTHER INFORMATION: 6XHN-PK11v1-hGHF

<400> SEQUENCE: 65
ataatcataa tggcggccgc agaaaacctg gtaaaggtcc tggtaaacct agattcccaa    60
ccattccctt atcc                                                     74

<210> SEQ ID NO 66
<211> LENGTH: 11
<212> TYPE: PRT
<213> ORGANISM: Artificial Sequence
<220> FEATURE:
<223> OTHER INFORMATION: PK11v2

<400> SEQUENCE: 66

Lys Pro Gly Lys Gly Pro Gly Lys Pro Arg Ser
1               5                   10
```

<210> SEQ ID NO 67
<211> LENGTH: 74
<212> TYPE: DNA
<213> ORGANISM: Artificial Sequence
<220> FEATURE:
<223> OTHER INFORMATION: 6XHN-PK11v2-hGHF

<400> SEQUENCE: 67
ataatcataa tggcggccgc aaacctggta aaggtcctgg taaacctaga tccttcccaa    60
ccattccctt atcc                                                    74

<210> SEQ ID NO 68
<211> LENGTH: 41
<212> TYPE: DNA
<213> ORGANISM: Artificial Sequence
<220> FEATURE:
<223> OTHER INFORMATION: 6XHN-IFNBF

<400> SEQUENCE: 68
ataatcataa tggcggccgc agctacaact tgcttggatt c                       41

<210> SEQ ID NO 69
<211> LENGTH: 52
<212> TYPE: DNA
<213> ORGANISM: Artificial Sequence
<220> FEATURE:
<223> OTHER INFORMATION: IFNBR-stopCYCt

<400> SEQUENCE: 69
gatgcggccc tctagattgg cgcgcctcag tttcggaggt aacctgtaag tc           52

<210> SEQ ID NO 70
<211> LENGTH: 77
<212> TYPE: DNA
<213> ORGANISM: Artificial Sequence
<220> FEATURE:
<223> OTHER INFORMATION: 6XHN-PG12-IFNBF

<400> SEQUENCE: 70
ataatcataa tggcggccgc agatcccctg gttctggtcc tggttctcct agatccagct    60
acaacttgct tggattc                                                  77

<210> SEQ ID NO 71
<211> LENGTH: 80
<212> TYPE: DNA
<213> ORGANISM: Artificial Sequence
<220> FEATURE:
<223> OTHER INFORMATION: IFNBR-PG12-stopCYCt

<400> SEQUENCE: 71
ggccctctag attggcgcgc ctcaggatct aggagaacca ggaccagaac caggggatct    60
gtttcggagg taacctgtaa                                               80

<210> SEQ ID NO 72
<211> LENGTH: 77
<212> TYPE: DNA
<213> ORGANISM: Artificial Sequence
<220> FEATURE:
<223> OTHER INFORMATION: 6XHN-PX12-20-IFNBF

<400> SEQUENCE: 72
ataatcataa tggcggccgc agaaaacctg gtaaaggtcc tggtaaacct agatccagct    60
acaacttgct tggattc                                                  77

<210> SEQ ID NO 73
<211> LENGTH: 80
<212> TYPE: DNA
<213> ORGANISM: Artificial Sequence
<220> FEATURE:
<223> OTHER INFORMATION: IFNBR-PX12-20-stopCYCt

<400> SEQUENCE: 73
ggccctctag attggcgcgc ctcaggatct aggtttacca ggacctttac caggttttct    60
gtttcggagg taacctgtaa                                                80

<210> SEQ ID NO 74
<211> LENGTH: 47
<212> TYPE: DNA
<213> ORGANISM: Artificial Sequence
<220> FEATURE:
<223> OTHER INFORMATION: hGHR-stopT7t

<400> SEQUENCE: 74
tttgttagca gccggatcgg cgcgcctcag aagccacagc tgccctc                  47

<210> SEQ ID NO 75
<211> LENGTH: 80
<212> TYPE: DNA
<213> ORGANISM: Artificial Sequence
<220> FEATURE:
<223> OTHER INFORMATION: hGHR-PX12-20-stopT7t

<400> SEQUENCE: 75
gttagcagcc ggatcggcgc gcctcaggat ctaggtttac caggaccttt accaggtttt    60
ctgaagccac agctgccctc                                                80

<210> SEQ ID NO 76
<211> LENGTH: 52
<212> TYPE: DNA
<213> ORGANISM: Artificial Sequence
<220> FEATURE:
<223> OTHER INFORMATION: IFNBR-stopT7t

<400> SEQUENCE: 76
tttgttagca gccggatcgg cgcgcctcag tttcggaggt aacctgtaag tc            52

<210> SEQ ID NO 77
<211> LENGTH: 80
<212> TYPE: DNA
<213> ORGANISM: Artificial Sequence
<220> FEATURE:
<223> OTHER INFORMATION: IFNBR-PX12-20-stopT7t

<400> SEQUENCE: 77
tagcagccgg atcggcgcgc ctcaggatct aggtttacca ggacctttac caggttttct    60
gtttcggagg taacctgtaa                                                80

<210> SEQ ID NO 78
<211> LENGTH: 231
<212> TYPE: DNA
<213> ORGANISM: Artificial Sequence
<220> FEATURE:
<223> OTHER INFORMATION: RBS-PelBSP-6xHN-cloning site-CYCt

<400> SEQUENCE: 78
aataattttg tttaacttta agaaggagat atacatatga ataccctgct gccgaccgct    60
gctgctggtc tgctgctcct cgctgcccag ccggcgatgg cccataatca taatcataat   120

```
cataatcata atcataatgg cggccgcgtc gacggccagg gtggccctcg agggcgcgcc      180
gatccggctg ctaacaaagc ccgaaaggaa gctgagttgg ctgctgccac c               231
```

<210> SEQ ID NO 79
<211> LENGTH: 77
<212> TYPE: DNA
<213> ORGANISM: Artificial Sequence
<220> FEATURE:
<223> OTHER INFORMATION: 6XHN-PX12-62-hGHF

<400> SEQUENCE: 79

```
ataatcataa tggcggccgc agaaatccta aaaataaacc taaaaatcct agatccttcc      60
caaccattcc cttatcc                                                    77
```

<210> SEQ ID NO 80
<211> LENGTH: 80
<212> TYPE: DNA
<213> ORGANISM: Artificial Sequence
<220> FEATURE:
<223> OTHER INFORMATION: hGHR-PX12-20v7-stopT7t

<400> SEQUENCE: 80

```
gttagcagcc ggatcggcgc gcctcaggat ctaggttttt taggtttttt tttaggtttt      60
ctgaagccac agctgccctc                                                 80
```

<210> SEQ ID NO 81
<211> LENGTH: 77
<212> TYPE: DNA
<213> ORGANISM: Artificial Sequence
<220> FEATURE:
<223> OTHER INFORMATION: 6XHN-PX12-20v7-IFNBF

<400> SEQUENCE: 81

```
ataatcataa tggcggccgc agaaaaccta aaaaaaaacc taaaaaacct agatccagct      60
acaacttgct tggattc                                                    77
```

<210> SEQ ID NO 82
<211> LENGTH: 80
<212> TYPE: DNA
<213> ORGANISM: Artificial Sequence
<220> FEATURE:
<223> OTHER INFORMATION: IFNBR-PX12-20v7-stopT7t

<400> SEQUENCE: 82

```
tagcagccgg atcggcgcgc ctcaggatct aggtttttta ggttttttt taggttttct       60 gtttcggagg taacctgtaa                                                 80
```

<210> SEQ ID NO 83
<211> LENGTH: 43
<212> TYPE: DNA
<213> ORGANISM: Artificial Sequence
<220> FEATURE:
<223> OTHER INFORMATION: P22SP-hGHF

<400> SEQUENCE: 83

```
agtaccaagt tccgcattcg ctttcccaac cattcccttacc tcc                     43
```

<210> SEQ ID NO 84
<211> LENGTH: 36
<212> TYPE: DNA
<213> ORGANISM: Artificial Sequence
<220> FEATURE:

<223> OTHER INFORMATION: hGHR-stopBrevit

<400> SEQUENCE: 84
catcctgtta agctttcaga agccacagct gccctc        36

<210> SEQ ID NO 85
<211> LENGTH: 72
<212> TYPE: DNA
<213> ORGANISM: Artificial Sequence
<220> FEATURE:
<223> OTHER INFORMATION: P22SP-PX12-20-hGHF

<400> SEQUENCE: 85
agttccgcat cgctagaaa acctggtaaa ggtcctggta aacctagatc cttcccaacc        60
attcccttat cc        72

<210> SEQ ID NO 86
<211> LENGTH: 72
<212> TYPE: DNA
<213> ORGANISM: Artificial Sequence
<220> FEATURE:
<223> OTHER INFORMATION: hGHR-PX12-20-stopBrevit

<400> SEQUENCE: 86
catcctgtta agctttcagg atctaggttt accaggacct ttaccaggtt ttctgaagcc        60
acagctgccc tc        72

<210> SEQ ID NO 87
<211> LENGTH: 72
<212> TYPE: DNA
<213> ORGANISM: Artificial Sequence
<220> FEATURE:
<223> OTHER INFORMATION: P22SP-PX12-38-hGHF

<400> SEQUENCE: 87
agttccgcat cgctagaag acctggtaga ggtcctggta gacctagatc cttcccaacc        60
attcccttat cc        72

<210> SEQ ID NO 88
<211> LENGTH: 72
<212> TYPE: DNA
<213> ORGANISM: Artificial Sequence
<220> FEATURE:
<223> OTHER INFORMATION: hGHR-PX12-38-stopBrevit

<400> SEQUENCE: 88
catcctgtta agctttcagg atctaggtct accaggacct ctaccaggtc ttctgaagcc        60
acagctgccc tc        72

<210> SEQ ID NO 89
<211> LENGTH: 72
<212> TYPE: DNA
<213> ORGANISM: Artificial Sequence
<220> FEATURE:
<223> OTHER INFORMATION: P22SP-PX12-20v7-hGHF

<400> SEQUENCE: 89
agttccgcat cgctagaaa acctaaaaaa aaacctaaaa aacctagatc cttcccaacc        60
attcccttat cc        72

<210> SEQ ID NO 90
<211> LENGTH: 72

<212> TYPE: DNA
<213> ORGANISM: Artificial Sequence
<220> FEATURE:
<223> OTHER INFORMATION: hGHR-PX12-20v7-stopBrevit

<400> SEQUENCE: 90
catcctgtta agctttcagg atctaggttt tttaggtttt tttttaggtt ttctgaagcc    60
acagctgccc tc                                                        72

<210> SEQ ID NO 91
<211> LENGTH: 80
<212> TYPE: DNA
<213> ORGANISM: Artificial Sequence
<220> FEATURE:
<223> OTHER INFORMATION: hGHR-PX12-20v7-stopCYCt

<400> SEQUENCE: 91
gcggccctct agattggcgc gcctcaggat ctaggttttt taggtttttt tttaggtttt    60
ctgaagccac agctgccctc                                                80

<210> SEQ ID NO 92
<211> LENGTH: 12
<212> TYPE: PRT
<213> ORGANISM: Artificial Sequence
<220> FEATURE:
<223> OTHER INFORMATION: PX12-40

<400> SEQUENCE: 92

Arg Arg Pro Arg Arg Arg Pro Arg Arg Pro Arg Ser
1               5                   10

<210> SEQ ID NO 93
<211> LENGTH: 77
<212> TYPE: DNA
<213> ORGANISM: Artificial Sequence
<220> FEATURE:
<223> OTHER INFORMATION: 6XHN-PX12-40-hGHF

<400> SEQUENCE: 93
ataatcataa tggcggccgc agaagaccta gaagaagacc tagaagacct agatccttcc    60
caaccattcc cttatcc                                                   77

<210> SEQ ID NO 94
<211> LENGTH: 12
<212> TYPE: PRT
<213> ORGANISM: Artificial Sequence
<220> FEATURE:
<223> OTHER INFORMATION: PX12-41

<400> SEQUENCE: 94

Arg Arg Pro Lys Arg Lys Pro Lys Arg Pro Arg Ser
1               5                   10

<210> SEQ ID NO 95
<211> LENGTH: 77
<212> TYPE: DNA
<213> ORGANISM: Artificial Sequence
<220> FEATURE:
<223> OTHER INFORMATION: 6XHN-PX12-41-hGHF

<400> SEQUENCE: 95
ataatcataa tggcggccgc agaagaccta aagaaaaacc taaaagacct agatccttcc    60
caaccattcc cttatcc                                                   77

<210> SEQ ID NO 96
<211> LENGTH: 12
<212> TYPE: PRT
<213> ORGANISM: Artificial Sequence
<220> FEATURE:
<223> OTHER INFORMATION: PX12-43

<400> SEQUENCE: 96

Arg Lys Pro Arg Lys Pro Arg Lys Pro Arg Ser
1               5                   10

<210> SEQ ID NO 97
<211> LENGTH: 77
<212> TYPE: DNA
<213> ORGANISM: Artificial Sequence
<220> FEATURE:
<223> OTHER INFORMATION: 6XHN-PX12-43-hGHF

<400> SEQUENCE: 97
ataatcataa tggcggccgc agaaaaccta gaaaaagacc tagaaaacct agatccttcc      60
caaccattcc cttatcc                                                    77

<210> SEQ ID NO 98
<211> LENGTH: 12
<212> TYPE: PRT
<213> ORGANISM: Artificial Sequence
<220> FEATURE:
<223> OTHER INFORMATION: PX12-44

<400> SEQUENCE: 98

Lys Lys Pro Lys Lys Pro Lys Lys Pro Lys Lys
1               5                   10

<210> SEQ ID NO 99
<211> LENGTH: 77
<212> TYPE: DNA
<213> ORGANISM: Artificial Sequence
<220> FEATURE:
<223> OTHER INFORMATION: 6XHN-PX12-44-hGHF

<400> SEQUENCE: 99
ataatcataa tggcggccgc aaaaaaccta aaaaaaaacc taaaaaacct aaaaaattcc      60
caaccattcc cttatcc                                                    77

<210> SEQ ID NO 100
<211> LENGTH: 17
<212> TYPE: PRT
<213> ORGANISM: Artificial Sequence
<220> FEATURE:
<223> OTHER INFORMATION: PX17-20v7

<400> SEQUENCE: 100

Arg Lys Pro Lys Lys Lys Pro Lys Lys Pro Arg Lys Pro Lys Lys Arg
1               5                   10                  15

Ser

<210> SEQ ID NO 101
<211> LENGTH: 92
<212> TYPE: DNA
<213> ORGANISM: Artificial Sequence
<220> FEATURE:
<223> OTHER INFORMATION: 6XHN-PX17-20v7-hGHF

<400> SEQUENCE: 101

```
ataatcataa tggcggccgc agaaaaccta aaaaaaaacc taaaaaacct agaaaaccta    60
aaaaaagatc cttcccaacc attcccttat cc                                  92
```

<210> SEQ ID NO 102
<211> LENGTH: 17
<212> TYPE: PRT
<213> ORGANISM: Artificial Sequence
<220> FEATURE:
<223> OTHER INFORMATION: PX17-20v8

<400> SEQUENCE: 102

```
Arg Lys Pro Lys Lys Lys Pro Lys Lys Pro Lys Lys Pro Lys Lys Arg
1               5                   10                  15

Ser
```

<210> SEQ ID NO 103
<211> LENGTH: 92
<212> TYPE: DNA
<213> ORGANISM: Artificial Sequence
<220> FEATURE:
<223> OTHER INFORMATION: 6XHN-PX17-20v8-hGHF

<400> SEQUENCE: 103

```
ataatcataa tggcggccgc agaaaaccta aaaaaaaacc taaaaaacct aaaaaaccta    60
aaaaaagatc cttcccaacc attcccttat cc                                  92
```

<210> SEQ ID NO 104
<211> LENGTH: 13
<212> TYPE: PRT
<213> ORGANISM: Artificial Sequence
<220> FEATURE:
<223> OTHER INFORMATION: PX13-01

<400> SEQUENCE: 104

```
Arg Lys Pro Lys Lys Lys Pro Lys Lys Lys Pro Arg Ser
1               5                   10
```

<210> SEQ ID NO 105
<211> LENGTH: 80
<212> TYPE: DNA
<213> ORGANISM: Artificial Sequence
<220> FEATURE:
<223> OTHER INFORMATION: 6XHN-PX13-01-hGHF

<400> SEQUENCE: 105

```
ataatcataa tggcggccgc agaaaaccta aaaaaaaacc taaaaaaaaa cctagatcct    60
tcccaaccat tcccttatcc                                                80
```

<210> SEQ ID NO 106
<211> LENGTH: 12
<212> TYPE: PRT
<213> ORGANISM: Artificial Sequence
<220> FEATURE:
<223> OTHER INFORMATION: PX12-45

<400> SEQUENCE: 106

```
Arg Lys Pro Lys Lys Pro Lys Lys Pro Lys Arg Ser
1               5                   10
```

<210> SEQ ID NO 107
<211> LENGTH: 77
<212> TYPE: DNA
<213> ORGANISM: Artificial Sequence
<220> FEATURE:

<223> OTHER INFORMATION: 6XHN-PX12-45-hGHF

<400> SEQUENCE: 107
ataatcataa tggcggccgc agaaaaccta aaaaacctaa aaaacctaaa agatccttcc    60
caaccattcc cttatcc                                                  77

<210> SEQ ID NO 108
<211> LENGTH: 22
<212> TYPE: PRT
<213> ORGANISM: Artificial Sequence
<220> FEATURE:
<223> OTHER INFORMATION: PX22-20v7

<400> SEQUENCE: 108

Arg Lys Pro Lys Lys Lys Pro Lys Lys Pro Arg Lys Pro Lys Lys Lys
1               5                   10                  15

Pro Lys Lys Pro Arg Ser
            20

<210> SEQ ID NO 109
<211> LENGTH: 107
<212> TYPE: DNA
<213> ORGANISM: Artificial Sequence
<220> FEATURE:
<223> OTHER INFORMATION: 6XHN-PX22-20v7-hGHF

<400> SEQUENCE: 109
ataatcataa tggcggccgc agaaaaccta aaaaaaaacc taaaaaacct agaaaaccta    60
aaaaaaaacc taaaaaacct agatccttcc caaccattcc cttatcc                 107

<210> SEQ ID NO 110
<211> LENGTH: 32
<212> TYPE: PRT
<213> ORGANISM: Artificial Sequence
<220> FEATURE:
<223> OTHER INFORMATION: PX32-20v7

<400> SEQUENCE: 110

Arg Lys Pro Lys Lys Lys Pro Lys Lys Pro Arg Lys Pro Lys Lys Lys
1               5                   10                  15

Pro Lys Lys Pro Arg Lys Pro Lys Lys Lys Pro Lys Lys Pro Arg Ser
            20                  25                  30

<210> SEQ ID NO 111
<211> LENGTH: 137
<212> TYPE: DNA
<213> ORGANISM: Artificial Sequence
<220> FEATURE:
<223> OTHER INFORMATION: 6XHN-PX32-20v7-hGHF

<400> SEQUENCE: 111
ataatcataa tggcggccgc agaaaaccta aaaaaaaacc taaaaaacct agaaaaccta    60
aaaaaaaacc taaaaaacct agaaaaccta aaaaaaaacc taaaaaacct agatccttcc   120
caaccattcc cttatcc                                                  137

<210> SEQ ID NO 112
<211> LENGTH: 12
<212> TYPE: PRT
<213> ORGANISM: Artificial Sequence
<220> FEATURE:
<223> OTHER INFORMATION: PX12-20v9

<400> SEQUENCE: 112

Arg Lys Pro Lys Ser Lys Pro Lys Lys Pro Arg Ser
1               5                   10

<210> SEQ ID NO 113
<211> LENGTH: 77
<212> TYPE: DNA
<213> ORGANISM: Artificial Sequence
<220> FEATURE:
<223> OTHER INFORMATION: 6XHN-PX12-20v9-hGHF

<400> SEQUENCE: 113
ataatcataa tggcggccgc agaaaaccta aatctaaacc taaaaaacct agatccttcc    60
caaccattcc cttatcc                                                   77

<210> SEQ ID NO 114
<211> LENGTH: 12
<212> TYPE: PRT
<213> ORGANISM: Artificial Sequence
<220> FEATURE:
<223> OTHER INFORMATION: PX12-20v10

<400> SEQUENCE: 114

Arg Lys Pro Lys Gly Lys Pro Lys Lys Pro Arg Ser
1               5                   10

<210> SEQ ID NO 115
<211> LENGTH: 77
<212> TYPE: DNA
<213> ORGANISM: Artificial Sequence
<220> FEATURE:
<223> OTHER INFORMATION: 6XHN-PX12-20v10-hGHF

<400> SEQUENCE: 115
ataatcataa tggcggccgc agaaaaccta aggtaaaccc taaaaaacct agatccttcc    60
caaccattcc cttatcc                                                   77

<210> SEQ ID NO 116
<211> LENGTH: 12
<212> TYPE: PRT
<213> ORGANISM: Artificial Sequence
<220> FEATURE:
<223> OTHER INFORMATION: PX12-20v12

<400> SEQUENCE: 116

Arg Lys Pro Gly Lys Lys Pro Gly Lys Pro Arg Ser
1               5                   10

<210> SEQ ID NO 117
<211> LENGTH: 77
<212> TYPE: DNA
<213> ORGANISM: Artificial Sequence
<220> FEATURE:
<223> OTHER INFORMATION: 6XHN-PX12-20v12-hGHF

<400> SEQUENCE: 117
ataatcataa tggcggccgc agaaaacctg gtaaaaaacc tggtaaacct agatccttcc    60
caaccattcc cttatcc                                                   77

<210> SEQ ID NO 118
<211> LENGTH: 12
<212> TYPE: PRT
<213> ORGANISM: Artificial Sequence
<220> FEATURE:
<223> OTHER INFORMATION: PX12-20v13

<400> SEQUENCE: 118

Arg Lys Pro Gly Gly Lys Pro Gly Lys Pro Arg Ser
1               5                   10

<210> SEQ ID NO 119
<211> LENGTH: 77
<212> TYPE: DNA
<213> ORGANISM: Artificial Sequence
<220> FEATURE:
<223> OTHER INFORMATION: 6XHN-PX12-20v13-hGHF

<400> SEQUENCE: 119
ataatcataa tggcggccgc agaaaacctg gtggtaaacc tggtaaacct agatccttcc    60
caaccattcc cttatcc                                                  77

<210> SEQ ID NO 120
<211> LENGTH: 10
<212> TYPE: PRT
<213> ORGANISM: Artificial Sequence
<220> FEATURE:
<223> OTHER INFORMATION: PK10v2

<400> SEQUENCE: 120

Arg Lys Pro Lys Lys Lys Pro Arg Lys Pro
1               5                   10

<210> SEQ ID NO 121
<211> LENGTH: 71
<212> TYPE: DNA
<213> ORGANISM: Artificial Sequence
<220> FEATURE:
<223> OTHER INFORMATION: 6XHN-PK10v2-hGHF

<400> SEQUENCE: 121
ataatcataa tggcggccgc agaaaaccta aaaaaaaacc tagaaaacct ttcccaacca    60
ttcccttatc c                                                        71

<210> SEQ ID NO 122
<211> LENGTH: 9
<212> TYPE: PRT
<213> ORGANISM: Artificial Sequence
<220> FEATURE:
<223> OTHER INFORMATION: PK09v2

<400> SEQUENCE: 122

Arg Lys Pro Lys Lys Lys Pro Arg Lys
1               5

<210> SEQ ID NO 123
<211> LENGTH: 68
<212> TYPE: DNA
<213> ORGANISM: Artificial Sequence
<220> FEATURE:
<223> OTHER INFORMATION: 6XHN-PK09v2-hGHF

<400> SEQUENCE: 123
ataatcataa tggcggccgc agaaaaccta aaaaaaaacc tagaaaattc ccaaccattc    60
ccttatcc                                                            68

<210> SEQ ID NO 124
<211> LENGTH: 10
<212> TYPE: PRT
<213> ORGANISM: Artificial Sequence
<220> FEATURE:
<223> OTHER INFORMATION: PK10v3

<400> SEQUENCE: 124

Arg Pro Lys Lys Lys Pro Lys Lys Pro Arg
1               5                   10

<210> SEQ ID NO 125
<211> LENGTH: 71
<212> TYPE: DNA
<213> ORGANISM: Artificial Sequence
<220> FEATURE:
<223> OTHER INFORMATION: 6XHN-PK10v3-hGHF

<400> SEQUENCE: 125
ataatcataa tggcggccgc agacctaaaa aaaaacctaa aaaacctaga ttcccaacca      60
ttcccttatc c                                                         71

<210> SEQ ID NO 126
<211> LENGTH: 8
<212> TYPE: PRT
<213> ORGANISM: Artificial Sequence
<220> FEATURE:
<223> OTHER INFORMATION: PK08v3

<400> SEQUENCE: 126

Arg Pro Lys Arg Lys Pro Arg Lys
1               5

<210> SEQ ID NO 127
<211> LENGTH: 65
<212> TYPE: DNA
<213> ORGANISM: Artificial Sequence
<220> FEATURE:
<223> OTHER INFORMATION: 6XHN-PK08v3-hGHF

<400> SEQUENCE: 127
ataatcataa tggcggccgc agacctaaaa gaaaacctag aaaattccca accattccct      60
tatcc                                                                65

<210> SEQ ID NO 128
<211> LENGTH: 9
<212> TYPE: PRT
<213> ORGANISM: Artificial Sequence
<220> FEATURE:
<223> OTHER INFORMATION: PK09v3

<400> SEQUENCE: 128

Pro Arg Lys Pro Arg Lys Pro Arg Lys
1               5

<210> SEQ ID NO 129
<211> LENGTH: 68
<212> TYPE: DNA
<213> ORGANISM: Artificial Sequence
<220> FEATURE:
<223> OTHER INFORMATION: 6XHN-PK09v3-hGHF

<400> SEQUENCE: 129
ataatcataa tggcggccgc cctagaaaac ctagaaaacc tagaaaattc ccaaccattc      60
ccttatcc                                                             68

<210> SEQ ID NO 130
<211> LENGTH: 9

```
<212> TYPE: PRT
<213> ORGANISM: Artificial Sequence
<220> FEATURE:
<223> OTHER INFORMATION: PK09v4

<400> SEQUENCE: 130

Pro Lys Arg Pro Lys Arg Pro Lys Arg
1               5

<210> SEQ ID NO 131
<211> LENGTH: 68
<212> TYPE: DNA
<213> ORGANISM: Artificial Sequence
<220> FEATURE:
<223> OTHER INFORMATION: 6XHN-PK09v4-hGHF

<400> SEQUENCE: 131
ataatcataa tggcggccgc cctaaaagac ctaaaagacc taaaagattc ccaaccattc    60
ccttatcc                                                            68

<210> SEQ ID NO 132
<211> LENGTH: 12
<212> TYPE: PRT
<213> ORGANISM: Artificial Sequence
<220> FEATURE:
<223> OTHER INFORMATION: PX12-49

<400> SEQUENCE: 132

Arg Lys Pro Lys Leu Lys Pro Lys Lys Pro Arg Ser
1               5                   10

<210> SEQ ID NO 133
<211> LENGTH: 77
<212> TYPE: DNA
<213> ORGANISM: Artificial Sequence
<220> FEATURE:
<223> OTHER INFORMATION: 6XHN-PX12-49-hGHF

<400> SEQUENCE: 133
ataatcataa tggcggccgc agaaaaccta aattgaaacc taaaaaacct agatccttcc    60
caaccattcc cttatcc                                                  77

<210> SEQ ID NO 134
<211> LENGTH: 12
<212> TYPE: PRT
<213> ORGANISM: Artificial Sequence
<220> FEATURE:
<223> OTHER INFORMATION: PX12-51

<400> SEQUENCE: 134

Arg Arg Pro Leu Arg Leu Pro Leu Arg Pro Arg Ser
1               5                   10

<210> SEQ ID NO 135
<211> LENGTH: 77
<212> TYPE: DNA
<213> ORGANISM: Artificial Sequence
<220> FEATURE:
<223> OTHER INFORMATION: 6XHN-PX12-51-hGHF

<400> SEQUENCE: 135
ataatcataa tggcggccgc agaagacctt tgagattgcc tttgagacct agatccttcc    60
caaccattcc cttatcc                                                  77
```

```
<210> SEQ ID NO 136
<211> LENGTH: 12
<212> TYPE: PRT
<213> ORGANISM: Artificial Sequence
<220> FEATURE:
<223> OTHER INFORMATION: PX12-52

<400> SEQUENCE: 136

Arg Gln Pro Lys Gln Lys Pro Lys Gln Pro Arg Ser
1               5                   10

<210> SEQ ID NO 137
<211> LENGTH: 77
<212> TYPE: DNA
<213> ORGANISM: Artificial Sequence
<220> FEATURE:
<223> OTHER INFORMATION: 6XHN-PX12-52-hGHF

<400> SEQUENCE: 137
ataatcataa tggcggccgc agacaaccta acaaaaaacc taaacaacct agatccttcc     60
caaccattcc cttatcc                                                   77

<210> SEQ ID NO 138
<211> LENGTH: 12
<212> TYPE: PRT
<213> ORGANISM: Artificial Sequence
<220> FEATURE:
<223> OTHER INFORMATION: PX12-54

<400> SEQUENCE: 138

Arg Gln Pro Lys Lys Lys Pro Lys Gln Pro Arg Ser
1               5                   10

<210> SEQ ID NO 139
<211> LENGTH: 77
<212> TYPE: DNA
<213> ORGANISM: Artificial Sequence
<220> FEATURE:
<223> OTHER INFORMATION: 6XHN-PX12-54-hGHF

<400> SEQUENCE: 139
ataatcataa tggcggccgc agacaaccta aaaaaaaacc taaacaacct agatccttcc     60
caaccattcc cttatcc                                                   77

<210> SEQ ID NO 140
<211> LENGTH: 12
<212> TYPE: PRT
<213> ORGANISM: Artificial Sequence
<220> FEATURE:
<223> OTHER INFORMATION: PX12-61

<400> SEQUENCE: 140

Arg His Pro Lys His Lys Pro Lys His Pro Arg Ser
1               5                   10

<210> SEQ ID NO 141
<211> LENGTH: 77
<212> TYPE: DNA
<213> ORGANISM: Artificial Sequence
<220> FEATURE:
<223> OTHER INFORMATION: 6XHN-PX12-61-hGHF

<400> SEQUENCE: 141
ataatcataa tggcggccgc agacatccta acataaaacc taaacatcct agatccttcc     60
caaccattcc cttatcc                                                   77
```

<210> SEQ ID NO 142
<211> LENGTH: 12
<212> TYPE: PRT
<213> ORGANISM: Artificial Sequence
<220> FEATURE:
<223> OTHER INFORMATION: PX12-62

<400> SEQUENCE: 142

Arg Asn Pro Lys Asn Lys Pro Lys Asn Pro Arg Ser
1               5                   10

<210> SEQ ID NO 143
<211> LENGTH: 12
<212> TYPE: PRT
<213> ORGANISM: Artificial Sequence
<220> FEATURE:
<223> OTHER INFORMATION: PX12-40v2

<400> SEQUENCE: 143

Arg Arg Pro Arg Arg Pro Arg Arg Pro Arg Arg Ser
1               5                   10

<210> SEQ ID NO 144
<211> LENGTH: 77
<212> TYPE: DNA
<213> ORGANISM: Artificial Sequence
<220> FEATURE:
<223> OTHER INFORMATION: primer 6XHN-PX12-40v2-hGHF

<400> SEQUENCE: 144
ataatcataa tggcggccgc agaagaccta gaagacctag aagacctaga agatccttcc      60
caaccattcc cttatcc                                                    77

<210> SEQ ID NO 145
<211> LENGTH: 12
<212> TYPE: PRT
<213> ORGANISM: Artificial Sequence
<220> FEATURE:
<223> OTHER INFORMATION: PX12-41v2

<400> SEQUENCE: 145

Arg Arg Pro Lys Arg Pro Lys Arg Pro Lys Arg Ser
1               5                   10

<210> SEQ ID NO 146
<211> LENGTH: 77
<212> TYPE: DNA
<213> ORGANISM: Artificial Sequence
<220> FEATURE:
<223> OTHER INFORMATION: primer 6XHN-PX12-41v2-hGHF

<400> SEQUENCE: 146
ataatcataa tggcggccgc agaagaccta aaagacctaa aagacctaaa agatccttcc      60
caaccattcc cttatcc                                                    77

<210> SEQ ID NO 147
<211> LENGTH: 11
<212> TYPE: PRT
<213> ORGANISM: Artificial Sequence
<220> FEATURE:
<223> OTHER INFORMATION: PX12-45v2

<400> SEQUENCE: 147

Arg Lys Pro Lys Lys Pro Lys Lys Pro Arg Ser

<210> SEQ ID NO 148
<211> LENGTH: 74
<212> TYPE: DNA
<213> ORGANISM: Artificial Sequence
<220> FEATURE:
<223> OTHER INFORMATION: primer 6XHN-PX12-45v2-hGHF

<400> SEQUENCE: 148
ataatcataa tggcggccgc agaaaaccta aaaacctaa aaacctaga tccttcccaa    60 ccattccctt atcc                                                   74

<210> SEQ ID NO 149
<211> LENGTH: 13
<212> TYPE: PRT
<213> ORGANISM: Artificial Sequence
<220> FEATURE:
<223> OTHER INFORMATION: PX12-45v3

<400> SEQUENCE: 149

Arg Lys Pro Lys Lys Pro Lys Lys Pro Lys Lys Arg Ser
1               5                   10

<210> SEQ ID NO 150
<211> LENGTH: 80
<212> TYPE: DNA
<213> ORGANISM: Artificial Sequence
<220> FEATURE:
<223> OTHER INFORMATION: primer 6XHN-PX12-45v3-hGHF

<400> SEQUENCE: 150
ataatcataa tggcggccgc agaaaaccta aaaacctaa aaacctaaa aaaagatcct    60 tcccaaccat tcccttatcc                                             80

<210> SEQ ID NO 151
<211> LENGTH: 12
<212> TYPE: PRT
<213> ORGANISM: Artificial Sequence
<220> FEATURE:
<223> OTHER INFORMATION: PX12-75

<400> SEQUENCE: 151

Arg Lys Pro Gly Ser Lys Pro Gly Lys Pro Arg Ser
1               5                   10

<210> SEQ ID NO 152
<211> LENGTH: 77
<212> TYPE: DNA
<213> ORGANISM: Artificial Sequence
<220> FEATURE:
<223> OTHER INFORMATION: primer 6XHN-PX12-75-hGHF

<400> SEQUENCE: 152
ataatcataa tggcggccgc agaaaacctg gttctaaacc tggtaaacct agatccttcc    60
caaccattcc cttatcc                                                  77

<210> SEQ ID NO 153
<211> LENGTH: 12
<212> TYPE: PRT
<213> ORGANISM: Artificial Sequence
<220> FEATURE:
<223> OTHER INFORMATION: PX12-76

<400> SEQUENCE: 153

Arg Lys Pro Gln Gln Lys Pro Gln Lys Pro Arg Ser
1               5                   10

<210> SEQ ID NO 154
<211> LENGTH: 77
<212> TYPE: DNA
<213> ORGANISM: Artificial Sequence
<220> FEATURE:
<223> OTHER INFORMATION: primer 6XHN-PX12-76-hGHF

<400> SEQUENCE: 154
ataatcataa tggcggccgc agaaaacctc aacaaaaacc tcaaaaacct agatccttcc     60
caaccattcc cttatcc                                                   77

<210> SEQ ID NO 155
<211> LENGTH: 12
<212> TYPE: PRT
<213> ORGANISM: Artificial Sequence
<220> FEATURE:
<223> OTHER INFORMATION: PX12-77

<400> SEQUENCE: 155

Arg Arg Pro Gly Ser Arg Pro Gly Arg Pro Arg Ser
1               5                   10

<210> SEQ ID NO 156
<211> LENGTH: 77
<212> TYPE: DNA
<213> ORGANISM: Artificial Sequence
<220> FEATURE:
<223> OTHER INFORMATION: primer 6XHN-PX12-77-hGHF

<400> SEQUENCE: 156
ataatcataa tggcggccgc agaagacctg gttctagacc tggtagacct agatccttcc     60
caaccattcc cttatcc                                                   77

<210> SEQ ID NO 157
<211> LENGTH: 11
<212> TYPE: PRT
<213> ORGANISM: Artificial Sequence
<220> FEATURE:
<223> OTHER INFORMATION: PX12-78

<400> SEQUENCE: 157

Arg Lys Pro Lys Pro Lys Pro Lys Pro Arg Ser
1               5                   10

<210> SEQ ID NO 158
<211> LENGTH: 74
<212> TYPE: DNA
<213> ORGANISM: Artificial Sequence
<220> FEATURE:
<223> OTHER INFORMATION: primer 6XHN-PX12-78-hGHF

<400> SEQUENCE: 158
ataatcataa tggcggccgc agaaaaccta aacctaaacc taaacctaga tccttcccaa     60
ccattcccct tatcc                                                     74

<210> SEQ ID NO 159
<211> LENGTH: 185
<212> TYPE: PRT
<213> ORGANISM: Bacillus subtilis

<400> SEQUENCE: 159

```
Ala Ser Pro Asp Tyr Trp Gln Asn Trp Thr Asp Gly Gly Thr Val
1               5                   10                  15

Asn Ala Val Asn Gly Pro Gly Asn Tyr Ser Val Asn Trp Ser Asn
                20                  25                  30

Thr Gly Asn Phe Val Val Gly Lys Gly Trp Thr Thr Gly Ser Pro Ser
            35                  40                  45

Arg Thr Ile Asn Tyr Asn Ala Gly Val Trp Ala Pro Asn Gly Asn Gly
        50                  55                  60

Tyr Leu Ala Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Glu Lys Thr Thr Phe Thr Gln Tyr
        115                 120                 125

Trp Ser Val Arg Gln Thr Lys Arg Pro Thr Gly Ser Asn Ala Lys Ile
130                 135                 140

Thr Phe Ser Asn His Val Arg Ala Trp Lys Ser His Gly Met Asn Leu
145                 150                 155                 160

Gly Ser Ile Trp Ser Tyr Gln Val Leu Ala Thr Glu Gly Tyr Gln Ser
                165                 170                 175

Ser Gly Ser Ser Asn Val Thr Val Trp
                180                 185

<210> SEQ ID NO 160
<211> LENGTH: 555
<212> TYPE: DNA
<213> ORGANISM: Bacillus subtilis

<400> SEQUENCE: 160
gctagcccag actactggca aaattggact gatggcggcg aacagtaaa cgctgtcaat     60 gggcctggag ggaattacag tgttaattgg tctaataccg gaaatttcgt tgttggtaaa   120
ggttggacta caggttcgcc atctaggaca ataaactata tgccggagt  ttgggcgccg   180 aatggcaatg gatatttggc tttatatggt tggacgagat cacctctcat agaatattat   240
gtagtggatt catggggtac ttatagacct actggaacgt ataaaggtac tgtaaaaagt   300
gatggcggca catatgacat atatacaact acacgttata atgcaccttc cattgatggc   360
gaaaaaacta ctttcacgca gtactggagt gttcgccaga cgaagagacc aactggaagc   420
aacgctaaaa tcactttcag caatcatgtt agagcatgga agagtcatgg aatgaatctg   480
ggtagtattt ggtcttatca agtcttagcg acagagggat atcaaagtag tggaagttct   540
aacgtaacag tgtgg                                                    555

<210> SEQ ID NO 161
<211> LENGTH: 9
<212> TYPE: PRT
<213> ORGANISM: Artificial Sequence
<220> FEATURE:
<223> OTHER INFORMATION: HA

<400> SEQUENCE: 161

Tyr Pro Tyr Asp Val Pro Asp Tyr Ala
1               5
```

<210> SEQ ID NO 162
<211> LENGTH: 6
<212> TYPE: PRT
<213> ORGANISM: Artificial Sequence
<220> FEATURE:
<223> OTHER INFORMATION: 6XHis

<400> SEQUENCE: 162

His His His His His His
1               5

<210> SEQ ID NO 163
<211> LENGTH: 56
<212> TYPE: DNA
<213> ORGANISM: Artificial Sequence
<220> FEATURE:
<223> OTHER INFORMATION: primer HA-6XHis

<400> SEQUENCE: 163
ctttcgctta cccatatgat gtaccagatt acgctcatca tcatcatcat cattga        56

<210> SEQ ID NO 164
<211> LENGTH: 54
<212> TYPE: DNA
<213> ORGANISM: Artificial Sequence
<220> FEATURE:
<223> OTHER INFORMATION: primer mCWSP-AD-BsxynAF

<400> SEQUENCE: 164
acttactgtt gctcccatgg ctttcgctgc agatgctagc ccagactact ggca          54

<210> SEQ ID NO 165
<211> LENGTH: 44
<212> TYPE: DNA
<213> ORGANISM: Artificial Sequence
<220> FEATURE:
<223> OTHER INFORMATION: primer BsxynAR-HA

<400> SEQUENCE: 165
gtaatctggt acatcatatg ggtaccacac tgttacgtta gaac                     44

<210> SEQ ID NO 166
<211> LENGTH: 90
<212> TYPE: DNA
<213> ORGANISM: Artificial Sequence
<220> FEATURE:
<223> OTHER INFORMATION: primer mCWSP-AD-PX12-20-BsxynAF

<400> SEQUENCE: 166
acttactgtt gctcccatgg ctttcgctgc agatagaaaa cctggtaaag gtcctggtaa    60
acctagatcc gctagcccag actactggca                                     90

<210> SEQ ID NO 167
<211> LENGTH: 80
<212> TYPE: DNA
<213> ORGANISM: Artificial Sequence
<220> FEATURE:
<223> OTHER INFORMATION: primer BsxynAR-PX12-20-HA

<400> SEQUENCE: 167
gtaatctggt acatcatatg ggtaggatct aggtttacca ggacctttac caggttttct    60
ccacactgtt acgttagaac                                                80

<210> SEQ ID NO 168
<211> LENGTH: 89

```
<212> TYPE: PRT
<213> ORGANISM: Saccharomyces cerevisiae

<400> SEQUENCE: 168

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala
                85

<210> SEQ ID NO 169
<211> LENGTH: 280
<212> TYPE: DNA
<213> ORGANISM: Artificial Sequence
<220> FEATURE:
<223> OTHER INFORMATION: kozak-AFSP-stop

<400> SEQUENCE: 169
gatccaaacg atgagatttc cttcaattt tactgcagtt ttattcgcag catcctccgc      60
attagctgct ccagtcaaca ctacaacaga agatgaaacg gcacaaattc cggctgaagc     120
tgtcatcggt tactcagatt tagaagggga tttcgatgtt gctgttttgc cattttccaa     180
cagcacaaat aacgggttat tgtttataaa tactactatt gccagcattg ctgctaaaga     240
agaaggggta tctctcgaga aaagagaggc tgaagcttga                           280

<210> SEQ ID NO 170
<211> LENGTH: 61
<212> TYPE: DNA
<213> ORGANISM: Artificial Sequence
<220> FEATURE:
<223> OTHER INFORMATION: AFSP-hGH

<400> SEQUENCE: 170
agaagaaggg gtatctctcg agaaaagaga ggctgaagct ttcccaacca ttcccttatc      60
c                                                                     61

<210> SEQ ID NO 171
<211> LENGTH: 52
<212> TYPE: DNA
<213> ORGANISM: Artificial Sequence
<220> FEATURE:
<223> OTHER INFORMATION: hGHR-stopAOXt

<400> SEQUENCE: 171
attctgacat cctcttgagc ggccgcccct cagaagccac agctgccctc ca              52

<210> SEQ ID NO 172
<211> LENGTH: 97
<212> TYPE: DNA
<213> ORGANISM: Artificial Sequence
<220> FEATURE:
<223> OTHER INFORMATION: AFSP-PX12-20-hGH

<400> SEQUENCE: 172
```

```
agaagaaggg gtatctctcg agaaaagaga ggctgaagct agaaaacctg gtaaaggtcc    60
tggtaaacct agatccttcc caaccattcc cttatcc                             97
```

<210> SEQ ID NO 173
<211> LENGTH: 88
<212> TYPE: DNA
<213> ORGANISM: Artificial Sequence
<220> FEATURE:
<223> OTHER INFORMATION: hGHextR-PX12-20-stopAOXt

<400> SEQUENCE: 173

```
attctgacat cctcttgagc ggccgcccct caggatctag gtttaccagg acctttacca    60
ggttttctga agccacagct gccctcca                                       88
```

<210> SEQ ID NO 174
<211> LENGTH: 97
<212> TYPE: DNA
<213> ORGANISM: Artificial Sequence
<220> FEATURE:
<223> OTHER INFORMATION: AFSP-PX12-20v7-hGH

<400> SEQUENCE: 174

```
agaagaaggg gtatctctcg agaaaagaga ggctgaagct agaaaaccta aaaaaaaacc    60
taaaaaacct agatccttcc caaccattcc cttatcc                             97
```

<210> SEQ ID NO 175
<211> LENGTH: 238
<212> TYPE: PRT
<213> ORGANISM: Aequorea victoria

<400> SEQUENCE: 175

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Gln Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
210                 215                 220
Ser Ala Cys Cys His Thr His Gly Met Asp Glu Leu Tyr Arg
225                 230                 235

<210> SEQ ID NO 176
<211> LENGTH: 717
<212> TYPE: DNA
<213> ORGANISM: Aequorea victoria

<400> SEQUENCE: 176

| | | | | | |
|---|---|---|---|---|---|
| atgagcgggg | gcgaggagct | gttcgccggc | atcgtgcccg | tgctgatcga | gctggacggc | 60 |
| gacgtgcacg | gccacaagtt | cagcgtgcgc | ggcgagggcg | agggcgacgc | cgactacggc | 120 |
| aagctggaga | tcaagttcat | ctgcaccacc | ggcaagctgc | ccgtgccctg | gcccaccctg | 180 |
| gtgaccaccc | tctgctacgg | catccagtgc | ttcgcccgct | accccgagca | catgaagatg | 240 |
| aacgacttct | tcaagagcgc | catgcccgag | ggctacatcc | aggagcgcac | catccagttc | 300 |
| caggacgacg | gcaagtacaa | gacccgcggc | gaggtgaagt | tcgagggcga | caccctggtg | 360 |
| aaccgcatcg | agctgaaggg | caaggacttc | aaggaggacg | gcaacatcct | gggccacaag | 420 |
| ctggagtaca | gcttcaacag | ccacaacgtg | tacatccgcc | cgacaaggc | caacaacggc | 480 |
| ctggaggcta | acttcaagac | ccgccacaac | atcgagggcg | gcggcgtgca | gctggccgac | 540 |
| cactaccaga | ccaacgtgcc | cctgggcgac | ggccccgtgc | tgatccccat | caaccactac | 600 |
| ctgagcactc | agaccaagat | cagcaaggac | cgcaacgagg | cccgcgacca | catggtgctc | 660 |
| ctggagtcct | tcagcgcctg | ctgccacacc | cacggcatgg | acgagctgta | caggtaa | 717 |

<210> SEQ ID NO 177
<211> LENGTH: 37
<212> TYPE: DNA
<213> ORGANISM: Artificial Sequence
<220> FEATURE:
<223> OTHER INFORMATION: primer pENTR1A-1

<400> SEQUENCE: 177
agtcgactgg atccggtacc gccaccatga gcggggg            37

<210> SEQ ID NO 178
<211> LENGTH: 80
<212> TYPE: DNA
<213> ORGANISM: Artificial Sequence
<220> FEATURE:
<223> OTHER INFORMATION: primer pENTR1A-2

<400> SEQUENCE: 178
agtcgactgg atccggtacc gccaccatga ggtccccgg ctccggcccc ggctccccca      60
ggtccagcgg gggcgaggag                                                 80

<210> SEQ ID NO 179
<211> LENGTH: 80
<212> TYPE: DNA
<213> ORGANISM: Artificial Sequence
<220> FEATURE:
<223> OTHER INFORMATION: primer pENTR1A-3

<400> SEQUENCE: 179
agtcgactgg atccggtacc gccaccatga ggaagcccgg caagggcccc ggcaagccca      60
ggtccagcgg gggcgaggag                                                 80

```
<210> SEQ ID NO 180
<211> LENGTH: 80
<212> TYPE: DNA
<213> ORGANISM: Artificial Sequence
<220> FEATURE:
<223> OTHER INFORMATION: primer pENTR1A-4

<400> SEQUENCE: 180
agtcgactgg atccggtacc gccaccatga ggaagcccaa gaagaagccc aagaagccca    60
ggtccagcgg gggcgaggag                                                80

<210> SEQ ID NO 181
<211> LENGTH: 61
<212> TYPE: DNA
<213> ORGANISM: Artificial Sequence
<220> FEATURE:
<223> OTHER INFORMATION: primer pENTR1A-Flag-GFP

<400> SEQUENCE: 181
gtctagatat ctcgagttac ttgtcgtcgt cgtccttgta gtccctgtac agctcgtcca    60
t                                                                    61

<210> SEQ ID NO 182
<211> LENGTH: 54
<212> TYPE: DNA
<213> ORGANISM: Artificial Sequence
<220> FEATURE:
<223> OTHER INFORMATION: mCWSP-AD-BsestAF

<400> SEQUENCE: 182
acttactgtt gctcccatgg ctttcgctgc agatgctgaa cacaatccag tcgt          54

<210> SEQ ID NO 183
<211> LENGTH: 43
<212> TYPE: DNA
<213> ORGANISM: Artificial Sequence
<220> FEATURE:
<223> OTHER INFORMATION: BsestAR-HA

<400> SEQUENCE: 183
gtaatctggt acatcatatg ggtattaatt cgtattctgg ccc                      43

<210> SEQ ID NO 184
<211> LENGTH: 90
<212> TYPE: DNA
<213> ORGANISM: Artificial Sequence
<220> FEATURE:
<223> OTHER INFORMATION: mCWSP-AD-PX12-20-BsestAF

<400> SEQUENCE: 184
acttactgtt gctcccatgg ctttcgctgc agatagaaaa cctggtaaag gtcctggtaa    60
acctagatcc gctgaacaca atccagtcgt                                     90

<210> SEQ ID NO 185
<211> LENGTH: 181
<212> TYPE: PRT
<213> ORGANISM: Bacillus subtilis

<400> SEQUENCE: 185

Ala Glu His Asn Pro Val Val Met Val His Gly Ile Gly Gly Ala Ser
1               5                   10                  15

Phe Asn Phe Ala Gly Ile Lys Ser Tyr Leu Val Ser Gln Gly Trp Ser
            20                  25                  30
```

-continued

```
Arg Asp Lys Leu Tyr Ala Val Asp Phe Trp Asp Lys Thr Gly Thr Asn
            35                  40                  45

Tyr Asn Asn Gly Pro Val Leu Ser Arg Phe Val Gln Lys Val Leu Asp
     50                  55                  60

Glu Thr Gly Ala Lys Lys Val Asp Ile Val Ala His Ser Met Gly Gly
65                  70                  75                  80

Ala Asn Thr Leu Tyr Tyr Ile Lys Asn Leu Asp Gly Gly Asn Lys Val
                 85                  90                  95

Ala Asn Val Val Thr Leu Gly Gly Ala Asn Arg Leu Thr Thr Gly Lys
            100                 105                 110

Ala Leu Pro Gly Thr Asp Pro Asn Gln Lys Ile Leu Tyr Thr Ser Ile
            115                 120                 125

Tyr Ser Ser Ala Asp Met Ile Val Met Asn Tyr Leu Ser Arg Leu Asp
    130                 135                 140

Gly Ala Arg Asn Val Gln Ile His Gly Val Gly His Ile Gly Leu Leu
145                 150                 155                 160

Tyr Ser Ser Gln Val Asn Ser Leu Ile Lys Glu Gly Leu Asn Gly Gly
                165                 170                 175

Gly Gln Asn Thr Asn
            180

<210> SEQ ID NO 186
<211> LENGTH: 543
<212> TYPE: DNA
<213> ORGANISM: Bacillus subtilis

<400> SEQUENCE: 186
gctgaacaca atccagtcgt tatggttcac ggtattggag gggcatcatt caattttgcg     60
ggaattaaga gctatctcgt atctcagggc tggtcgcggg acaagctgta tgcagttgat    120
ttttgggaca agacaggcac aaattataac aatggaccgg tattatcacg atttgtgcaa    180
aaggttttag atgaaacggg tgcgaaaaaa gtggatattg tcgctcacag catgggggc     240
gcgaacacac tttactacat aaaaaatctg gacggcggaa ataaagttgc aaacgtcgtg    300
acgcttggcg gcgcgaaccg tttgacgaca ggcaaggcgc ttccgggaac agatccaaat    360
caaaagattt tatacacatc catttacagc agtgccgata tgattgtcat gaattactta    420
tcaagattag atggtgctag aaacgttcaa atccatggcg ttggacacat cggccttctg    480
tacagcagcc aagtcaacag cctgattaaa gaagggctga acggcggggg ccagaatacg    540
aat                                                                  543
```

PEPTIDE TAG AND TAGGED PROTEIN INCLUDING SAME

TECHNICAL FIELD

The present invention relates to a peptide tag, a tagged protein comprising the same, a DNA encoding the same, and a transformant comprising the DNA.

BACKGROUND ART

Today, due to the advancement of the gene recombination technique, production of useful proteins by heterologous expression has become common. For production of a useful protein by heterologous expression, factors such as selection of a promoter and a terminator, a translational enhancer, codon modification of the transgene, and intracellular transport and localization of the protein are studied for improving expression of the protein and the amount of the protein accumulated. For example, Patent Document 1 discloses a technique in which a bacterial toxin protein is expressed in a plant or the like, wherein the bacterial toxin protein is expressed in a state where it is linked through a peptide linker comprising prolines arranged at constant intervals (Patent Document 1).

There are also several techniques for improving expression of a protein of interest by linking a peptide tag thereto (Patent Document 2, Non-patent Documents 1 to 4). Most of these peptide tag-linking techniques improve the solubility of the protein of interest, suppress formation of inclusion bodies in the cell, and promote normal expression of the protein of interest. However, the techniques are not intended for improvement of the expression level of the protein. Moreover, most of such techniques are applied to expression systems using *E. coli*.

PRIOR ART DOCUMENTS

Patent Documents

[Patent Document 1] JP 5360727 B
[Patent Document 2] JP 5273438 B

Non-Patent Documents

[Non-patent Document 1] Smith, D. B. and Johnson, K. S.: Gene, 67, 31, 1988
[Non-patent Document 2] Marblestone, J. G et al.: Protein Sci., 15, 182, 2006
[Non-patent Document 3] di Guan, C. et al.: Gene, 67, 21, 1988
[Non-patent Document 4] Maria. C. V. et al.: Gene, 74, 365-373, 1988

SUMMARY OF THE INVENTION

Problems to be Solved by the Invention

By linking of a toxin protein using the peptide linker comprising prolines arranged at constant intervals as disclosed in Patent Document 1, high-level accumulation of a toxin fusion protein in a plant is possible. However, although this peptide linker is useful as a linker for linking a plurality of proteins to each other, its ability as a peptide tag for the purpose of high-level expression of a single protein of interest has not been sufficiently studied, and such an ability remains to be further studied. In view of this, an object of the present invention is to provide a peptide tag for use in cases where a protein of interest is expressed in a host cell, wherein the peptide tag is linked to the protein of interest to enable achievement of an increased expression level of the protein of interest.

Means for Solving the Problems

In an attempt to improve the performances of the linker peptides disclosed in Patent Document 1 as peptide tags for high-level expression of protein, the present inventors first focused on the presence of proline in these peptides (PG12 and PG17), and expected that further improvement of useful properties of the peptides may be possible by substituting serine (S) and/or glycine (G) present between proline (P) and proline (P) with an amino acid(s) having different physicochemical properties. More specifically, peptide tags were prepared by substituting serine (S) and/or glycine (G) in the peptides with a basic amino acid(s) such as lysine (K) and/or arginine (R), with an acidic amino acid(s) such as aspartic acid (D) and/or glutamic acid (E), and/or with an amino acid(s) having different steric properties and/or polarity whose side chain(s) is/are uncharged such as alanine (A), threonine (T), leucine (L), methionine (M), asparagine (N), and/or glutamine (Q), and each peptide tag was fused with a protein of interest to attempt improvement of expression of the protein of interest. As a result, it was found that, by the addition of the peptide prepared by the substitution of S and/or G present between P and P with K, L, N, Q, and/or R in PG12 or PG17 to the protein of interest, the expression level of the protein of interest can be improved. The present invention was accomplished based on such findings.

That is, the present invention is as follows.

[1] A peptide comprising the following sequence:

wherein X, Y, and Z each represent an amino acid residue independently selected from the group consisting of arginine (R), glycine (G), serine (S), lysine (K), threonine (T), leucine (L), asparagine (N), glutamine (Q), and histidine (H), with the proviso that at least one Y represents K, L, N, Q, H, or R; and wherein m represents an integer of 0 to 5; n represents 1, 2, or 3 (wherein n preferably represents 2 or 3); q represents an integer of 1 to 10; and r represents an integer of 0 to 10.
[2] The peptide according to [1], wherein the content of G and S is less than 60%.
[3] The peptide according to [1] or [2], wherein the peptide has a length of 6 to 50 amino acids.
[4] The peptide according to any one of [1] to [3], wherein said peptide comprises the amino acid sequence of SEQ ID NO: 25, 28, 30, 32, 34, 36, 38, 40, 42, 44, 46, 48, 50, 52, 54, 58, 60, 64, 66, 92, 94, 96, 98, 100, 102, 104, 106, 108, 110, 112, 114, 116, 118, 120, 122, 124, 126, 128, 130, 132, 134, 136, 140, 142, 143, 145, 147, 149, 151, 153, 155, or 157.
[5] A tagged protein comprising the peptide according to any one of [1] to [4] and a useful protein.
[6] The tagged protein according to [5], wherein the useful protein is selected from the group consisting of human growth hormone, interferon (3, xylanase, esterase, and green fluorescent protein (GFP).
[7] The tagged protein according to [5] or [6], wherein the peptide is linked to the useful protein through a protease recognition sequence.
[8] The tagged protein according to any one of [5] to [7], further comprising a secretion signal.

[9] A DNA encoding the tagged protein according to any one of [5] to [8].

[10] A recombinant vector comprising the DNA according to [9].

[11] A transformant prepared by transformation with the DNA according to [9] or the recombinant vector according to [10].

[12] The transformant according to [11], wherein the transformant is yeast, E. coli, Brevibacillus, an insect cell, or a mammalian cell (which includes a human cultured cell, but does not include a human individual).

[13] A method for producing a tagged protein, comprising culturing the transformant according to [11] or [12] to allow accumulation of the tagged protein, and collecting the tagged protein.

Advantages of the Invention

By using the peptide tag of the present invention, the expression level of a protein of interest can be improved. Thus, the present invention is useful for production of a protein using a cell such as yeast, E. coli, or Brevibacillus. In particular, since effects of tags on the expression level have so far been unclear in E. coli and Brevibacillus, achievement of improvement of expression in these cells using the tag is industrially very useful. Since the peptide tag of the present invention may have a length of as small as 10 to 30 amino acids, it is less likely to affect the structure or function of the protein of interest to which the peptide tag is added. Thus, it is highly likely that cleavage treatment after the expression can be omitted. If removal of the peptide tag is required, a protease recognition sequence may be inserted therefor.

EMBODIMENTS FOR CARRYING OUT THE INVENTION

Figure 1:
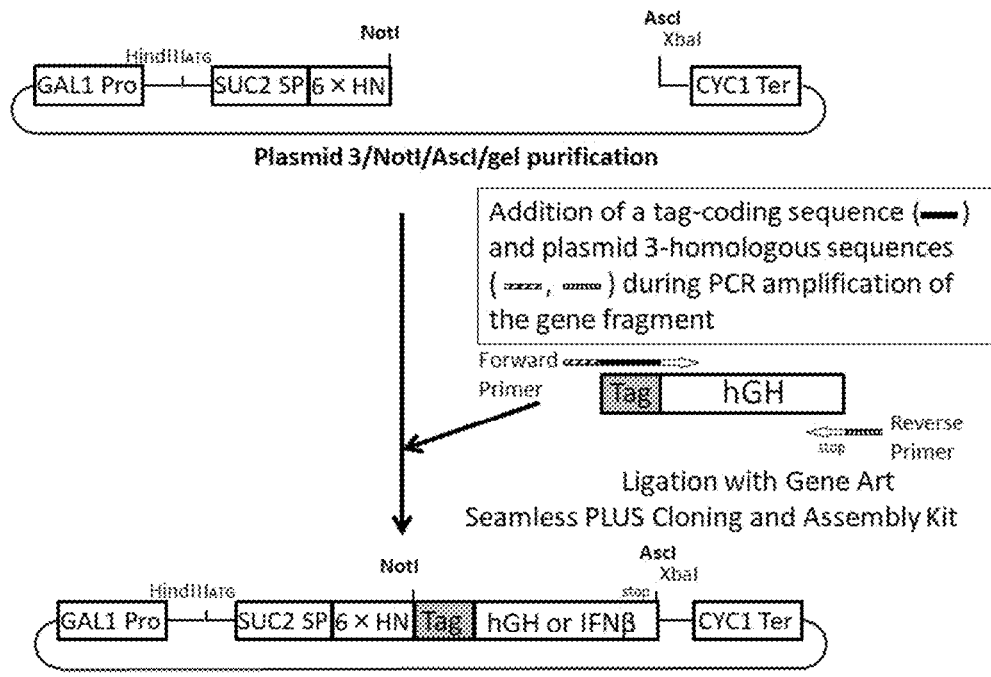
FIG. 1 is a diagram illustrating a procedure for construction of a gene for introduction into Saccharomyces yeast (for expression of hGH or IFNβ).

The peptide (also referred to as peptide tag) of the present invention has the following sequence.

$X_m(PY_n)_qPZ_r$ $X_m$ means m-consecutive "X"s, wherein the m "X"s may be either the same amino acid residues or different amino acid residues selected from the group consisting of R, G, S, K, T, L, N, Q, and H. m is an integer of 0 to 5, preferably an integer of 1 to 5, more preferably an integer of 1 to 3.

$(PY_n)_q$ means q-consecutive "$PY_n$"s, that is, since n is 1, 2, or 3, it means q-consecutive "PY"(s), "PYY"(s), and/or "PYYY"(s) (wherein P represents proline). The total number of the consecutive "PY"(s), "PYY"(s), and/or "PYYY"(s) is q.

Here, the "Y"s may be either the same amino acid residues or different amino acid residues selected from the group consisting of R, G, S, K, T, L, N, and Q, with the proviso that at least one of the "Y"s included in the q consecutive "$PY_n$"s is K, L, N, Q, H, or R. More preferably, at least two "Y"s included in the q-consecutive "$PY_n$"s are K, L, N, Q, H, or R. q is an integer of 1 to 10, preferably an integer of 2 to 10, more preferably an integer of 2 to 5, still more preferably an integer of 2 to 3.

$PZ_r$ means r-consecutive "Z"s after "P", wherein the r "Z"s may be either the same amino acid residues or different amino acid residues selected from the group consisting of R, G, S, K, T, L, N, and Q. r is an integer of 0 to 10, preferably an integer of 1 to 10, more preferably an integer of 1 to 5.

The peptide of the present invention has a length of preferably 6 to 50 amino acids, more preferably 6 to 40 amino acids, still more preferably 8 to 40 amino acids, still more preferably 10 to 30 amino acids, still more preferably 12 to 25 amino acids, especially preferably 12 to 20 amino acids.

In the peptide of the present invention, the total content of glycine and serine with respect to the total amino acids is preferably less than 60%, more preferably less than 57%.

In one mode of the peptide of the present invention, the peptide has the same amino acid sequence as PG12 or PG17 except that one or several (for example, 1 to 6, preferably 2 to 6) amino acids other than P are substituted with K, L, N, and/or Q. In another mode, the peptide has the same amino acid sequence as PG12 or PG17 except that one or several (for example, 1 to 5, preferably 2 to 5) amino acids other than P or R are substituted with R. Here, the amino acid(s) substituted in PG12 or PG17 is/are more preferably an amino acid(s) between P and P.

The peptide of the present invention is preferably a peptide comprising the amino acid sequence represented by SEQ ID NO:25, 28, 30, 32, 34, 36, 38, 40, 42, 44, 46, 48, 50, 52, 54, 58, 60, 64, 66, 92, 94, 96, 98, 100, 102, 104, 106, 108, 110, 112, 114, 116, 118, 120, 122, 124, 126, 128, 130, 132, 134, 136, 140, 142, 143, 145, 147, 149, 151, 153, 155, or 157.

In the tagged protein of the present invention, the peptide tag of the present invention is bound to a protein of interest (the tagged protein is also referred to as a fusion protein of the tag and the protein of interest). The peptide tag may be bound to the N-terminus of the protein of interest; the peptide tag may be bound to the C-terminus of the protein of interest; or the peptide tag may be bound to each of both the N-terminus and the C-terminus of the protein of interest. The peptide tag(s) may be directly bound to the N-terminus and/or the C-terminus of the protein of interest, or may be bound thereto through a sequence(s) of one to several amino acids (for example, 1 to 5 amino acid(s)). The sequence of the one to several amino acids may be an arbitrary sequence as long as the sequence does not adversely affects the function and the expression level of the tagged protein. In cases where the sequence is a protease recognition sequence, the peptide tag can be cleaved off from the useful protein after the expression and purification. Examples of the protease recognition sequence include the factor Xa recognition sequence (IEGR; SEQ ID NO:10). The tagged protein of the present invention may also include another tag sequence necessary for detection or purification, such as a His tag, HN tag (for example, SEQ ID NO:6), or FLAG tag.

Examples of the useful protein contained in the tagged protein of the present invention include, but are not limited to, growth factors, hormones, cytokines, blood proteins, enzymes, antigens, antibodies, transcription factors, receptors, fluorescent proteins, and partial peptides thereof.

Examples of the enzymes include lipase, protease, steroid-synthesizing enzyme, kinase, phosphatase, xylanase, esterase, methylase, demethylase, oxidase, reductase, cellulase, aromatase, collagenase, transglutaminase, glycosidase, and chitinase.

Examples of the growth factors include epidermal growth factor (EGF), insulin-like growth factor (IGF), transforming growth factor (TGF), nerve growth factor (NGF), brain-derived neurotrophic factor (BDNF), vascular endothelial growth factor (VEGF), granulocyte colony-stimulating factor (G-CSF), granulocyte-macrophage colony-stimulating factor (GM-CSF), platelet-derived growth factor (PDGF), erythropoietin (EPO), thrombopoietin (TPO), fibroblast growth factor (FGF), and hepatocyte growth factor (HGF).

Examples of the hormones include insulin, glucagon, somatostatin, growth hormones (for example, SEQ ID NO:1), parathyroid hormone, prolactin, leptin, and calcitonin.

Examples of the cytokines include interleukins, interferons (IFNα, IFNβ (for example, SEQ ID NO:2), IFNγ), and tumor necrosis factor (TNF).

Examples of the blood proteins include thrombin, serum albumin, factor VII, factor VIII, factor IX, factor X, and tissue plasminogen activator.

Examples of the antibodies include complete antibodies, Fab, F(ab'), F(ab')$_2$, Fc, Fc fusion proteins, heavy chain (H-chain), light chain (L-chain), single-chain Fv (scFv), sc(Fv)$_2$, disulfide-linked Fv (sdFv), and diabodies.

The antigen proteins to be used as vaccines are not limited as long as the immune response can be induced, and may be appropriately selected depending on the expected target of the immune response. Examples of the antigen proteins include proteins derived from pathogenic bacteria and proteins derived from pathogenic viruses.

To the tagged protein of the present invention, a secretion signal peptide that functions in a host cell may be added for secretory production. Examples of the secretion signal peptide include invertase secretion signal (for example, SEQ ID NO:5), P3 secretion signal, and α-factor secretion signal (SEQ ID NO:168) in cases where yeast is used as the host; PelB secretion signal in cases where *E. coli* is used as the host; and P22 secretion signal in cases where *Brevibacillus* is used as the host. In cases where a plant is used as the host, examples of the secretion signal peptide include those derived from plants belonging to the families Solanaceae, Rosaceae, Brassicaceae, and Asteraceae, preferably those derived from plants belonging to genera such as *Nicotiana, Arabidopsis, Fragaria,* and *Lactuca*, more preferably those derived from *Nicotiana tabacum, Arabidopsis thaliana, Fragariaxananassa, Lactuca sativa,* and the like.

For allowing expression in a particular cellular compartment, a transport signal peptide such as an endoplasmic reticulum retention signal peptide or a vacuole transport signal peptide may be added to the tagged protein of the present invention The tagged protein of the present invention may be chemically synthesized, or may be produced by genetic engineering. A method for its production by genetic engineering will be described later.

The DNA of the present invention is characterized in that it comprises a DNA encoding the tagged protein of the present invention. That is, the DNA of the present invention comprises a DNA encoding the useful protein and a DNA encoding the peptide tag. The DNA encoding the useful protein and the DNA encoding the peptide tag are linked to each other in the same reading frame.

The DNA encoding the useful protein may be obtained by, for example, a common genetic engineering method based on a known nucleotide sequence.

Preferably, in the DNA encoding the tagged protein of the present invention, a codon(s) corresponding to an amino acid(s) constituting the tagged protein is/are modified as appropriate such that the translation level of the hybrid protein increases depending on the host cell in which the protein is to be produced. For the method of the codon modification, one may refer to, for example, the method of Kang et al. (2004). Examples of the method also include methods in which codons frequently used in the host cell are selected, methods in which codons with high GC contents are selected, and methods in which codons frequently used in house-keeping genes of the host cell are selected.

For improving expression in the host cell, the DNA of the present invention may comprise an enhancer sequence or the like that functions in the host cell. Examples of the enhancer include the Kozak sequence, and the 5'-untranslated region of an alcohol dehydrogenase gene derived from a plant.

The DNA of the present invention can be prepared by a common genetic engineering technique. For example, a DNA encoding the peptide tag of the present invention, a DNA encoding the useful protein, and the like may be linked to each other using PCR, DNA ligase, and/or the like, to construct the DNA of the present invention.

The recombinant vector of the present invention may be a vector in which the DNA encoding the tagged protein is inserted such that expression of the protein is possible in the host cell to which the vector is introduced. The vector is not limited as long as it can replicate in the host cell. Examples of the vector include plasmid DNAs and viral DNAs. The vector preferably contains a selection marker such as a drug resistance gene. Specific examples of the plasmid vectors include the pTrcHis2 vector, pUC119, pBR322, pBluescript II KS+, pYES2, pAUR123, pQE-Tri, pET, pGEM-3Z, pGEX, pMAL, pRI909, pRI910, pBI221, pBI121, pBI101, pIG121Hm, pTrc99A, pKK223, pA1-11, pXT1, pRc/CMV, pRc/RSV, pcDNA I/Neo, p3×FLAG-CMV-14, pCAT3, pcDNA3.1, and pCMV.

The promoter used in the vector may be appropriately selected depending on the host cell to which the vector is introduced. In cases of expression in yeast, examples of the promoter include the GAL1 promoter, PGK1 promoter, TEF1 promoter, ADH1 promoter, TPI1 promoter, and PYK1 promoter. In cases of expression in a plant, examples of the promoter include the cauliflower mosaic virus 35S promoter, rice actin promoter, maize ubiquitin promoter, and lettuce ubiquitin promoter. In cases of expression in *E. coli*, examples of the promoter include the T7 promoter. In cases of expression in *Brevibacillus*, examples of the promoter include the P2 promoter and the P22 promoter. The promoter may be an inducible promoter. Examples of the inducible promoter include lac, tac, and trc, which are inducible with IPTG; trp, which is inducible with IAA; ara, which is inducible with L-arabinose; Pzt-1, which is inducible with tetracycline; the $P_L$ promoter, which is inducible by heat (42° C.); and the promoter of the cspA gene, which is a cold shock gene.

When necessary, a terminator sequence may also be included depending on the host cell.

The recombinant vector of the present invention may be prepared by, for example, cleaving a DNA construct with an appropriate restriction enzyme, or adding a restriction site by PCR, and then inserting the resulting DNA into a restriction site or a multicloning site of a vector.

The transformant of the present invention is characterized in that it is transformed with the DNA or a recombinant vector comprising the DNA. The host cell used for the transformation may be either a eukaryotic cell or a prokaryotic cell. A eukaryotic cell is preferred.

Preferred examples of the eukaryotic cell include yeast cells, mammalian cells, plant cells, and insect cells. Examples of the yeast include *Saccharomyces cerevisiae, Candida utilis, Schizosaccharomyces pombe*, and *Pichia pastoris*. Further, a microorganism such as *Aspergillus* may be used. Examples of the prokaryotic cell include *Escherichia coli, Lactobacillus, Bacillus, Brevibacillus, Agrobacterium tumefaciens*, and actinomycetes. Examples of the plant cells include cells of plants belonging to Astaraceae such as *Lactuca*; Solanaceae; Brassicaceae; Rosaceae; or Chenopodiaceae.

The transformant to be used in the present invention can be prepared by introducing the recombinant vector of the present invention into host cells by a common genetic engineering technique. Examples of the method used include the electroporation method (Tada, et al., 1990, Theor. Appl. Genet, 80: 475), the protoplast method (Gene, 39, 281-286 (1985)), the polyethylene glycol method (Lazzeri, et al., 1991, Theor. Appl. Genet. 81:437), the introduction method utilizing *Agrobacterium* (Hood, et al., 1993, Transgenic, Res. 2: 218, Hiei, et al., 1994 Plant J. 6: 271), the particle gun method (Sanford, et al., 1987, J. Part. Sci. tech. 5:27), and the polycation method (Ohtsuki, et al., FEBS Lett. 1998 May 29; 428(3): 235-40.). The gene expression may be transient expression, or may be stable expression based on incorporation into the chromosome.

After the introduction of the recombinant vector of the present invention into the host cells, a transformant can be selected based on a phenotype of the selection marker. By culturing the selected transformant, the tagged protein can be produced. The medium and the conditions used for the culture may be appropriately selected depending on the species of the transformant.

In cases where the host cell is a plant cell, a plant body can be regenerated by culturing a selected plant cell by a conventional method, and the tagged protein can be accumulated in the plant cell or outside the cell membrane of the plant cell.

The protein comprising the peptide tag of the present invention accumulated in the medium or cells can be separated and purified according to a method well known to those skilled in the art. For example, the separation and purification can be carried out by an appropriate known method such as salting-out, ethanol precipitation, ultrafiltration, gel filtration chromatography, ion-exchange column chromatography, affinity chromatography, high/medium-pressure liquid chromatography, reversed-phase chromatography, or hydrophobic chromatography, or by combination of any of these.

Examples of the present invention are described below, but the present invention is not limited to the Examples.

EXAMPLES (1) Construction of Gene Expression Plasmid Encoding Peptide-Tagged Protein for Yeast As proteins to which a peptide tag is to be added, 1) human growth hormone (hGH, SEQ ID NO:1) and 2) human interferon β-1b (IFNβ, SEQ ID NO:2) were used. An artificial synthetic DNA encoding hGH (SEQ ID NO:3) was inserted into the EcoRV recognition site of a pUC19-modified plasmid pTRU5 (Fasmac), to obtain plasmid 1. An artificial synthetic DNA encoding IFNβ (SEQ ID NO:4) was inserted into the EcoRV recognition site of a pUC19-modified plasmid pTRU5, to obtain plasmid 2.

An artificial synthetic DNA (SEQ ID NO:7) prepared by adding a DNA sequence encoding a yeast invertase SUC2 signal peptide (SUC2SP, SEQ ID NO:5; Hashimoto et al., Protein Engineering, 1998 2; 75-77) and a 6× HN tag for detection and purification (SEQ ID NO:6) to the 5'-end of a multicloning site composed of the NotI, SalI, SfiI, XhoI, and AscI recognition sequences was inserted into the HindIII-XbaI site of pYES2 (Invitrogen) such that the SUC2SP and the 6× HN tag were added to the N-terminus of the expressed protein, to prepare plasmid 3 for expression in yeast.

By the following procedure, plasmids for expression of hGH or IFNβ having various tags (Table 1) at the N- or C-terminus, or at both the N- and C-termini, in yeast were constructed (FIG. 1).

First, for the addition of the various tags to the N- or C-terminus of hGH or IFNβ, or to both the N- and C-termini, PCR was carried out using the combinations of a template plasmid, a forward primer, and a reverse primer shown in Table 2. To the 5'-end of each primer, a sequence homologous to plasmid 3 was added. For the PCR, KOD-PLUS-Ver. 2 (Toyobo Co., Ltd.) was used. A reaction liquid in an amount of 50 µl was prepared such that it contained 2 pg/µl template plasmid, 0.3 µM forward primer, 0.3 µM reverse primer, 0.2 mM dNTPs, 1× Buffer for KOD-Plus-Ver. 2, 1.5 mM MgSO$_4$, and 0.02 U/µl KOD-PLUS-Ver. 2. The reaction liquid was heated at 94° C. for 5 minutes, and this was followed by 25 cycles of treatment each composed of heating at 98° C. for 10 seconds, at 60° C. for 30 seconds, and then at 68° C. for 40 seconds. Finally, the reaction liquid was heated at 68° C. for 5 minutes. The resulting amplification fragment was purified with a QIAquick PCR Purification Kit (QIAGEN). Plasmid 3 was digested with NotI and AscI, and then separated by electrophoresis using 0.8% SeaKem GTG Agarose (Lonza), followed by extraction from the gel using a QIAquick Gel Extraction Kit (QIAGEN). With the extracted plasmid 3 in an amount corresponding to about 50 ng, 2 µl of the purified PCR product was mixed, and the liquid volume was adjusted to 5 µl. The resulting mixture was mixed with 5 µl of 2× Enzyme Mix attached to a Gene Art Seamless PLUS Cloning and Assembly Kit (Applied Biosystem), and then left to stand at room temperature for 30 minutes, followed by being left to stand on ice for 5 minutes. With the competent cells DH10B T1 SA attached to the kit, 5 µl of the reaction liquid was mixed, and the resulting mixture was left to stand on ice for 30 minutes. The mixture was then warmed at 37° C. for 10 minutes, and left to stand on ice for 2 minutes, followed by addition of 250 µl of SOC thereto and shaking at 37° C. at 200 rpm for 1 hour. Subsequently, 50 µl of the shaken product was applied to 2×YT agar medium (16 g/l Bacto tryptone, 10 g/l Bacto Yeast Extract, 5 g/l NaCl, 15 g/l Bacto Agar) supplemented with 100 mg/l ampicillin, and static culture was carried out at 37° C. overnight, to obtain transformed colonies. A colony was transferred to 2×YT liquid medium (16 g/l Bacto tryptone, 10 g/l Bacto Yeast Extract, and 5 g/l NaCl) supplemented with 100 mg/l ampicillin, and shake culture was carried out at 37° C. at 200 rpm overnight, followed by extraction of plasmid. After confirmation of the nucleotide sequence, the plasmid was used for transformation of yeast.

(2) Transformation of Yeast

Yeast (*Saccharomyces cerevisiae* INVSc1, Invitrogen) was subjected to shake culture in YPD medium (1% yeast extract, 2% peptone, 2% dextrose (D-glucose)) at 30° C. at 200 rpm overnight. The resulting culture was diluted such that the turbidity at a wavelength of 600 nm (OD$_{600}$) in 10 ml of YPD became 0.2 to 0.4. Shake culture was then carried out at 30° C. at 200 rpm until OD$_{600}$ reached 0.6 to 1.0. After performing centrifugation at 500×g at room temperature for 5 minutes, the cells were pelletized, and the supernatant was discarded. The resulting pellet was suspended in 10 ml of Solution I (S. c. EasyComp Transformation Kit, Invitrogen). Further, after performing centrifugation at 500×g at room temperature for 5 minutes, the cells were pelletized, and the supernatant was discarded. The resulting pellet was suspended in 1 ml of Solution II (S. c. EasyComp Transformation Kit, Invitrogen), and aliquoted in 50-µl volumes to provide competent cells. The competent cells were stored in a deep freezer at −80° C. until use.

The competent cells obtained were thawed and allowed to warm to room temperature. After adding 1 µg of the plasmid for expression of the peptide-tagged protein prepared as described above to the competent cells, 500 µl of Solution III (room temperature) was added to the resulting mixture, followed by vortexing the mixture and then leaving the mixture to stand at 30° C. for 1 hour (while vortexing the mixture at 15-minute intervals). Thereafter, 50 µl of the mixture after being left was applied to SC-Ura medium (6.7 g/L yeast nitrogen base, 0.1 g/L adenine, 0.1 g/L arginine, 0.1 g/L cysteine, 0.1 g/L leucine, 0.1 g/L lysine, 0.1 g/L threonine, 0.1 g/L tryptophan, 0.05 g/L aspartic acid, 0.05 g/L histidine, 0.05 g/L isoleucine, 0.05 g/L methionine, 0.05 g/L phenylalanine, 0.05 g/L proline, 0.05 g/L serine, 0.05 g/L tyrosine, 0.05 g/L valine) supplemented with 2% glucose and 2% Bacto Agar, and static culture was carried out at 30° C. for 2 to 3 days to obtain transformed colonies.

(3) Protein Induction Culture of Yeast

A single colony after the transformation was smeared on a plate medium (SC-Ura, 2% dextrose), and then left to stand in an incubator at 30° C. for 24 hours to perform culture. Subsequently, cells were scraped with a 1-µl sterile disposable loop from the plate medium after the culture, and then inoculated into 3 ml of a preculture medium (SC-Ura, 2% galactose) placed in a sterile 14-ml polystyrene tube. Shake culture was carried out at 30° C. at 200 rpm for 16 hours. After completion of the culture, the turbidity was measured at 600 nm using a spectrophotometer. The culture in the amount required for the turbidity to become 0.4 by resuspension in 3 ml of a medium was taken into a sterile 1.5-ml Eppendorf tube, and then centrifugation was carried out at 3000× g at 4° C. for 5 minutes. After removing the supernatant, the precipitate was suspended in 1 ml of an induction medium (SC-Ura, 1% galactose, 1% raffinose), and the resulting suspension was combined with 2 ml of the induction medium preliminarily placed in a sterile 14-ml polystyrene tube, followed by performing shake culture at 30° C. at 200 rpm for 24 hours. After completion of the culture, 400 µl of the culture liquid was taken into a 1.5-ml Eppendorf tube, and centrifugation was carried out at 3000× g at 4° C. for 5 minutes. After removing the supernatant, the cells were frozen in liquid nitrogen, and then stored in a deep freezer at −80° C.

(4) Extraction of Protein from Yeast

Using the transgenic yeast cells stored at −80° C. after the freezing in liquid nitrogen, protein extraction was carried out according to the method by Akira Hosomi et al. (Akira Hosomi, et al, J Biol Chem, 285, (32), 24324-24334, 2010). To the stored sample, 720 µl of distilled water was added, and the resulting mixture was stirred using a vortex mixer. Thereafter, 80 µl of 1.0 N NaOH was added to the mixture, and the mixture was stirred again using a vortex mixer, followed by being left to stand on ice for 10 minutes. Subsequently, centrifugation was carried out at 4° C. at 15,000 g for 5 minutes, and the supernatant was discarded, followed by collecting the precipitate. To the precipitate, 100 µl of a sample buffer (EZ Apply, manufactured by ATTO) was added, and the resulting mixture was stirred using a vortex mixer, followed by heating in boiling water for 10 minutes to perform SDS treatment of the sample.

(5) Construction of Gene Expression Plasmid Encoding Peptide-Tagged Protein for *E. coli*

An artificial synthetic DNA (SEQ ID NO:78) was prepared and inserted into the XbaI-BlpI site of pET-15b (Novagen) to prepare plasmid 4 for expression in *E. coli*. The artificial synthetic DNA (SEQ ID NO:78) is a DNA prepared from the gene expression cassette between XbaI-BlpI in pET-22b(+) (Novagen) by replacing the region from immediately after the *E. coli* PelB signal peptide (PelBSP)

to the stop codon with a 6×HN tag for detection/purification (SEQ ID NO:6) followed by a multicloning site composed of the NotI, SalI, SfiI, XhoI, and AscI recognition sequences.

Figure 2:
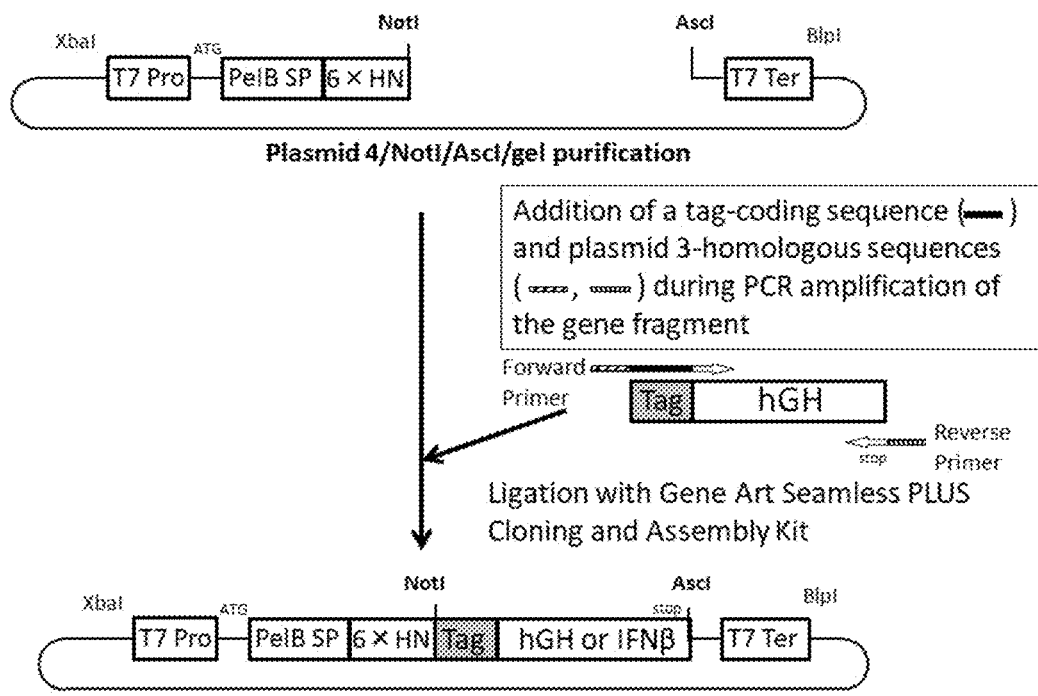
FIG. 2 is a diagram illustrating a procedure for construction of a gene for introduction into E. coli (for expression of hGH or IFNβ).

By the following procedure, plasmids for expression of hGH or IFNβ in *E. coli*, having various tags at the N- or C-terminus, or at both the N- and C-termini, were constructed (FIG. 2).

First, for the addition of the various tags to the N- or C-terminus of hGH or IFNβ, or to both the N- and C-termini, PCR was carried out using the combinations of a template plasmid, a forward primer, and a reverse primer shown in Table 3. To the 5'-end of each primer, a sequence homologous to plasmid 4 was added. For the PCR, KOD-PLUS-Ver. 2 (Toyobo Co., Ltd.) was used. A reaction liquid in an amount of 50 μl was prepared such that it contained 2 pg/μl template plasmid, 0.3 μM forward primer, 0.3 μM reverse primer, 0.2 mM dNTPs, 1× Buffer for KOD-Plus-Ver. 2, 1.5 mM $MgSO_4$, and 0.02 U/μl KOD-PLUS-Ver. 2. The reaction liquid was heated at 94° C. for 5 minutes, and this was followed by 25 cycles of treatment each composed of heating at 98° C. for 10 seconds, at 60° C. for 30 seconds, and then at 68° C. for 40 seconds. Finally, the reaction liquid was heated at 68° C. for 5 minutes. The resulting amplification fragment was purified with a QIAquick PCR Purification Kit (QIAGEN). Plasmid 4 was digested with NotI and AscI, and then separated by electrophoresis using 0.8% SeaKem GTG Agarose (Lonza), followed by extraction from the gel using a QIAquick Gel Extraction Kit (QIAGEN). With the extracted plasmid 4 in an amount corresponding to about 50 ng, 2 μl of the purified PCR product was mixed, and the liquid volume was adjusted to 5 μl. The resulting mixture was mixed with 5 μl of 2× Enzyme Mix attached to a Gene Art Seamless PLUS Cloning and Assembly Kit (Applied Biosystem), and then left to stand at room temperature for 30 minutes, followed by being left to stand on ice for 5 minutes. With the *E. coli* competent cells DH10B T1 SA attached to the kit, 5 μl of the reaction liquid was mixed, and the resulting mixture was left to stand on ice for 30 minutes. The mixture was then warmed at 37° C. for 10 minutes, and left to stand on ice for 2 minutes, followed by addition of 250 μl of SOC thereto and shaking at 37° C. at 200 rpm for 1 hour. Subsequently, 50 μl of the shaken product was applied to 2× YT agar medium (16 g/l Bacto tryptone, 10 g/l Bacto Yeast Extract, 5 g/l NaCl, and 15 g/l Bacto Agar) supplemented with 100 mg/l ampicillin, and static culture was carried out at 37° C. overnight to obtain transformed colonies. A colony was transferred to 2× YT liquid medium (16 g/l Bacto tryptone, 10 g/l Bacto Yeast Extract, 5 g/l NaCl) supplemented with 100 mg/l ampicillin, and shake culture was carried out at 37° C. at 200 rpm overnight, followed by extraction of plasmid. After confirmation of the nucleotide sequence, the plasmid was used for transformation of *E. coli* for expression of protein.

(6) Transformation of *E. coli* for Protein Expression

A glycerol stock of *E. coli* BL21 (DE3) (Novagen) was inoculated into 3 ml of SOB medium (20 g/l Bacto tryptone, 5 g/l Bacto Yeast Extract, 10 mM NaCl, 2.5 mM KCl, 10 mM $MgSO_4$, 10 mM $MgCl_2$) placed in a sterile 14-ml polystyrene tube, and shake culture was carried out at 37° C. at 200 rpm overnight. To 100 ml of SOB medium placed in a sterile Erlenmeyer flask, 0.2 ml of the resulting culture liquid was inoculated, and shake culture was carried out at 30° C. at 200 rpm. When the turbidity at a wavelength of 600 nm (OD600) reached 0.4 to 0.6, the culture liquid was cooled with ice for 10 to 30 minutes to stop the culture. The culture liquid was transferred to 50-ml conical tubes, and centrifugation was carried out at 2500× g at 4° C. for 10 minutes (×2 tubes). After discarding the supernatant, ice-cold 15 ml TB (10 mM PIPES-KOH, pH 6.7, 15 mM $CaCl_2$, 0.25 M KCl, 55 mM $MnCl_2$) was added to the pellets, and the pellets were gently suspended (×2 tubes). The suspension contained in the two tubes was combined into one tube, and centrifugation was carried out at 2500× g at 4° C. for 10 minutes. After discarding the supernatant, 10 ml of ice-cold TB was added to the pellet, and the pellet was gently suspended. After addition of 700 μl of DMSO thereto, the pellet was gently suspended under ice-cooling. The resulting suspension was aliquoted in 50-μl volumes into 1.5-ml microtubes to provide competent cells. After freezing the competent cells with liquid nitrogen, the cells were stored at −80° C. until use.

The obtained competent cells were thawed on ice, and 1 ng of the plasmid for expression of the peptide-tagged protein for *E. coli* prepared as described above was added to the cells, followed by gently stirring the resulting mixture and leaving the mixture to stand on ice for 30 minutes. The cells were then treated (heat-shocked) at 42° C. for 30 to 45 seconds, and left to stand on ice for 2 minutes. After adding 250 μl of SOC, the tube was kept in a horizontal position, and shaken at 37° C. at 200 rpm for 1 hour. Subsequently, 50 μl of the shaken product was applied to 2× YT agar medium supplemented with 100 mg/l ampicillin, and static culture was carried out at 37° C. overnight to obtain transformed colonies.

(7) Protein Induction Culture of *E. coli*

A single colony after the transformation was smeared on a plate medium (2×YT, 100 ppm Ampicillin), and then left to stand in an incubator at 37° C. overnight to perform culture. Subsequently, bacterial cells were scraped with a sterile disposable loop from the plate medium after the culture, and then inoculated into 2 ml of a preculture medium (LB, 100 ppm Ampicillin) placed in a sterile 14-ml polystyrene tube. Shake culture was carried out at 37° C. at 200 rpm until the $OD_{600}$ value reached 0.6 to 1.0. The culture in the amount required for the $OD_{600}$ value to become 0.3 by addition of 1.0 ml of LB medium (100 ppm Ampicillin) to the precipitate obtained after removal of the centrifuge supernatant from the culture was taken into a 1.5-ml Eppendorf tube, and left to stand at 4° C. (in a refrigerator) overnight. On the next day, the sample was centrifuged at 2000 rpm at 4° C. for 30 minutes, and then the supernatant was removed, followed by adding 1 ml of fresh LB medium (100 ppm Ampicillin) to the sample and suspending the precipitate. Further, 300 μl out of 1 ml of the sample was inoculated into 2.7 ml of LB medium (100 ppm Ampicillin) such that the $OD_{600}$ value became 0.03, and then shake culture was carried out at 37° C. at 200 rpm until the $OD_{600}$ value reached 0.4 to 1.0. Subsequently, 3 μl (final concentration, 1 mM) of 1 M IPTG (inducer) was added to the culture, and shake culture was carried out at 37° C. at 200 rpm for 3 hours. After completion of the culture, the test tube containing the sample was cooled on ice for 5 minutes to stop the growth of *E. coli*, and 200 μl of the culture liquid was taken into another 1.5-ml Eppendorf tube, followed by performing centrifugation at 5000 rpm at 4° C. for 5 minutes. Subsequently, the supernatant was removed, and then the bacterial cells were frozen with liquid nitrogen, followed by cryopreservation at −80° C.

(8) Extraction of Protein from *E. coli*

To the cryopreserved sample, 100 μl of a sample buffer (EZ Apply, manufactured by ATTO) was added, and the resulting mixture was stirred using a vortex mixer, followed by heating the mixture in boiling water for 10 minutes to perform SDS treatment of the sample.

Figure 3:
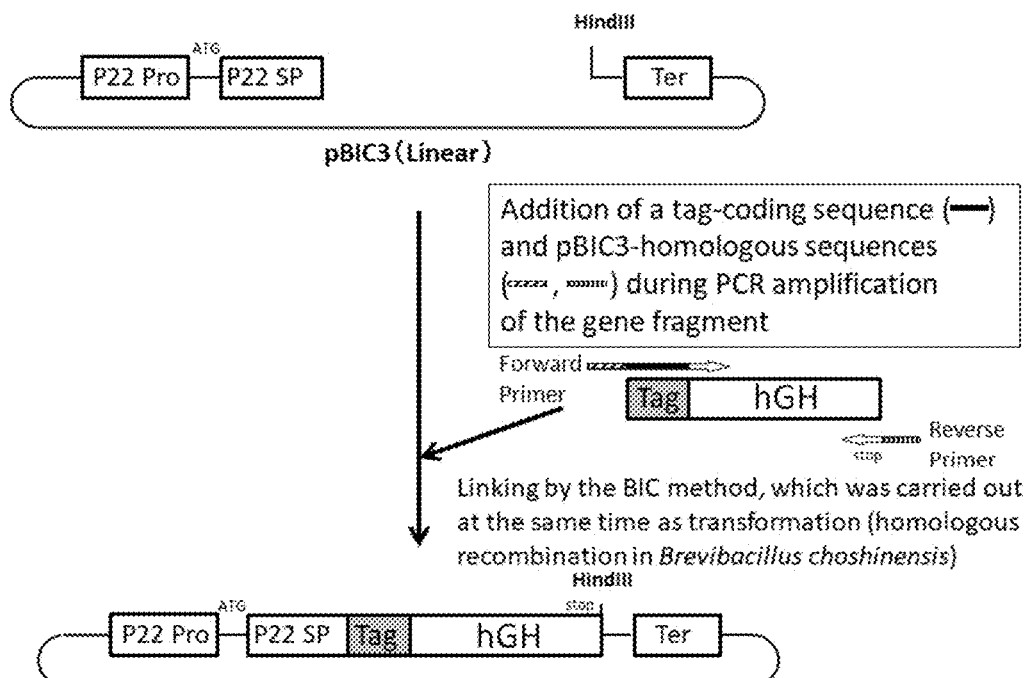
FIG. 3 is a diagram illustrating a procedure for construction of a gene for introduction into Brevibacillus (for expression of hGH).

(9) Construction of Gene Expression Plasmid Encoding Peptide-Tagged hGH for *Brevibacillus*, and Transformation Therewith Plasmid construction and transformation of *Brevibacillus* were carried out using a *Brevibacillus* Expression System—BIC System—(Takara Bio Inc.) (FIG. 3).

First, for addition of various tags to the N- or C-terminus of hGH, or to both the N- and C-termini, PCR was carried out using the combinations of a template plasmid, a forward primer, and a reverse primer shown in Table 3. To the 5'-end of each primer, a sequence homologous to the insertion site in pBIC3 was added. For the PCR, KOD-PLUS-Ver. 2 (Toyobo Co., Ltd.) was used. A reaction liquid in an amount of 50 µl was prepared such that it contained 2 pg/µl template plasmid, 0.3 µM forward primer, 0.3 µM reverse primer, 0.2 mM dNTPs, 1× Buffer for KOD-Plus-Ver. 2, 1.5 mM MgSO$_4$, and 0.02 U/µl KOD-PLUS-Ver. 2. The reaction liquid was heated at 94° C. for 5 minutes, and this was followed by 25 cycles of treatment each composed of heating at 98° C. for 10 seconds, at 60° C. for 30 seconds, and then at 68° C. for 40 seconds. Finally, the reaction liquid was heated at 68° C. for 5 minutes. The resulting amplification fragment was purified with a QIAquick PCR Purification Kit (QIAGEN).

Plasmid construction by homologous recombination, and transformation therewith were carried out as follows. After mixing 100 ng of pBIC3, which is a plasmid for expression in *Brevibacillus* (attached to the kit), with the purified PCR product at a molar ratio of about 1:2, the volume of the resulting mixture was adjusted to 5 µl with sterile water. *Brevibacillus choshinensis* SP3 competent cells (Takara Bio Inc.) were left to stand on a heat block at 37° C. for 30 seconds to allow rapid thawing, and then centrifuged (12,000 rpm, room temperature, 1 minute). After removing the supernatant, the whole amount of a mixture of 5 µl of the above DNA solution and 50 µl of Solution A (attached to the kit) was added, and the pellet of the competent cells was completely suspended by vortexing, followed by leaving the resulting suspension to stand for 5 minutes. After addition of 150 µl of Solution B (PEG solution), the suspension was mixed by vortexing for 10 seconds, and then centrifugation was carried out (5000 rpm, room temperature, 5 minutes), followed by removing the supernatant. After carrying out centrifugation (5000 rpm, room temperature, 30 seconds) again, the supernatant was completely removed. To the resulting pellet, 1 ml of MT medium was added, and the pellet was completely suspended using a micropipette, followed by shake culture at 37° C. at 200 rpm for 1 hour. The culture liquid was plated on an MTNm plate (10 g/L glucose, 10 g/L Phytone peptone, 5 g/L Ehrlich bonito extract, 2 g/L powdered yeast extract S, 10 mg/L FeSO$_4$.7H$_2$O, 10 mg/L MnSO$_4$.4H$_2$O, 1 mg/L ZnSO$_4$.7H$_2$O, 20 mM MgCl$_2$, 1.5% Bacto Agar, 50 µg/mL neomycin, pH 7.0), and static culture was carried out at 37° C. overnight. For the resulting clones, expression of the protein of interest was confirmed by Western analysis of their colonies. For each of the clones for which the expression could be confirmed, its colony was inoculated into TMNm medium (10 g/L glucose, 10 g/L Phytone peptone, 5 g/L Ehrlich bonito extract, 2 g/L powdered yeast extract S, 10 mg/L FeSO$_4$.7H$_2$O, 10 mg/L MnSO$_4$.4H$_2$O, 1 mg/L ZnSO$_4$.7H$_2$O, and 50 µg/mL neomycin, pH 7.0), and culture was carried out at 30° C. at 200 rpm overnight, followed by extraction of plasmid and confirmation of the nucleotide sequence.

(10) Construction of Gene Expression Plasmids Encoding Peptide-Tagged Xylanase or Esterase for *Brevibacillus*, and Transformation Therewith An artificial synthetic DNA (SEQ ID NO:160) encoding xylanase derived from *Bacillus subtilis* (XynA, SEQ ID NO:159) was inserted into the EcoRV recognition site of a pUC19-modified plasmid pUCFa (Fasmac), to obtain plasmid 5. An artificial synthetic DNA (SEQ ID NO:186) encoding esterase derived from *Bacillus subtilis* (EstA, SEQ ID NO:185) was inserted into the EcoRV recognition site of the pUC19-modified plasmid pUCFa (Fasmac), to obtain plasmid 6.

An artificial synthetic DNA (SEQ ID NO:163) encoding an HA tag (SEQ ID NO:161) and a 6× His tag (SEQ ID NO:162) for detection and purification, and a stop codon, was inserted to the NcoI-HindIII site of pNCMO2 (Takara Bio Inc.) such that the HA tag and the 6× His tag were added to the C-terminus of the expressed protein, to prepare plasmid 7 for expression in *Brevibacillus*.

Figure 9:
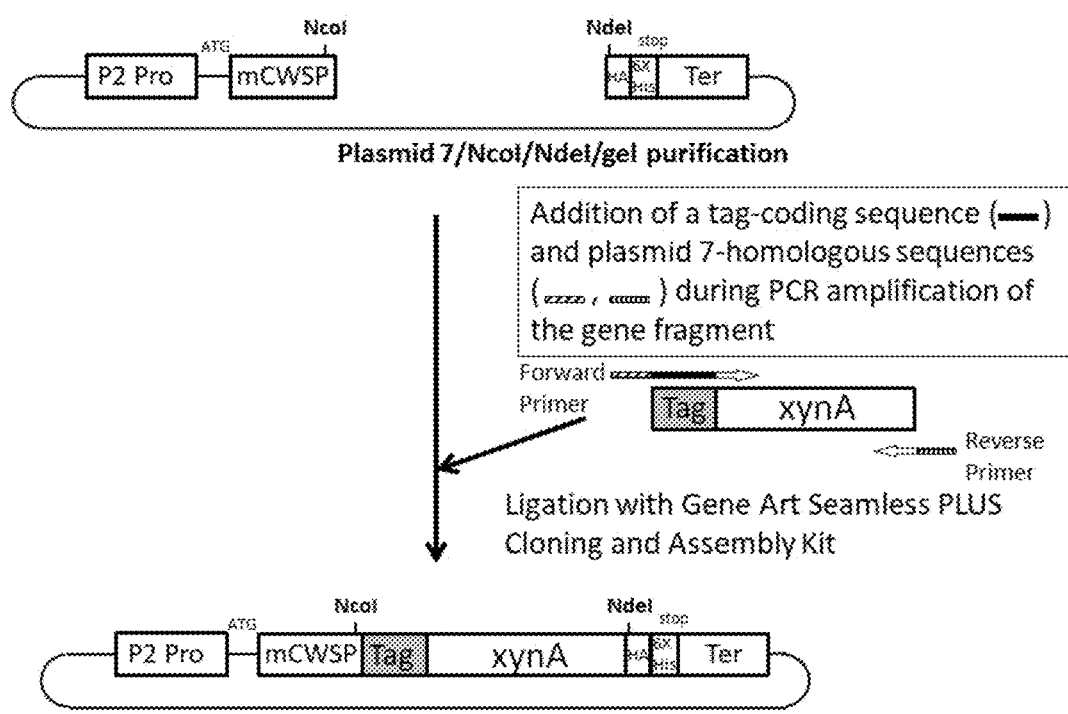
FIG. 9 is a diagram illustrating a procedure for construction of a gene for introduction into Brevibacillus (for expression of xylanase).
Figure 10:
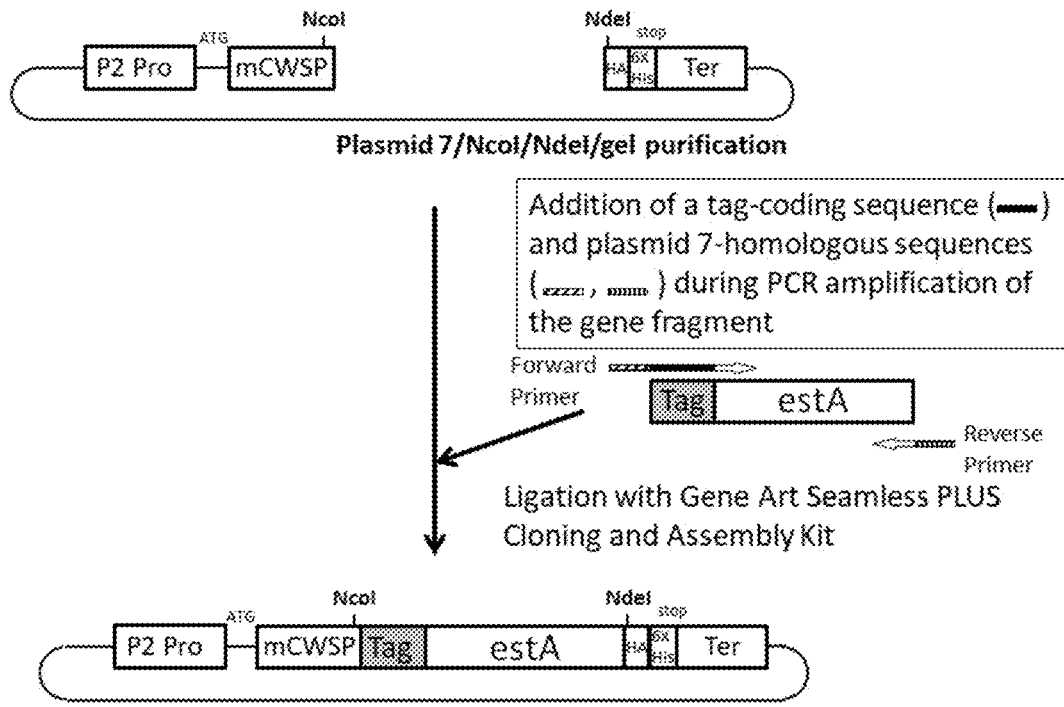
FIG. 10 is a diagram illustrating a procedure for construction of a gene for introduction into Brevibacillus (for expression of esterase).

By the following procedure, plasmids for expression of xylanase or esterase in *Brevibacillus*, having a PX12-20 tag(s) at the N- or C-terminus, or at both the N- and C-termini, were constructed (FIGS. 9 and 10).

First, for addition of various tags to the N- or C-terminus of xylanase or esterase, or to both the N- and C-termini, PCR was carried out using the combinations of a template plasmid, a forward primer, and a reverse primer shown in Table 3. To the 5'-end of each primer, a sequence homologous to plasmid 7 was added. In designing of the forward primer, the two amino acid residues AD were added such that they follow a signal peptide. For the PCR, KOD-PLUS-Ver. 2 (Toyobo Co., Ltd.) was used. A reaction liquid in an amount of 50 µl was prepared such that it contained 2 pg/µl template plasmid, 0.3 µM forward primer, 0.3 reverse primer, 0.2 mM dNTPs, 1× Buffer for KOD-Plus-Ver. 2, 1.5 mM MgSO$_4$, and 0.02 U/µl KOD-PLUS-Ver. 2. The reaction liquid was heated at 94° C. for 5 minutes, and this was followed by 25 cycles of treatment each composed of heating at 98° C. for 10 seconds, at 60° C. for 30 seconds, and then at 68° C. for 40 seconds. Finally, the reaction liquid was heated at 68° C. for 5 minutes. The resulting amplification fragment was purified with a QIAquick PCR Purification Kit. Plasmid 7 was digested with NcoI and NdeI, and then separated by electrophoresis using 0.8% SeaKem GTG Agarose, followed by extraction from the gel using a QIAquick Gel Extraction Kit. With the extracted plasmid 7 in an amount corresponding to about 50 ng, 2 µl of the purified PCR product was mixed, and the liquid volume was adjusted to 5 µl. The resulting mixture was mixed with 5 µl of 2×Enzyme Mix attached to a Gene Art Seamless PLUS Cloning and Assembly Kit, and then left to stand at room temperature for 30 minutes, followed by being left to stand on ice for 5 minutes. With competent cells DH10B T1 SA, 5 µl of the reaction liquid was mixed, and the resulting mixture was left to stand on ice for 30 minutes. The mixture was then warmed at 37° C. for 10 minutes, and left to stand on ice for 2 minutes, followed by addition of 250 µl of SOC thereto and shaking at 37° C. at 200 rpm for 1 hour. Subsequently, 50 µl of the shaken product was applied to 2×YT agar medium supplemented with 100 mg/l ampicillin, and static culture was carried out at 37° C. overnight, to obtain transformed colonies. A colony was transferred to 2×YT liquid medium supplemented with 100 mg/l ampicillin, and shake culture was carried out at 37° C. at 200 rpm overnight, followed by extraction of plasmid. After confirmation of the nucleotide sequence, the plasmid was used for transformation of *Brevibacillus*.

*Brevibacillus choshinensis* SP3 competent cells were left to stand on a heat block at 37° C. for 30 seconds to allow rapid thawing, and then centrifuged (12,000 rpm, room temperature, 1 minute). After removing the supernatant, the whole amount of a mixture of 1 µl of the above plasmid solution and 50 µl of Solution A was added, and the pellet of the competent cells was completely suspended by vortexing, followed by leaving the resulting suspension to stand for 5 minutes. After addition of 150 µl of Solution B, the suspension was mixed by vortexing for 10 seconds, and then centrifugation was carried out (5000 rpm, room temperature, 5 minutes), followed by removing the supernatant. After carrying out centrifugation (5000 rpm, room temperature, 30 seconds) again, the supernatant was completely removed. To the resulting pellet, 1 ml of MT medium as added, and the pellet was completely suspended using a micropipette, followed by shake culture at 37° C. at 200 rpm for 1 hour. The culture liquid was plated on an MTNm plate, and static culture was carried out at 37° C. overnight, to obtain transformed *Brevibacillus*.

(11) Protein Expression Culture of *Brevibacillus*

A single colony of the transformed *Brevibacillus* was smeared on an MTNm plate, and left to stand at 30° C. overnight to perform culture. Subsequently, bacterial cells were scraped with a 1-µl sterile disposable loop from the plate medium after the culture, and then inoculated into 3 ml of TMNm medium placed in a sterile 14-ml polystyrene tube. Preculture was carried out at 30° C. at 200 rpm overnight. In cases of hGH expression, 200 µl of the preculture liquid was inoculated into 3 ml of TMNm medium, and shake culture was carried out at 30° C. at 200 rpm, followed by sampling of the culture liquid containing bacterial cells 48 hours later. In cases of xylanase or esterase expression, 200 µl of the preculture liquid was inoculated into 3 ml of TMNm medium, and shake culture was carried out at 30° C. at 120 rpm, followed by sampling of the culture liquid containing bacterial cells 48 hours later. The culture liquid was aliquoted in 100-µl volumes, and centrifugation (20,000×g, 4° C., 10 minutes) was carried out to separate the bacterial cells from the culture supernatant, followed by storing 50 µl of the culture supernatant and the whole amount of the bacterial cells at −80° C.

(12) Extraction of Protein from *Brevibacillus*

To 50 µl of the cryopreserved culture supernatant, 50 µl of 2× sample buffer (EZ Apply, manufactured by ATTO) was added, and the resulting mixture was stirred using a vortex mixer, followed by heating in boiling water for 10 minutes to perform SDS treatment. To the bacterial cells, 100 µl of 1× sample buffer (2-fold dilution of EZ Apply) was added, and SDS treatment was carried out by the same process.

(13) Construction of Gene Expression Plasmid Encoding Peptide-Tagged hGH for *Pichia* Yeast, and Transformation Therewith An artificial synthetic DNA (SEQ ID NO:169) in which a sequence encoding the extracellular secretion signal peptide for factor α derived from *Saccharomyces cerevisiae* (AFSP, SEQ ID NO:168) and a stop codon sequence are placed downstream of a Kozak sequence was inserted into the BsaI-BsaI site of pJ902-15 (Invivogen), to prepare plasmid 8 for expression in *Pichia* yeast.

Figure 11:
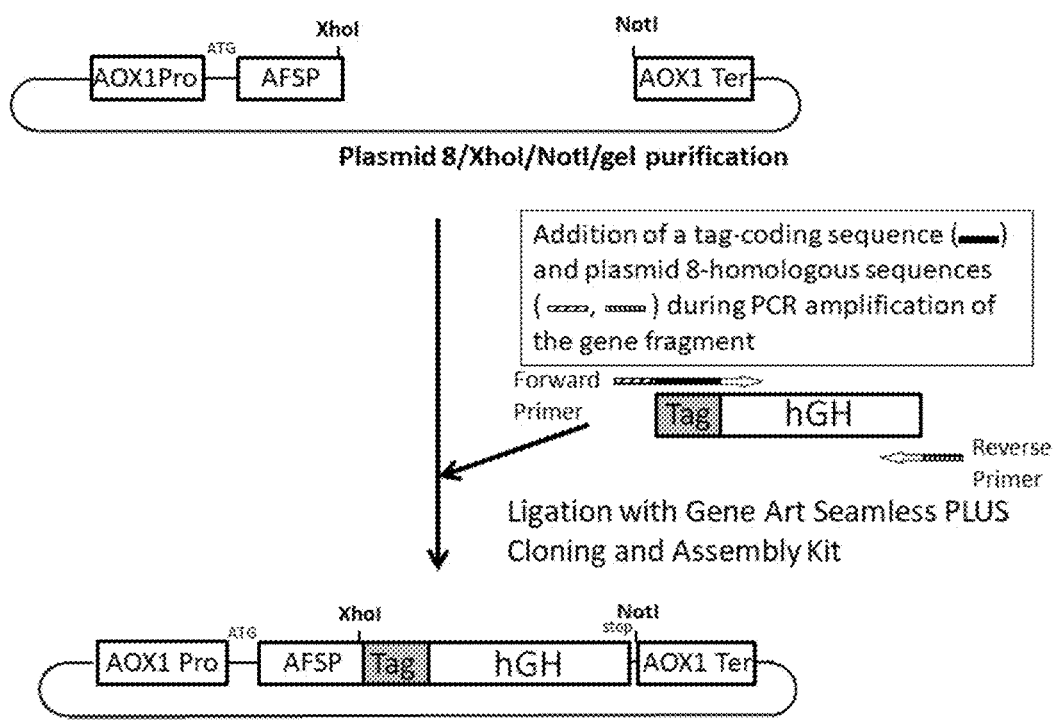
FIG. 11 is a diagram illustrating a procedure for construction of a gene for introduction into Pichia yeast (for expression of hGH).

By the following procedure, plasmids for expression of hGH in *Pichia* yeast, having various tags at the N- or C-terminus, or at both the N- and C-termini, were constructed (FIG. 11).

First, for the addition of a tag(s) to the N- or C-terminus of hGH, or to both the N- and C-termini, PCR was carried out using the combinations of a template plasmid, a forward primer, and a reverse primer shown in Table 3. To the 5'-end of each primer, a sequence homologous to plasmid 8 was added. For the PCR, KOD-PLUS-Ver. 2 (Toyobo Co., Ltd.) was used. A reaction liquid in an amount of 50 µl was prepared such that it contained 2 pg/µl template plasmid, 0.3 µM forward primer, 0.3 µM reverse primer, 0.2 mM dNTPs, 1× Buffer for KOD-Plus-Ver. 2, 1.5 mM $MgSO_4$, and 0.02 U/µl KOD-PLUS-Ver. 2. The reaction liquid was heated at 94° C. for 5 minutes, and this was followed by 25 cycles of treatment each composed of heating at 98° C. for 10 seconds, at 60° C. for 30 seconds, and then at 68° C. for 40 seconds. Finally, the reaction liquid was heated at 68° C. for 5 minutes. The resulting amplification fragment was purified with a QIAquick PCR Purification Kit. Plasmid 8 was digested with XhoI and NotI, and then separated by electrophoresis using 0.8% SeaKem GTG Agarose, followed by extraction from the gel using a QIAquick Gel Extraction Kit. With the extracted plasmid 8 in an amount corresponding to about 50 ng, 2 µl of the purified PCR product was mixed, and the liquid volume was adjusted to 5 µl. The resulting mixture was mixed with 5 µl of 2×Enzyme Mix attached to a Gene Art Seamless PLUS Cloning and Assembly Kit, and then left to stand at room temperature for 30 minutes, followed being left to stand on ice for 5 minutes. With competent cells DH10B T1 SA, 5 µl of the reaction liquid was mixed, and the resulting mixture was left to stand on ice for 30 minutes. The mixture was then warmed at 37° C. for 10 minutes, and left to stand on ice for 2 minutes, followed by addition of 250 µl of SOC thereto and shaking at 37° C. at 200 rpm for 1 hour. Subsequently, 50 µl of the shaken product was applied to 2×YT agar medium supplemented with 100 mg/l ampicillin, and static culture was carried out at 37° C. overnight, to obtain transformed colonies. A colony was transferred to 2× YT liquid medium supplemented with 100 mg/l ampicillin, and shake culture was carried out at 37° C. at 200 rpm overnight, followed by extraction of plasmid and confirmation of the nucleotide sequence. The plasmid was linearized by digestion with SacI, and protein was removed by phenol-chloroform extraction. After ethanol precipitation and drying, the plasmid was dissolved in TE buffer for use in transformation of *Pichia* yeast.

*Pichia* yeast (*Pichia pastoris* PPS-9010) was subjected to shake culture in YPD medium at 30° C. at 200 rpm overnight. To 100 ml of YPD medium placed in an Erlenmeyer flask, the culture liquid was added such that the $OD_{600}$ became 0.2 to 0.4. Shake culture was carried out at 30° C. at 200 rpm until $OD_{600}$ reached 0.8 to 1.0. Centrifugation was carried out at 500× g at room temperature for 5 minutes, and the supernatant was discarded to obtain a cell pellet. To the pellet, 18 ml of ice-cold BEDS solution (10 mM bicine, 3% (v/v) Ethylene glycol, 5% (v/v) Dimethyl sulfoxide, 1 M Sorbitol) and 2 ml of ice-cold 1 M Dithiothreitol were added, and the resulting mixture was suspended, followed by incubation at 30° C. at 100 rpm for 5 minutes. Centrifugation was carried out at 500× g at room temperature for 5 minutes, and the supernatant was discarded to obtain a cell pellet. To the pellet, 2 ml of BEDS solution was added, and the resulting mixture was suspended, followed by aliquoting the suspension in 40-µl volumes to provide competent cells. The competent cells were stored in a deep freezer at −80° C. until use.

The plasmid solution after the linearization in an amount corresponding to about 100 ng of the plasmid was mixed with competent cells thawed on ice, and the resulting mixture was placed in an electroporation cuvette (interelectrode distance, 0.2 cm; BIO-RAD). The cuvette was then left to stand on ice for 2 minutes. The cuvette was set in an electroporation device (MicroPulser, BIO-RAD), and electroporation was carried out under programmed conditions (Pic, 10 µF, 600Ω, 2.0 kV, 1 pulse). Immediately thereafter, 1 ml of YPD medium supplemented with 1 M sorbitol was added to the mixture, and the whole mixture was transferred to a microtube, followed by shaking at 30° C. at 200 rpm for 1 hour. Thereafter, 500 µl of the mixture was applied to YPD plate medium supplemented with 1 M sorbitol, 2% Bacto Agar, and 100 mg/L Zeocine (Invivogen), and static culture was carried out at 30° C. for 2 to 3 days, to obtain transformed colonies.

(14) Protein Expression Culture of *Pichia* Yeast

A single colony after the transformation was applied to YPD plate medium supplemented with 1 M Sorbitol, 2% Bacto Agar, and 100 mg/L Zeocine, and static culture was carried out at 30° C. for 24 hours. Subsequently, cells were scraped with a 1-µl sterile disposable loop from the plate medium after the culture, and then inoculated into 3 ml of BMGY medium (1% Bacto Yeast Extract, 2% Bacto peptone, 0.1 M potassium phosphate buffer (pH 6.0), 1.34% Yeast nitrogen base with ammonium sulfate without amino acids, 0.4 mg/L Biotin, 1% Glycerol) placed in a sterile 14-ml tube, followed by performing shake culture at 30° C. at 200 rpm until $OD_{600}$ reached 2 to 6. The culture in the amount required for $OD_{600}$ to become 1 by resuspension in 3 ml of a medium was taken into a sterile 1.5-ml Eppendorf tube, and then centrifugation was carried out at 3000× g at 20° C. for 5 minutes. After removing the supernatant, the precipitate was suspended in 1 ml of BMMY medium (1% Bacto Yeast Extract, 2% Bacto peptone, 0.1 M potassium phosphate buffer (pH 6.0), 1.34% Yeast nitrogen base with ammonium sulfate without amino acids, 0.4 mg/L Biotin, 0.5% Methanol), and the whole amount of the resulting suspension was mixed with 2 ml of BMMY medium preliminarily provided in a sterile 14-ml tube, followed by performing shake culture at 30° C. at 200 rpm for 72 hours. After completion of the culture, 100 µl of the culture liquid was taken into a microtube, and centrifugation was carried out at 15,000×g at 4° C. for 10 minutes, followed by taking 50 µl of the supernatant into another tube to obtain a culture supernatant. The remaining supernatant was removed to obtain a yeast cell pellet. The culture supernatant and the yeast cell pellet were frozen in liquid nitrogen, and then stored in a deep freezer at −80° C.

(15) Extraction of Protein from *Pichia* Yeast

To 50 µl of the cryopreserved culture supernatant, 50 µl of 2× sample buffer (EZ Apply, manufactured by ATTO) was added, and the resulting mixture was stirred using a vortex mixer, followed by heating in boiling water for 10 minutes to perform SDS treatment.

The yeast cell pellet was suspended in 100 µl of an ice-cold suspension buffer (1×PBS (BIO-RAD), 1× complete-EDTA free (Roche)), and the whole amount of the resulting suspension was added to 80 µl of glass beads (diameter, 0.5 mm; acid-treated; Sigma) placed in a microtube, followed by homogenization by shaking using Tissue-Lyzer II (QIAGEN) at 30 Hz for 4 minutes. After taking 30 µl of the homogenate, 30 µl of 2× sample buffer (EZ Apply, manufactured by ATTO) was added thereto. The resulting mixture was stirred using a vortex mixer, and then heated in boiling water for 10 minutes to perform SDS treatment.

(16) Western Analysis

As reference materials for protein quantification, standard samples of hGH and IFNβ were used. For quantification of xylanase, an HA sequence was added to Stx2eB to provide a standard sample. Each standard sample was serially 2-fold diluted with a sample buffer (EZ Apply, manufactured by ATTO) to prepare a dilution series to be used as standards.

For electrophoresis (SDS-PAGE) of protein, an electrophoresis tank (Criterion cell, BIO RAD) and Criterion TGX-gel (BIO RAD) were used. In the electrophoresis tank, an electrophoresis buffer (Tris/Glycine/SDS Buffer, BIO RAD) was placed, and 4 µl of each SDS-treated sample was applied to each well, followed by performing electrophoresis at a constant voltage of 200 V for 40 minutes.

The gel after the electrophoresis was subjected to blotting by Trans-Blot Turbo (BIO RAD) using a Trans-Blot Transfer Pack (BIO RAD).

The membrane after the blotting was immersed in a blocking solution (TBS system, pH 7.2; Nacalai Tesque, Inc.), and shaken at room temperature for 1 hour or left to stand at 4° C. for 16 hours. Thereafter, the membrane was subjected to three times of washing by shaking in TBS-T (137 mM sodium chloride, 2.68 mM potassium chloride, 1% polyoxyethylene sorbitan monolaurate, 25 mM Tris-HCl, pH 7.4) at room temperature for 5 minutes. For detection of hGH, an antiserum Rabbit-monoclonal Anti-Growth Hormone antibody [EPR11047(B)] (abcam) was used after 3000-fold dilution with TBS-T. For detection of IFNβ, an antiserum Mouse-monoclonal Anti-Human IFNβ antibody (R&D Systems) was used after 1,000-fold dilution with TBS-T. For detection of xylanase and esterase, an antiserum Rat-monoclonal Anti-HA antibody (Roche) was used after 6,000-fold dilution with TBS-T. The membrane was immersed in the antibody dilution, and shaken at room temperature for 1 hour to allow antigen-antibody reaction, followed by three times of washing by shaking in TBS-T at room temperature for 5 minutes. As a secondary antibody, an Anti-Rabbit IgG, AP-linked Antibody (Cell Signaling TECHNOLOGY) diluted 2000-fold with TBS-T was used for detection of hGH, or an Anti-Mouse IgG; AP-linked Antibody (Cell Signaling TECHNOLOGY) was used for detection of IFNβ. For detection of xylanase and esterase, an Anti-Rat IgG, AP-linked Antibody (EDM Millipore Corp.) diluted 6000-fold with TBS-T was used.

The membrane was immersed in the secondary antibody dilution, and shaken at room temperature for 1 hour to allow antigen-antibody reaction, followed by three times of washing by shaking in TBS-T at room temperature for 5 minutes. Chromogenic reaction with alkaline phosphatase was carried out by immersing the membrane in a coloring solution (0.1 M sodium chloride, 5 mM magnesium chloride, 0.33 mg/ml nitroblue tetrazolium, 0.33 mg/ml 5-bromo-4-chloro-3-indolyl-phosphate, 0.1 M Tris-HCl, pH 9.5), and shaking the membrane at room temperature for 15 minutes. The membrane was washed with distilled water, and then dried at normal temperature.

From the membrane after the coloring, an image was obtained using a scanner (PM-A900, Epson) at a resolution of 600 dpi, and quantification of hGH or IFNβ protein was carried out using image analysis software (CS Analyzer ver. 3.0, Atto Corporation).

(17) Evaluation of Effect on Improvement of Protein Expression Level in Insect Cells As the protein to which the peptide tag was added, green fluorescent protein derived from *Aequorea victoria* (GFP; amino acid sequence, SEQ ID NO:175; DNA nucleotide sequence, SEQ ID NO:176) was used. PCR reaction was carried out using combinations of a forward primer (pENTR1A-1 (SEQ ID NO:177), for addition of no tag; pENTR1A-2 (SEQ ID NO:178), for PG12 tag; pENTR1A-3 (SEQ ID NO:179), for PX12-20 tag; pENTR1A-4 (SEQ ID NO:180), for PX12-20v7 tag) and a reverse primer (pENTR1A-Flag-GFP (SEQ ID NO:181)) such that various peptide tags were added to the N-terminal side of the GFP protein and a Flag tag was added to the C-terminal side, to prepare DNA fragments for cloning. Each prepared DNA fragment was cloned into pENTR 1A (ThermoFisher Scientific) to construct a plasmid having the DNA fragment encoding each peptide tag-GFP-Flag tag. Based on this plasmid, LR reaction was used to insert the DNA encoding the peptide tag-GFP-Flag tag into pFastbac (ThermoFisher Scientific), which is a donor vector. The donor vector was introduced into E. coli DH10bac (ThermoFisher Scientific) to allow its transposition into the lacZ region of a bacmid vector, to prepare a recombinant bacmid. The recombinant bacmid DNA containing the DNA encoding the peptide tag-GFP-Flag tag was introduced into BmN cells derived from silkworm, to prepare a baculovirus. The operation of adding a solution of the obtained baculovirus to a medium for BmN cells to prepare a baculovirus solution again was repeated three times, to prepare a baculovirus solution with a sufficiently increased baculovirus concentration. To 1.8 ml of IPL41-10% FCS medium containing 5.0×10⁵ BmN cells, 200 µl of the baculovirus solution was added, and, 36 hours later, the cells were detached by pipetting, followed by collecting the culture liquid and counting the cell number. Thereafter, the culture supernatant was separated from the cell fraction by centrifugation operation. The collected cell fraction was suspended in 200 µl of the solution of 20 mM Tris-HCl (pH7.4), 20 mM NaCl, and 3 mM MgCl₂. The resulting suspension was then subjected to ultrasonic treatment and centrifugation operation, followed by collecting the supernatant. The collected cell homogenate supernatant was added to the culture supernatant to provide an analysis sample. SDS-PAGE was carried out for 9 µl of the analysis sample containing the peptide tag-GFP-Flag tag, and the peptide tag-GFP-Flag tag protein was detected using ImmunoStar Zeta (Wako Pure Chemical Industries, Ltd.) with an anti-Flag antibody (Sigma Aldrich) as a primary antibody and an anti-mouse IgG HRP-labeled antibody (GE healthcare) as a secondary antibody. By comparison of the values calculated by dividing the band intensity of each peptide tag-GFP-Flag tag protein by the number of cells, the effect of each peptide tag on improvement of the protein expression level was determined.

(18) Evaluation of Effect on Improvement of Protein Expression Level in Mammalian Cells As the protein to which the peptide tag was added, green fluorescent protein derived from Aequorea victoria (GFP; amino acid sequence, SEQ ID NO:175; DNA nucleotide sequence, SEQ ID NO:176) was used. PCR reaction was carried out using combinations of a forward primer (pENTR1A-1 (SEQ ID NO:177), for addition of no tag; pENTR1A-2 (SEQ ID NO:178), for PG12 tag; pENTR1A-3 (SEQ ID NO:179), for PX12-20 tag) and a reverse primer (pENTR1A-Flag-GFP (SEQ ID NO:181)) such that various peptide tags were added to the N-terminal side of the GFP protein and a Flag tag was added to the C-terminal side, to prepare DNA fragments for cloning. Each prepared DNA fragment was cloned into pENTR 1A (ThermoFisher Scientific) to construct a plasmid having the DNA fragment encoding each peptide tag-GFP-Flag tag. Based on this plasmid, LR reaction was used to insert the DNA encoding the peptide tag-GFP-Flag tag into pAd/CMV/v5-DEST adenovirus vector (ThermoFisher Scientific). Each resulting vector was introduced into HEK293A cells to prepare an adenovirus solution. The operation of inoculating the obtained adenovirus solution to HEK293A cells to prepare an adenovirus solution again was repeated four times, to prepare an adenovirus solution with a sufficiently increased adenovirus concentration. To 2.5×10⁵ A549 cells in 1.2 ml of DMEM high glucose-10% FCS medium, 200 µl of this adenovirus solution was added, and, 84 hours later, the cells were detached by trypsin treatment (37° C., 10 minutes), followed by collecting the culture liquid and counting the cell number. Thereafter, the culture supernatant was separated from the cell fraction by centrifugation operation. The collected cell fraction was suspended in 200 µl of the solution of 20 mM Tris-HCl (pH7.4), 20 mM NaCl, and 3 mM MgCl₂. The resulting suspension was then subjected to ultrasonic treatment and centrifugation operation, followed by collecting the supernatant and adding the supernatant to the culture supernatant. The fluorescence intensity was measured at an excitation wavelength of 395 nm and a measurement wavelength of 509 nm. By comparison of the values calculated by dividing the fluorescence intensity of each peptide tag-GFP-Flag tag protein by the number of cells, the effect of each peptide tag on improvement of the protein expression level was determined.

<Results>

Figure 4:
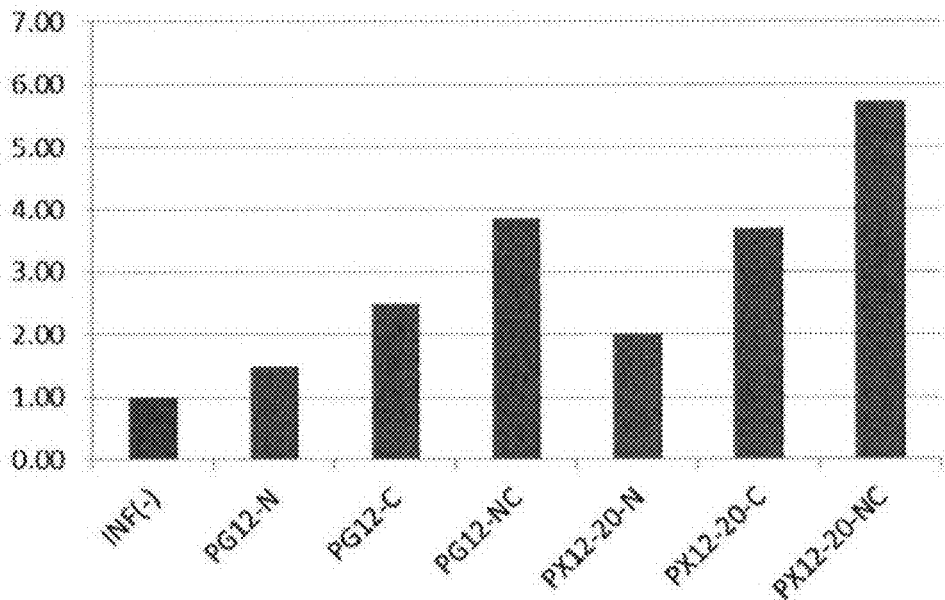
FIG. 4 is a diagram showing the expression levels of IFNβ having various tags in Saccharomyces yeast. Relative values with respect to the expression level of non-tagged IFNβ, which is taken as 1, are shown.

(1) Improvement of Protein Expression Levels in Yeast by Addition of Various Peptide Tags The prepared recombinant yeast was cultured under predetermined conditions, and hGH or IFNβ was extracted under predetermined conditions, followed by measuring the expression level of the protein of interest by Western analysis. As a result, as shown in FIG. 4, the protein expression level was higher in the cases where PX12-20 (SEQ ID NO:25), which was prepared by changing three Ss in the PG12 sequence (SEQ ID NO:22) to Ks, was added to IFNβ, than in the cases where PG12 was added to IFNβ. The effect of the PX12-20 tag was higher in the case of addition to the C-terminus than in the case of addition to the N-terminus, and even higher in the case of addition to both the N-terminus and the C-terminus.

Figure 5:
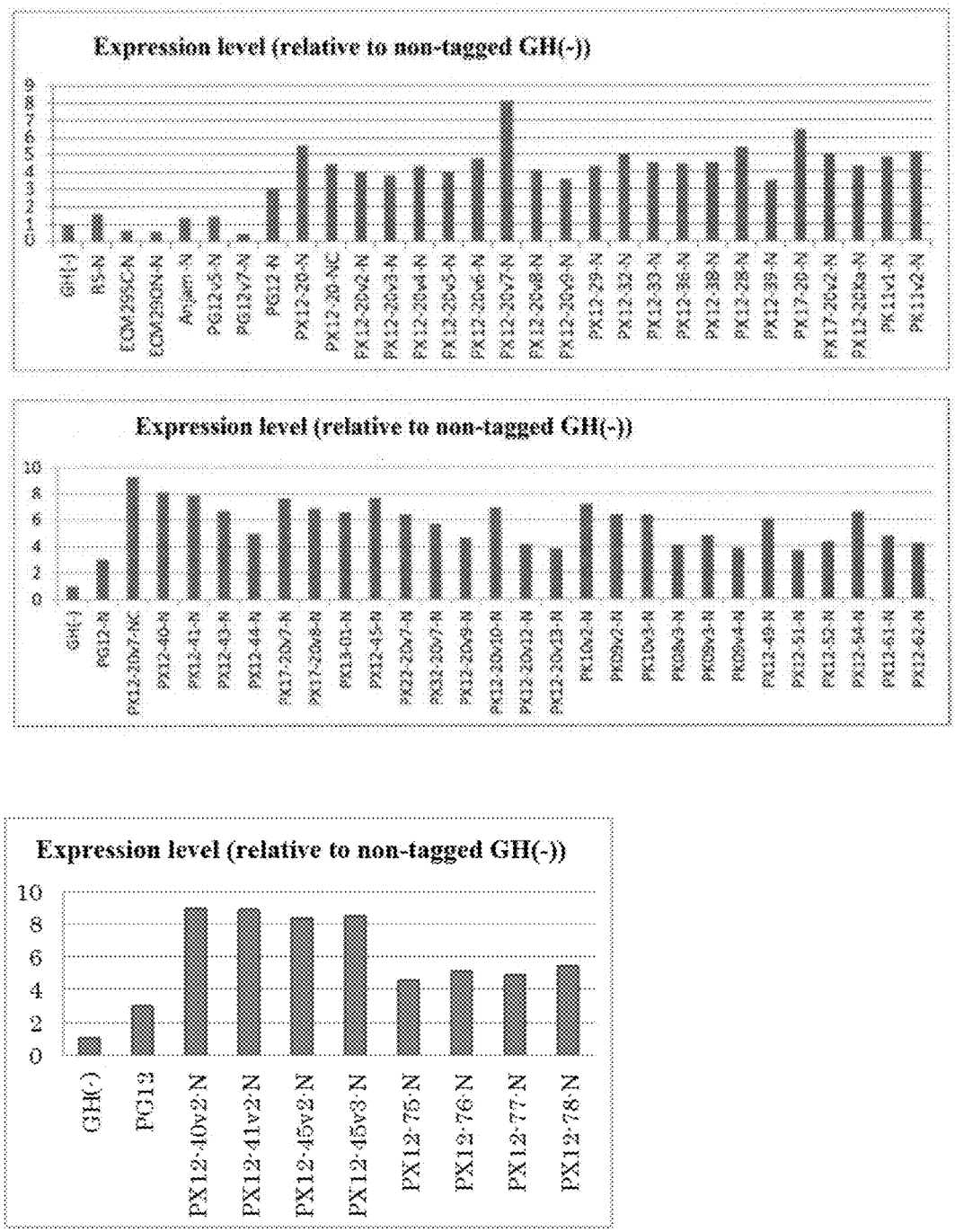
FIG. 5 is a diagram showing the expression levels of hGH having various tags in Saccharomyces yeast. Relative values with respect to the expression level of non-tagged hGH, which is taken as 1, are shown.

As shown in FIG. 5, as a result of preparation of peptide tags by various modifications of the sequence of PG12 or PG17, and investigation of the influences of such modifications on expression of hGH, it was found that not only K, but also L, N, Q, and R are effective for increasing the expression when they are used as amino acids for substitution of S and/or G in PG12. Further, addition of a protease recognition sequence to each tag having a modified amino acid sequence still allowed maintenance of the high-expression effect.

Figure 6:
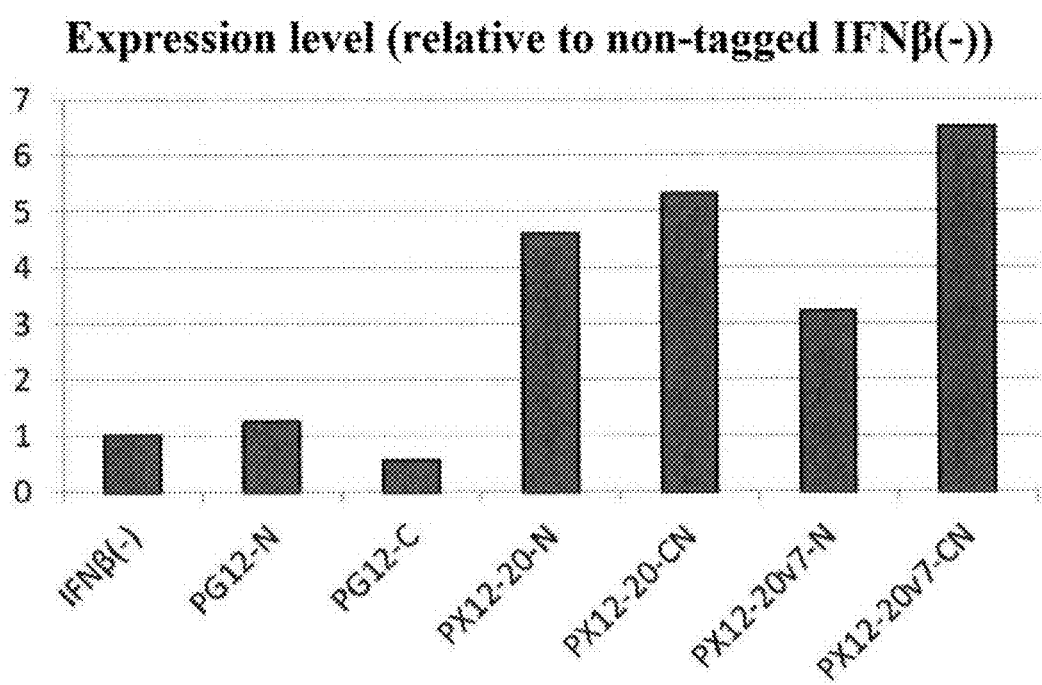
FIG. 6 is a diagram showing the expression levels of IFNβ having various tags in E. coli. Relative values with respect to the expression level of non-tagged IFNβ, which is taken as 1, are shown.
Figure 7:
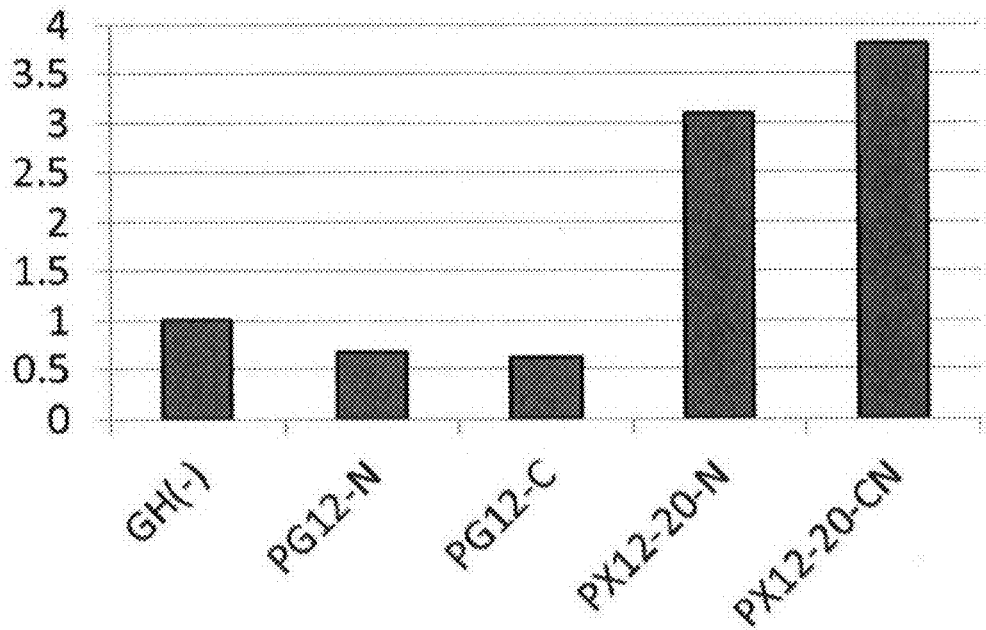
FIG. 7 is a diagram showing the expression levels of hGH having various tags in E. coli. Relative values with respect to the expression level of non-tagged hGH, which is taken as 1, are shown.

(2) Improvement of Protein Expression Levels in E. coli by Addition of Various Peptide Tags The prepared recombinant E. coli was cultured under predetermined conditions, and hGH or IFNβ was extracted under predetermined conditions, followed by measuring the expression level of the protein of interest by Western analysis. As a result, as shown in FIG. 6, the protein expression level was higher in the cases where PX12-20 (SEQ ID NO:25) or PX12-20v7 (SEQ ID NO:38) was added to IFNβ than in the cases where PG12 was added to IFNβ. The effect of PX12-20 or PX12-20v7 was even higher in the case of addition to both the N-terminus and the C-terminus than in the case of addition to only the N-terminus. As shown in FIG. 7, the effect of PX12-20 was also exerted on hGH.

Figure 8:
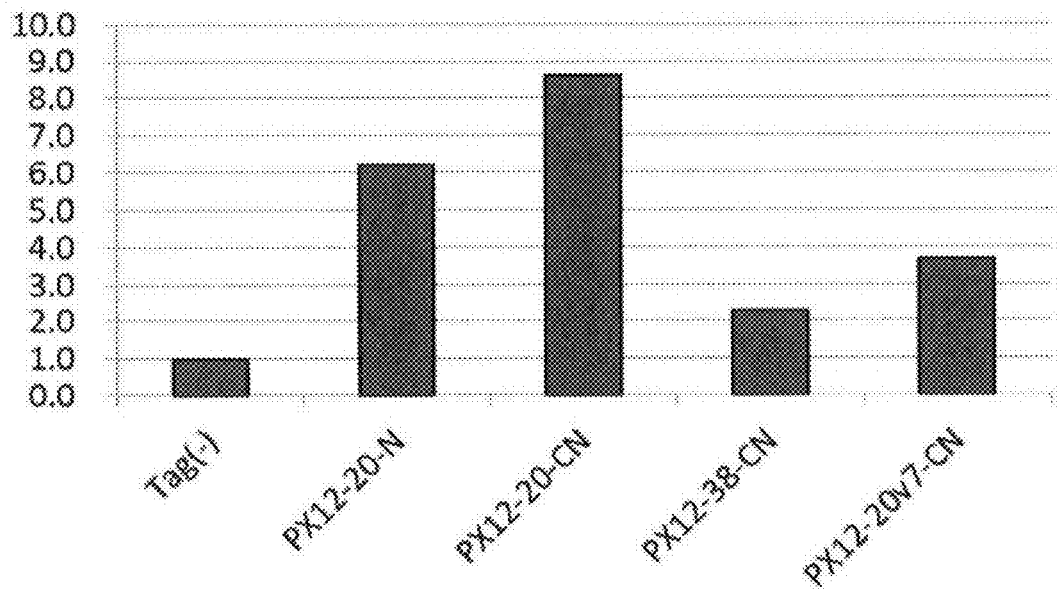
FIG. 8 is a diagram showing the expression levels of hGH having various tags in Brevibacillus. Relative values with respect to the expression level of non-tagged hGH, which is taken as 1, are shown.

(3) Improvement of Protein Expression Level in Brevibacillus by Addition of Various Peptide Tags The prepared recombinant Brevibacillus was cultured under predetermined conditions, and hGH was extracted under predetermined conditions, followed by measuring the expression level of the protein of interest by Western analysis. As a result, as shown in FIG. 8, the expression level of hGH increased in the cases where PX12-20 (SEQ ID NO:25), PX12-38 (SEQ ID NO:52), or PX12-20v7 (SEQ ID NO:38) was added to hGH.

Figure 12:
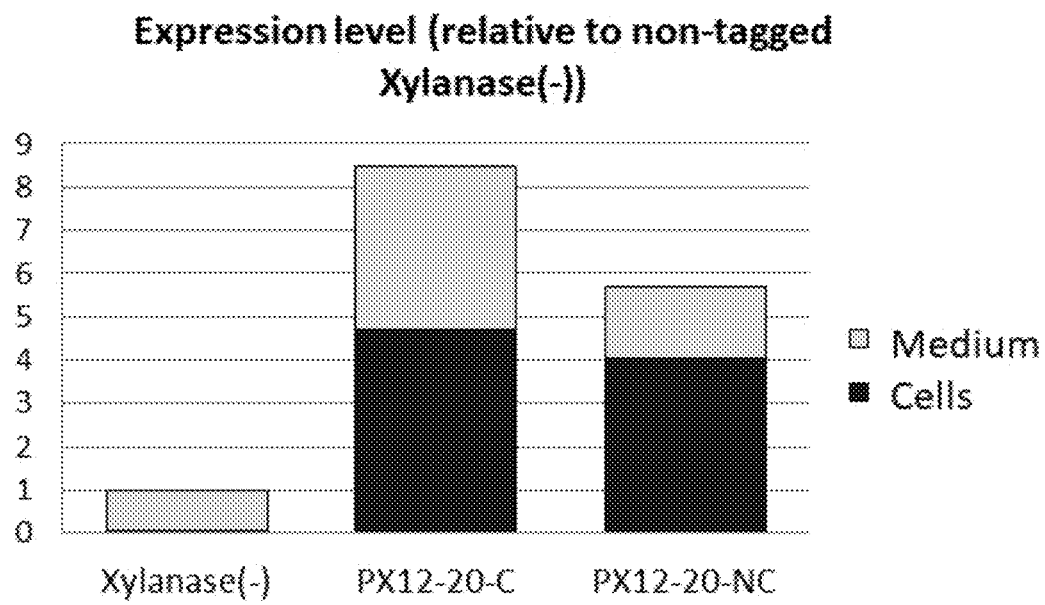
FIG. 12 is a diagram showing the expression levels of xylanase having various tags in Brevibacillus. Relative values with respect to the expression level of non-tagged xylanase, which is taken as 1, are shown.

The prepared recombinant *Brevibacillus* was cultured under predetermined conditions, and xylanase was extracted under predetermined conditions, followed by measuring the expression level of the protein of interest by Western analysis. As a result, as shown in FIG. 12, the expression level of xylanase increased in the cases where PX12-20 (SEQ ID NO:25) was added to the C-terminus or to both the N-terminus and the C-terminus.

Figure 13:
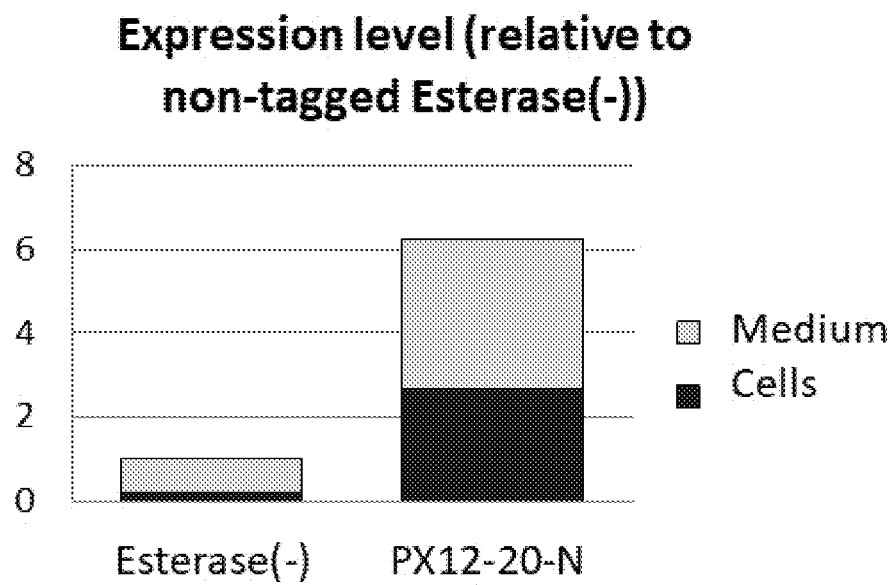
FIG. 13 is a diagram showing the expression levels of esterase having various tags in Brevibacillus. Relative values with respect to the expression level of non-tagged esterase, which is taken as 1, are shown.

The prepared recombinant *Brevibacillus* was cultured under predetermined conditions, and esterase was extracted under predetermined conditions, followed by measuring the expression level of the protein of interest by Western analysis. As a result, as shown in FIG. 13, the expression level of esterase increased in the case where PX12-20 (SEQ ID NO:25) was added to the N-terminus.

Figure 14:
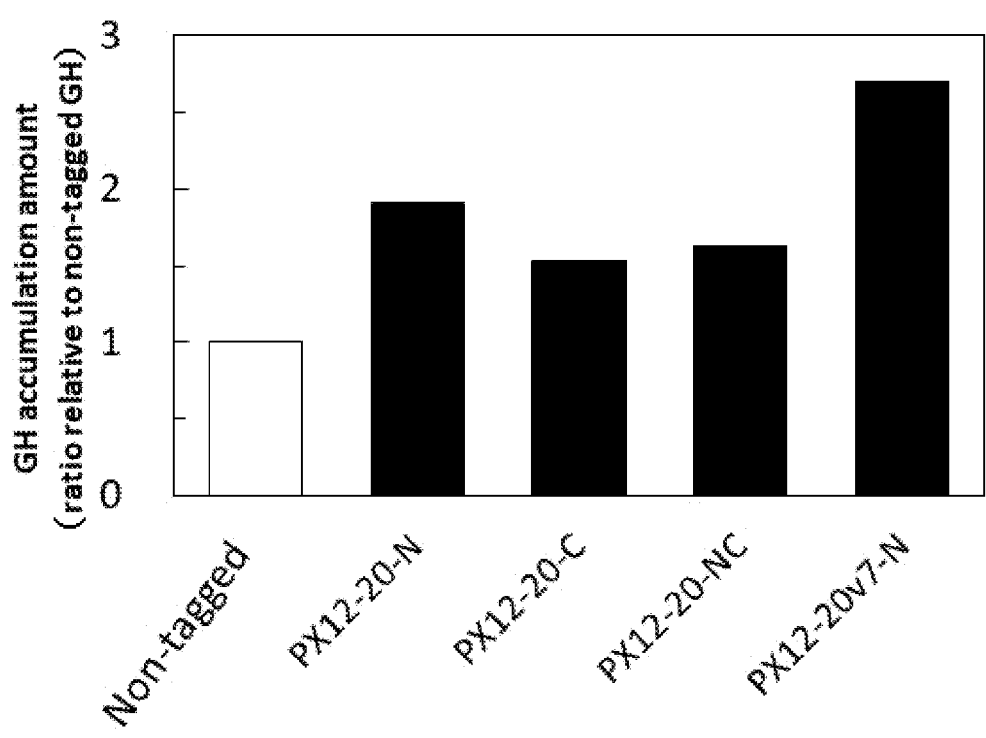
FIG. 14 is a diagram showing the expression levels of hGH having various tags in Pichia yeast. Relative values with respect to the expression level of non-tagged hGH, which is taken as 1, are shown.

(4) Improvement of Protein Expression in *Pichia* Yeast by Addition of Various Peptide Tags The prepared recombinant *Pichia* yeast was cultured under predetermined conditions, and hGH was extracted under predetermined conditions, followed by measuring the expression level of the protein of interest by Western analysis. As a result, as shown in FIG. 14, the expression level of hGH increased in the cases where PX12-20 (SEQ ID NO:25) or PX12-20v7 (SEQ ID NO:38) was added to hGH.

TABLE 1

Amino acid sequence of each peptide tag

| Tag | Amino acid sequence of Tag |
|---|---|
| GH(−) | — |
| RS-N | RS |
| ECM29SC-N | RSPESGAGSPRS (SEQ ID NO: 12) |
| ECM29ON-N | LGSESDDSEGSIKQ (SEQ ID NO: 14) |
| Anjam-N | GPGPSRGSDIKLTS (SEQ ID NO: 16) |
| PG12v5-N | RWPGSGPGWPRS (SEQ ID NO: 18) |
| PG12v7-N | PSGPSGPGSPTS (SEQ ID NO: 20) |
| PG12-N | RSPGSGPGSPRS (SEQ ID NO: 22) |
| PG12-C | RSPGSGPGSPRS (SEQ ID NO: 22) |
| PG12-NC | RSPGSGPGSPRS (SEQ ID NO: 22)-IFNβ-RSPGSGPGSPRS (SEQ ID NO: 22) |
| PX12-20-N | RKPGKGPGKPRS (SEQ ID NO: 25) |
| PX12-20-C | RKPGKGPGKPRS (SEQ ID NO: 25) |
| PX12-20-NC | RKPGKGPGKPRS (SEQ ID NO: 25)-hGH/IFNβ-RKPGKGPGKPRS (SEQ ID NO: 25) |
| PX12-20v2-N | RKPGKGPGKPRK (SEQ ID NO: 28) |
| PX12-20v3-N | RKPGKGPGKPTS (SEQ ID NO: 30) |
| PX12-20v4-N | RKPGKGPGKPLS (SEQ ID NO: 32) |
| PX12-20v5-N | TKPGKGPGKPTS (SEQ ID NO: 34) |
| PX12-20v6-N | KKPGKGPGKPKK (SEQ ID NO: 36) |
| PX12-20v7-N | RKPKKKPKKPRS (SEQ ID NO: 38) |
| PX12-20v8-N | RKPGKGPGSPRS (SEQ ID NO: 40) |

TABLE 1-continued

Amino acid sequence of each peptide tag

| Tag | Amino acid sequence of Tag |
|---|---|
| PX12-20v9-N | RKPGSGPGKPRS (SEQ ID NO: 42) |
| PX12-29-N | RKPGKPKGKPTS (SEQ ID NO: 44) |
| PX12-32-N | RQPGQGPGQPRS (SEQ ID NO: 46) |
| PX12-33-N | RNPGNGPGNPRS (SEQ ID NO: 48) |
| PX12-36-N | RLPGLGPGLPRS (SEQ ID NO: 50) |
| PX12-38-N | RRPGRGPGRPRS (SEQ ID NO: 52) |
| PX12-28-N | RSPKSKPKSPRS (SEQ ID NO: 54) |
| PX12-39-N | RSPGSGPGSPTS (SEQ ID NO: 56) |
| PX17-20-N | RKPGKGPGKPRKPGKRS (SEQ ID NO: 58) |
| PX17-20v2-N | RKPGKGPGKPRSPGSRS (SEQ ID NO: 60) |
| PX12-20Xa-N | RKPGKGPGKPRSIEGR (SEQ ID NO: 62) |
| PK11v1-N | RKPGKGPGKPR (SEQ ID NO: 64) |
| PK11v2-N | KPGKGPGKPRS (SEQ ID NO: 66) |
| PX12-20v7-NC | RKPKKKPKKPRS (SEQ ID NO: 38)-hGH/IFNβ-RKPKKKPKKPRS (SEQ ID NO: 38) |
| PX12-40-N | RRPRRRPRRPRS (SEQ ID NO: 92) |
| PX12-41-N | RKPKRKPKRPRS (SEQ ID NO: 94) |
| PX12-43-N | RKPRKRPRKPRS (SEQ ID NO: 96) |
| PX12-44-N | KKPKKKPKKPKK (SEQ ID NO: 98) |
| PX17-20v7-N | RKPKKKPKKPRKPKKRS (SEQ ID NO: 100) |
| PX17-20v8-N | RKPKKKPKKPKKPKKRS (SEQ ID NO: 102) |
| PX13-01-N | RKPKKKPKKKPRS (SEQ ID NO: 104) |
| PX12-45-N | RKPKKPKKPKRS (SEQ ID NO: 106) |
| PX22-20v7-N | RKPKKKPKKPRKPKKKPKKPRS (SEQ ID NO: 108) |
| PX32-20v7-N | RKPKKKPKKPRKPKKKPKKPRKPKKKPKKPRS (SEQ ID NO: 110) |
| PX12-20v9-N | RKPKSKPKKPRS (SEQ ID NO: 112) |
| PX12-20v10-N | RKPKGKPKKPRS (SEQ ID NO: 114) |
| PX12-20v12-N | RKPGKKPGKPRS (SEQ ID NO: 116) |
| PX12-20v13-N | RKPGGKPGKPRS (SEQ ID NO: 118) |
| PK10v2-N | RKPKKKPRKP (SEQ ID NO: 120) |
| PK09v2-N | RKPKKKPRK (SEQ ID NO: 122) |
| PK10v3-N | RPKKKPKKPR (SEQ ID NO: 124) |
| PK08v3-N | RPKRKPRK (SEQ ID NO: 126) |
| PK09v3-N | PRKPRKPRK (SEQ ID NO: 128) |
| PK09v4-N | PKRPKRPKR (SEQ ID NO: 130) |
| PX12-49-N | RKPKLKPKKPRS (SEQ ID NO: 132) |
| PX12-51-N | RRPLRLPLRPRS (SEQ ID NO: 134) |
| PX12-52-N | RQPKQKPKQPRS (SEQ ID NO: 136) |

TABLE 1-continued

Amino acid sequence of each peptide tag

| Tag | Amino acid sequence of Tag |
|---|---|
| PX12-54-N | RQPKKKPKQPRS(SEQ ID NO: 138) |
| PX12-61-N | RHPKHKPKHPRS(SEQ ID NO: 140) |
| PX12-62-N | RNPKNKPKNPRS(SEQ ID NO: 142) |
| PX12-40v2-N | RRPRRPRRPRRS(SEQ ID NO: 143) |
| PX12-41v2-N | RRPKRPKRPKRS(SEQ ID NO: 145) |
| PX12-45v2-N | RKPKKPKKPRS(SEQ ID NO: 147) |
| PX12-45v3-N | RKPKKPKKPKKRS(SEQ ID NO: 149) |
| PX12-75-N | RKPGSKPGKPRS(SEQ ID NO: 151) |
| PX12-76-N | RKPQQKPQKPRS(SEQ ID NO: 153) |
| PX12-77-N | RRPGSRPGRPRS(SEQ ID NO: 155) |
| PX12-78-N | RKPKPKPKPRS(SEQ ID NO: 157) |

TABLE 2

Template plasmids and primers used in PCR amplification of hGH gene or IFN beta gene added with a peptide tag coding sequence

| PCR amplification fragment | Added peptide tag sequence N-terminus | Added peptide tag sequence C-terminus | Template Plasmid | Forward Primer |
|---|---|---|---|---|
| GH-(-) | — | — | Plasmid 1 | 6XHN-hGHF(SEQ ID NO: 8) |
| GH-RS-N | RS | — | Plasmid 1 | 6XHN-RS-hGHF(SEQ ID NO: 11) |
| GH-ECM29SC-N | SEQ ID NO: 12 | — | Plasmid 1 | 6XHN-ECM29SC-hGHF(SEQ ID NO: 13) |
| GH-ECM29ON-N | SEQ ID NO: 14 | — | Plasmid 1 | 6XHN-ECM29ON-hGHF(SEQ ID NO: 15) |
| GH-Anjam-N | SEQ ID NO: 16 | — | Plasmid 1 | 6XHN-Anjam-hGHF(SEQ ID NO: 17) |
| GH-PG12v5-N | SEQ ID NO: 18 | — | Plasmid 1 | 6XHN-PG12v5-hGHF(SEQ ID NO: 19) |
| GH-PG12v7-N | SEQ ID NO: 20 | — | Plasmid 1 | 6XHN-PG12v7-hGHF(SEQ ID NO: 21) |
| GH-PG12-N | SEQ ID NO: 22 | — | Plasmid 1 | 6XHN-PG12-hGHF(SEQ ID NO: 23) |
| GH-PG12-C | — | SEQ ID NO: 22 | Plasmid 1 | 6XHN-hGHF(SEQ ID NO: 8) |
| GH-PG12-NC | SEQ ID NO: 22 | SEQ ID NO: 22 | Plasmid 1 | 6XHN-PG12-hGHF(SEQ ID NO: 23) |
| GH-PX12-20-N | SEQ ID NO: 25 | — | Plasmid 1 | 6XHN-PX12-20-hGHF(SEQ ID NO: 26) |
| GH-PX12-20-C | — | SEQ ID NO: 25 | Plasmid 1 | 6XHN-hGHF(SEQ ID NO: 8) |
| GH-PX12-20-NC | SEQ ID NO: 25 | SEQ ID NO: 25 | Plasmid 1 | 6XHN-PX12-20-hGHF(SEQ ID NO: 26) |
| GH-PX12-20v2-N | SEQ ID NO: 28 | — | Plasmid 1 | 6XHN-PX12-20v2-hGHF(SEQ ID NO: 29) |
| GH-PX12-20v3-N | SEQ ID NO: 30 | — | Plasmid 1 | 6XHN-PX12-20v3-hGHF(SEQ ID NO: 31) |
| GH-PX12-20v4-N | SEQ ID NO: 32 | — | Plasmid 1 | 6XHN-PX12-20v4-hGHF(SEQ ID NO: 33) |
| GH-PX12-20v5-N | SEQ ID NO: 34 | — | Plasmid 1 | 6XHN-PX12-20v5-hGHF(SEQ ID NO: 35) |
| GH-PX12-20v6-N | SEQ ID NO: 36 | — | Plasmid 1 | 6XHN-PX12-20v6-hGHF(SEQ ID NO: 37) |
| GH-PX12-20v7-N | SEQ ID NO: 38 | — | Plasmid 1 | 6XHN-PX12-20v7-hGHF(SEQ ID NO: 39) |
| GH-PX12-20v8-N | SEQ ID NO: 40 | — | Plasmid 1 | 6XHN-PX12-20v8-hGHF(SEQ ID NO: 41) |
| GH-PX12-20v9-N | SEQ ID NO: 42 | — | Plasmid 1 | 6XHN-PX12-20v9-hGHF(SEQ ID NO: 43) |
| GH-PX12-29-N | SEQ ID NO: 44 | — | Plasmid 1 | 6XHN-PX12-29-hGHF(SEQ ID NO: 45) |
| GH-PX12-32-N | SEQ ID NO: 46 | — | Plasmid 1 | 6XHN-PX12-32-hGHF(SEQ ID NO: 47) |
| GH-PX12-33-N | SEQ ID NO: 48 | — | Plasmid 1 | 6XHN-PX12-33-hGHF(SEQ ID NO: 49) |
| GH-PX12-36-N | SEQ ID NO: 50 | — | Plasmid 1 | 6XHN-PX12-36-hGHF(SEQ ID NO: 51) |
| GH-PX12-38-N | SEQ ID NO: 52 | — | Plasmid 1 | 6XHN-PX12-38-hGHF(SEQ ID NO: 53) |

TABLE 2-continued

Template plasmids and primers used in PCR amplification of hGH gene or IFN beta gene added with a peptide tag coding sequence

| | | | | |
|---|---|---|---|---|
| GH-PX12-28-N | SEQ ID NO: 54 | — | Plasmid 1 | 6XHN-PX12-28-hGHF(SEQ ID NO: 55) |
| GH-PX12-39-N | SEQ ID NO: 56 | — | Plasmid 1 | 6XHN-PX12-39-hGHF(SEQ ID NO: 57) |
| GH-PX17-20-N | SEQ ID NO: 58 | — | Plasmid 1 | 6XHN-PX17-20-hGHF(SEQ ID NO: 59) |
| GH-PX17-20v2-N | SEQ ID NO: 60 | — | Plasmid 1 | 6XHN-PX17-20v2-hGHF(SEQ ID NO: 61) |
| GH-PX12-20Xa-N | SEQ ID NO: 62 | — | Plasmid 1 | 6XHN-PX12-20Xa-hGHF(SEQ ID NO: 63) |
| GH-PK11v1-N | SEQ ID NO: 64 | — | Plasmid 1 | 6XHN-PK11v1-hGHF(SEQ ID NO: 65) |
| GH-PK11v2-N | SEQ ID NO: 66 | — | Plasmid 1 | 6XHN-PK11v2-hGHF(SEQ ID NO: 67) |
| IFN-(−) | — | — | Plasmid 2 | 6XHN-IFNBF(SEQ ID NO: 68) |
| IFN-PG12-N | SEQ ID NO: 22 | — | Plasmid 2 | 6XHN-PG12-IFNBF(SEQ ID NO: 70) |
| IFN-PG12-C | — | SEQ ID NO: 22 | Plasmid 2 | 6XHN-IFNBF(SEQ ID NO: 68) |
| IFN-PG12-NC | SEQ ID NO: 22 | SEQ ID NO: 22 | Plasmid 2 | 6XHN-PG12-IFNBF(SEQ ID NO: 70) |
| IFN-PX12-20-N | SEQ ID NO: 25 | — | Plasmid 2 | 6XHN-PX12-20-IFNBF(SEQ ID NO: 72) |
| IFN-PX12-20-C | — | SEQ ID NO: 25 | Plasmid 2 | 6XHN-INFBF(SEQ ID NO: 68) |
| IFN-PX12-20-NC | SEQ ID NO: 25 | SEQ ID NO: 25 | Plasmid 2 | 6XHN-PX12-20-IFNBF(SEQ ID NO: 72) |
| GH-PX12-20v7-NC | SEQ ID NO: 38 | SEQ ID NO: 38 | Plasmid 1 | 6XHN-PX12-20v7-hGHF(SEQ ID NO: 39) |
| GH-PX12-40-N | SEQ ID NO: 92 | — | Plasmid 1 | 6XHN-PX1240-hGHF(SEQ ID NO: 93) |
| GH-PX12-41-N | SEQ ID NO: 94 | — | Plasmid 1 | 6XHN-PX1241-hGHF(SEQ ID NO: 95) |
| GH-PX12-43-N | SEQ ID NO: 96 | — | Plasmid 1 | 6XHN-PX1243-hGHF(SEQ ID NO: 97) |
| GH-PX12-44-N | SEQ ID NO: 98 | — | Plasmid 1 | 6XHN-PX1244-hGHF(SEQ ID NO: 99) |
| GH-PX17-20v7-N | SEQ ID NO: 100 | — | Plasmid 1 | 6XHN-PX17-20v7-hGHF(SEQ ID NO: 101) |
| GH-PX17-20v8-N | SEQ ID NO: 102 | — | Plasmid 1 | 6XHN-PX17-20v8-hGHF(SEQ ID NO: 103) |
| GH-PX13-01-N | SEQ ID NO: 104 | — | Plasmid 1 | 6XHN-PX13-01-hGHF(SEQ ID NO: 105) |
| GH-PX12-45-N | SEQ ID NO: 106 | — | Plasmid 1 | 6XHN-PX1245-hGHF(SEQ ID NO: 107) |
| GH-PX22-20v7-N | SEQ ID NO: 108 | — | Plasmid 1 | 6XHN-PX22-20v7-hGHF(SEQ ID NO: 109) |
| GH-PX32-20v7-N | SEQ ID NO: 110 | — | Plasmid 1 | 6XHN-PX32-20v7-hGHF(SEQ ID NO: 111) |
| GH-PX12-20v9-N | SEQ ID NO: 112 | — | Plasmid 1 | 6XHN-PX12-20v9-hGHF(SEQ ID NO: 113) |
| GH-PX12-20v10-N | SEQ ID NO: 114 | — | Plasmid 1 | 6XHN-PX12-20v10-hGHF(SEQ ID NO: 115) |
| GH-PX12-20v12-N | SEQ ID NO: 116 | — | Plasmid 1 | 6XHN-PX12-20v12-hGHF(SEQ ID NO: 117) |
| GH-PX12-20v13-N | SEQ ID NO: 118 | — | Plasmid 1 | 6XHN-PX12-20v13-hGHF(SEQ ID NO: 119) |
| GH-PK10v2-N | SEQ ID NO: 120 | — | Plasmid 1 | 6XHN-PK10v2-hGHF(SEQ ID NO: 121) |
| GH-PK09v2-N | SEQ ID NO: 122 | — | Plasmid 1 | 6XHN-PK09v2-hGHF(SEQ ID NO: 123) |
| GH-PK10v3-N | SEQ ID NO: 124 | — | Plasmid 1 | 6XHN-PK10v3-hGHF(SEQ ID NO: 125) |
| GH-PK08v3-N | SEQ ID NO: 126 | — | Plasmid 1 | 6XHN-PK08v3-hGHF(SEQ ID NO: 127) |
| GH-PK09v3-N | SEQ ID NO: 128 | — | Plasmid 1 | 6XHN-PK09v3-hGHF(SEQ ID NO: 129) |
| GH-PK09v4-N | SEQ ID NO: 130 | — | Plasmid 1 | 6XHN-PK09v4-hGHF(SEQ ID NO: 131) |

TABLE 2-continued

Template plasmids and primers used in PCR amplification of hGH gene or IFN beta gene added with a peptide tag coding sequence

| | | | |
|---|---|---|---|
| GH-PX12-49-N | SEQ ID NO: 132 — | Plasmid 1 | 6XHN-PX1249-hGHF(SEQ ID NO: 133) |
| GH-PX12-51-N | SEQ ID NO: 134 — | Plasmid 1 | 6XHN-PX12-51-hGHF(SEQ ID NO: 135) |
| GH-PX12-52-N | SEQ ID NO: 136 — | Plasmid 1 | 6XHN-PX12-52-hGHF(SEQ ID NO: 137) |
| GH-PX12-54-N | SEQ ID NO: 138 — | Plasmid 1 | 6XHN-PX12-54-hGHF(SEQ ID NO: 139) |
| GH-PX12-61-N | SEQ ID NO: 140 — | Plasmid 1 | 6XHN-PX12-61-hGHF(SEQ ID NO: 141) |
| GH-PX12-62-N | SEQ ID NO: 142 — | Plasmid 1 | 6XHN-PX12-62-hGHF(SEQ ID NO: 79) |
| GH-PX12-40v2-N | SEQ ID NO: 143 — | Plasmid 1 | 6XHN-PX1240v2-hGHF(SEQ ID NO: 144) |
| GH-PX12-41v2-N | SEQ ID NO: 145 — | Plasmid 1 | 6XHN-PX12-41v2-hGHF(SEQ ID NO: 146) |
| GH-PX12-45v2-N | SEQ ID NO: 147 — | Plasmid 1 | 6XHN-PX12-45v2-hGHF(SEQ ID NO: 148) |
| GH-PX12-45v3-N | SEQ ID NO: 149 — | Plasmid 1 | 6XHN-PX12-45v3-hGHF(SEQ ID NO: 150) |
| GH-PX12-75-N | SEQ ID NO: 151 — | Plasmid 1 | 6XHN-PX12-75-hGHF(SEQ ID NO: 152) |
| GH-PX12-76-N | SEQ ID NO: 153 — | Plasmid 1 | 6XHN-PX12-76-hGHF(SEQ ID NO: 154) |
| GH-PX12-77-N | SEQ ID NO: 155 — | Plasmid 1 | 6XHN-PX12-77-hGHF(SEQ ID NO: 156) |
| GH-PX12-78-N | SEQ ID NO: 157 — | Plasmid 1 | 6XHN-PX12-78-hGHF(SEQ ID NO: 158) |
| | | PCR amplification fragment | Reverse Primer |
| | | GH-(-) | hGHR-stopCYCt(SEQ ID NO: 9) |
| | | GH-RS-N | hGHR-stopCYCt(SEQ ID NO: 9) |
| | | GH-ECM29SC-N | hGHR-stopCYCt(SEQ ID NO: 9) |
| | | GH-ECM29ON-N | hGHR-stopCYCt(SEQ ID NO: 9) |
| | | GH-Anjam-N | hGHR-stopCYCt(SEQ ID NO: 9) |
| | | GH-PG12v5-N | hGHR-stopCYCt(SEQ ID NO: 9) |
| | | GH-PG12v7-N | hGHR-stopCYCt(SEQ ID NO: 9) |
| | | GH-PG12-N | hGHR-stopCYCt(SEQ ID NO: 9) |
| | | GH-PG12-C | hGHR-PG12-stopCYCt(SEQ ID NO: 24) |
| | | GH-PG12-NC | hGHR-PG12-stopCYCt(SEQ ID NO: 24) |
| | | GH-PX12-20-N | hGHR-stopCYCt(SEQ ID NO: 9) |
| | | GH-PX12-20-C | hGHR-PX12-20-stopCYCt(SEQ ID NO: 27) |
| | | GH-PX12-20-NC | hGHR-PX12-20-stopCYCt(SEQ ID NO: 27) |
| | | GH-PX12-20v2-N | hGHR-stopCYCt(SEQ ID NO: 9) |
| | | GH-PX12-20v3-N | hGHR-stopCYCt(SEQ ID NO: 9) |
| | | GH-PX12-20v4-N | hGHR-stopCYCt(SEQ ID NO: 9) |
| | | GH-PX12-20v5-N | hGHR-stopCYCt(SEQ ID NO: 9) |
| | | GH-PX12-20v6-N | hGHR-stopCYCt(SEQ ID NO: 9) |
| | | GH-PX12-20v7-N | hGHR-stopCYCt(SEQ ID NO: 9) |
| | | GH-PX12-20v8-N | hGHR-stopCYCt(SEQ ID NO: 9) |

TABLE 2-continued

Template plasmids and primers used in PCR amplification of hGH gene or IFN beta gene added with a peptide tag coding sequence

| | | |
|---|---|---|
| | GH-PX12-20v9-N | hGHR-stopCYCt(SEQ ID NO: 9) |
| | GH-PX12-29-N | hGHR-stopCYCt(SEQ ID NO: 9) |
| | GH-PX12-32-N | hGHR-stopCYCt(SEQ ID NO: 9) |
| | GH-PX12-33-N | hGHR-stopCYCt(SEQ ID NO: 9) |
| | GH-PX12-36-N | hGHR-stopCYCt(SEQ ID NO: 9) |
| | GH-PX12-38-N | hGHR-stopCYCt(SEQ ID NO: 9) |
| | GH-PX12-28-N | hGHR-stopCYCt(SEQ ID NO: 9) |
| | GH-PX12-39-N | hGHR-stopCYCt(SEQ ID NO: 9) |
| | GH-PX17-20-N | hGHR-stopCYCt(SEQ ID NO: 9) |
| | GH-PX17-20v2-N | hGHR-stopCYCt(SEQ ID NO: 9) |
| | GH-PX12-20Xa-N | hGHR-stopCYCt(SEQ ID NO: 9) |
| | GH-PK11v1-N | hGHR-stopCYCt(SEQ ID NO: 9) |
| | GH-PK11v2-N | hGHR-stopCYCt(SEQ ID NO: 9) |
| | IFN-(-) | IFNBR-stopCYCt(SEQ ID NO: 69) |
| | IFN-PG12-N | IFNBR-stopCYCt(SEQ ID NO: 69) |
| | IFN-PG12-C | IFNBR-PG12-stopCYCt(SEQ ID NO: 71) |
| | IFN-PG12-NC | IFNBR-PG12-stopCYCt(SEQ ID NO: 71) |
| | IFN-PX12-20-N | IFNBR-stopCYCt(SEQ ID NO: 69) |
| | IFN-PX12-20-C | IFNBR-PX12-20-stopCYCt(SEQ ID NO: 73) |
| | IFN-PX12-20-NC | IFNBR-PX12-20-stopCYCt(SEQ ID NO: 73) |
| | GH-PX12-20v7-NC | hGHR-PX12-20v7-stopCYCt(SEQ ID NO: 91) |
| | GH-PX12-40-N | hGHR-stopCYCt(SEQ ID NO: 9) |
| | GH-PX12-41-N | hGHR-stopCYCt(SEQ ID NO: 9) |
| | GH-PX12-43-N | hGHR-stopCYCt(SEQ ID NO: 9) |
| | GH-PX12-44-N | hGHR-stopCYCt(SEQ ID NO: 9) |
| | GH-PX17-20v7-N | hGHR-stopCYCt(SEQ ID NO: 9) |
| | GH-PX17-20v8-N | hGHR-stopCYCt(SEQ ID NO: 9) |
| | GH-PX13-01-N | hGHR-stopCYCt(SEQ ID NO: 9) |
| | GH-PX12-45-N | hGHR-stopCYCt(SEQ ID NO: 9) |
| | GH-PX22-20v7-N | hGHR-stopCYCt(SEQ ID NO: 9) |
| | GH-PX32-20v7-N | hGHR-stopCYCt(SEQ ID NO: 9) |
| | GH-PX12-20v9-N | hGHR-stopCYCt(SEQ ID NO: 9) |
| | GH-PX12-20v10-N | hGHR-stopCYCt(SEQ ID NO: 9) |
| | GH-PX12-20v12-N | hGHR-stopCYCt(SEQ ID NO: 9) |
| | GH-PX12-20v13-N | hGHR-stopCYCt(SEQ ID NO: 9) |
| | GH-PK10v2-N | hGHR-stopCYCt(SEQ ID NO: 9) |
| | GH-PK09v2-N | hGHR-stopCYCt(SEQ ID NO: 9) |
| | GH-PK10v3-N | hGHR-stopCYCt(SEQ ID NO: 9) |

TABLE 2-continued

Template plasmids and primers used in PCR amplification of hGH gene or IFN beta gene added with a peptide tag coding sequence

| | | |
|---|---|---|
| | GH-PK08v3-N | hGHR-stopCYCt(SEQ ID NO: 9) |
| | GH-PK09v3-N | hGHR-stopCYCt(SEQ ID NO: 9) |
| | GH-PK09v4-N | hGHR-stopCYCt(SEQ ID NO: 9) |
| | GH-PX12-49-N | hGHR-stopCYCt(SEQ ID NO: 9) |
| | GH-PX12-51-N | hGHR-stopCYCt(SEQ ID NO: 9) |
| | GH-PX12-52-N | hGHR-stopCYCt(SEQ ID NO: 9) |
| | GH-PX12-54-N | hGHR-stopCYCt(SEQ ID NO: 9) |
| | GH-PX12-61-N | hGHR-stopCYCt(SEQ ID NO: 9) |
| | GH-PX12-62-N | hGHR-stopCYCt(SEQ ID NO: 9) |
| | GH-PX12-40v2-N | hGHR-stopCYCt(SEQ ID NO: 9) |
| | GH-PX12-41v2-N | hGHR-stopCYCt(SEQ ID NO: 9) |
| | GH-PX12-45v2-N | hGHR-stopCYCt(SEQ ID NO: 9) |
| | GH-PX12-45v3-N | hGHR-stopCYCt(SEQ ID NO: 9) |
| | GH-PX12-75-N | hGHR-stopCYCt(SEQ ID NO: 9) |
| | GH-PX12-76-N | hGHR-stopCYCt(SEQ ID NO: 9) |
| | GH-PX12-77-N | hGHR-stopCYCt(SEQ ID NO: 9) |
| | GH-PX12-78-N | hGHR-stopCYCt(SEQ ID NO: 9) |

TABLE 3

Template plasmids and primers used in PCR amplification of hGH gene or IFN beta gene added with a peptide tag coding sequence

| PCR amplification fragment | Added peptide tag sequence N-terminus | C-terminus | Template Plasmid | Forward Primer |
|---|---|---|---|---|
| E. coli GH-(−) | — | — | Plasmid 1 | 6XHN-hGHF(SEQ ID NO: 8) |
| E. coli GH-PX12-20-N | SEQ ID NO: 25 | — | Plasmid 1 | 6XHN-PX12-20-hGHF (SEQ ID NO: 26) |
| E. coli GH-PX12-20-NC | SEQ ID NO: 25 | SEQ ID NO: 25 | Plasmid 1 | 6XHN-PX12-20-hGHF (SEQ ID NO: 26) |
| E. coli IFN-(−) | — | — | Plasmid 2 | 6XHN-IFNBF(SEQ ID NO: 68) |
| E. coli IFN-PX12-20-N | SEQ ID NO: 25 | — | Plasmid 2 | 6XHN-PX12-20-IFNBF (SEQ ID NO: 72) |
| E. coli IFN-PX12-20-NC | SEQ ID NO: 25 | SEQ ID NO: 25 | Plasmid 2 | 6XHN-PX12-20-IFNBF (SEQ ID NO: 72) |
| E. coli IFN-PX12-20v7-N | SEQ ID NO: 38 | — | Plasmid 2 | 6XHN-PX12-20v7-IFNBF (SEQ ID NO: 39) |
| E. coli IFN-PX12-20v7-NC | SEQ ID NO: 38 | SEQ ID NO: 38 | Plasmid 2 | 6XHN-PX12-20v7-IFNBF (SEQ ID NO: 39) |
| Brevibacterium GH-(−) | — | — | Plasmid 1 | P22SP-hGHF(SEQ ID NO: 81) |
| Brevibacterium GH-PX12-20-N | SEQ ID NO: 25 | — | Plasmid 1 | P22SP-PX12-20-hGHF (SEQ ID NO: 83) |
| Brevibacterium GH-PX12-20-NC | SEQ ID NO: 25 | SEQ ID NO: 25 | Plasmid 1 | P22SP-PX12-20-hGHF (SEQ ID NO: 83) |

TABLE 3-continued

Template plasmids and primers used in PCR amplification of hGH gene or IFN beta gene added with a peptide tag coding sequence

| | | | | |
|---|---|---|---|---|
| Brevibacterium GH-PX12-38-NC | SEQ ID NO: 52 | SEQ ID NO: 52 | Plasmid 1 | P22SP-PX12-38-hGHF (SEQ ID NO: 85) |
| Brevibacterium GH-PX12-20v7-NC | SEQ ID NO: 38 | SEQ ID NO: 38 | Plasmid 1 | P22SP-PX12-20v7-hGHF (SEQ ID NO: 87) |
| Brevibacterium XynA-(-) | — | — | Plasmid 5 | mCWSP-AD-BsxynAF (SEQ ID NO: 164) |
| Brevibacterium XynA-PX12-20-N | SEQ ID NO: 25 | — | Plasmid 5 | mCWSP-AD-PX12-20-BsxynAF (SEQ ID NO: 166) |
| Brevibacterium XynA-PX12-20-C | — | SEQ ID NO: 25 | Plasmid 5 | mCWSP-AD-BsxynAF (SEQ ID NO: 164) |
| Brevibacterium XynA-PX12-20-NC | SEQ ID NO: 25 | SEQ ID NO: 25 | Plasmid 5 | mCWSP-AD-PX12-20-BsxynAF (SEQ ID NO: 166) |
| Brevibacterium EstA-(-) | — | — | Plasmid 6 | mCWSP-AD-BsestAF (SEQ ID NO: 182) |
| Brevibacterium EstA-PX12-20-N | SEQ ID NO: 25 | — | Plasmid 6 | mCWSP-AD-PX12-20-BsestAF (SEQ ID NO: 184) |
| Pichia GH-(-) | — | — | Plasmid 1 | AFSP-hGH (SEQ ID NO: 170) |
| Pichia GH-PX12-20-N | SEQ ID NO: 25 | — | Plasmid 1 | AFSP-PX12-20-hGH (SEQ ID NO: 172) |
| Pichia GH-PX12-20-C | — | SEQ ID NO: 25 | Plasmid 1 | AFSP-hGH (SEQ ID NO: 170) |
| Pichia GH-PX12-20-NC | SEQ ID NO: 25 | SEQ ID NO: 25 | Plasmid 1 | AFSP-PX12-20-hGH (SEQ ID NO: 172) |
| Pichia GH-PX12-20v7-N | SEQ ID NO: 38 | — | Plasmid 1 | AFSP-PX12-20v7-hGH (SEQ ID NO: 174) |

| PCR amplification fragment | Reverse Primer |
|---|---|
| E. coli GH-(-) | hGHR-stopT7t (SEQ ID NO: 74) |
| E. coli GH-PX12-20-N | hGHR-stopT7t (SEQ ID NO: 74) |
| E. coli GH-PX12-20-NC | hGHR-PX12-20-stopT7t (SEQ ID NO: 75) |
| E. coli IFN-(-) | IFNBR-stopT7t (SEQ ID NO: 76) |
| E. coli IFN-PX12-20-N | IFNBR-stopT7t (SEQ ID NO: 76) |
| E. coli IFN-PX12-20-NC | IFNBR-PX12-20-stopT7t (SEQ ID NO: 77) |
| E. coli IFN-PX12-20v7-N | IFNBR-stopT7t (SEQ ID NO: 76) |
| E. coli IFN-PX12-20v7-NC | IFNBR-PX12-20v7-stopT7t (SEQ ID NO: 80) |
| Brevibacterium GH-(-) | hGHR-stopBrevit (SEQ ID NO: 82) |
| Brevibacterium GH-PX12-20-N | hGHR-stopBrevit (SEQ ID NO: 82) |
| Brevibacterium GH-PX12-20-NC | hGHR-PX12-20-stopBrevit (SEQ ID NO: 84) |
| Brevibacterium GH-PX12-38-NC | hGHR-PX12-38-stopBrevit (SEQ ID NO: 86) |
| Brevibacterium GH-PX12-20v7-NC | hGHR-PX12-20v7-stopBrevit (SEQ ID NO: 88) |
| Brevibacterium XynA-(-) | BsxynAR-HA (SEQ ID NO: 165) |
| Brevibacterium XynA-PX12-20-N | BsxynAR-HA (SEQ ID NO: 165) |

TABLE 3-continued

Template plasmids and primers used in PCR amplification of hGH gene or IFN beta gene added with a peptide tag coding sequence

| | | |
|---|---|---|
| | *Brevibacterium* XynA-PX12-20-C | BsxynAR-PX12-20-HA(SEQ ID NO: 167) |
| | *Brevibacterium*XynA-PX12-20-NC | BsxynAR-PX12-20-HA(SEQ ID NO: 167) |
| | *Brevibacterium*EstA-(-) | BsestAR-HA(SEQ ID NO: 183) |
| | *Brevibacterium*EstA-PX12-20-N | BsestAR-HA(SEQ ID NO: 183) |
| | Pichia GH-(-) | hGHR-stopAOXt(SEQ ID NO: 171) |
| | Pichia GH-PX12-20-N | hGHR-stopAOXt(SEQ ID NO: 171) |
| | Pichia GH-PX12-20-C | hGHextR-PX12-20-stopAOXt (SEQ ID NO: 173) |
| | Pichia GH-PX12-20-NC | hGHextR-PX12-20-stopAOXt (SEQ ID NO: 173) |
| | Pichia GH-PX12-20v7-N | hGHR-stopAOXt(SEQ ID NO: 171) |

(5) Improvement of Protein Expression in Insect Cells and Mammalian Cells by Addition of Various Peptide Tags The prepared recombinant insect cells or mammalian cells were cultured under predetermined conditions, and fluorescence of GFP was measured under predetermined conditions.

Figure 15:
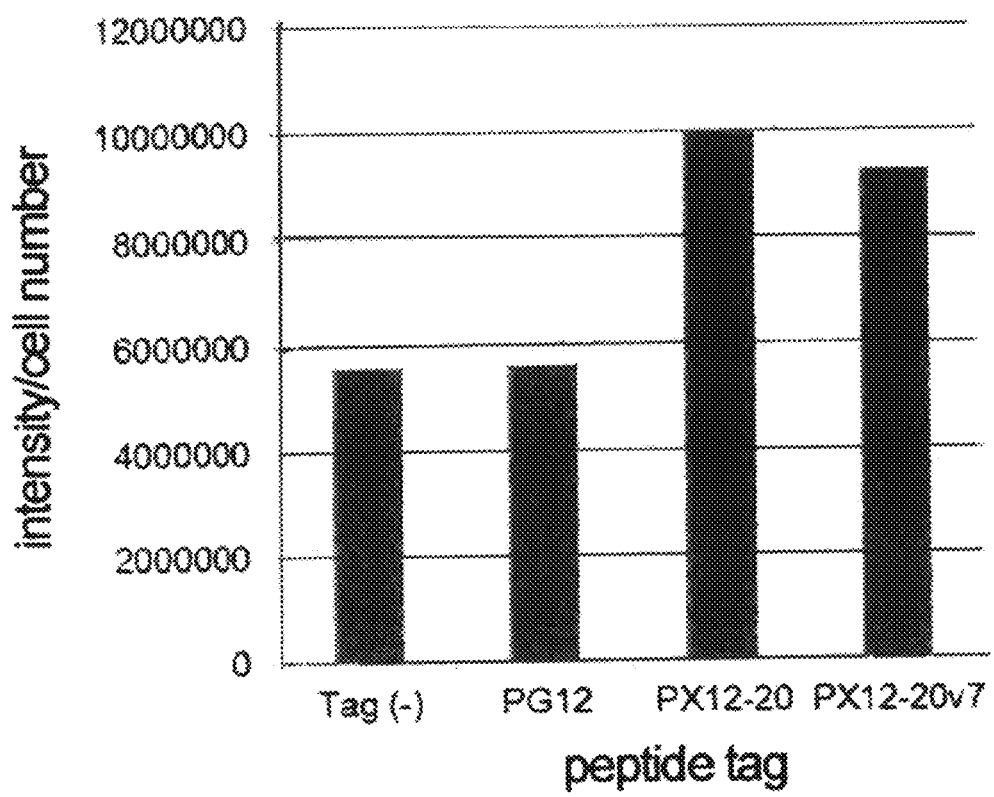
FIG. 15 is a diagram showing the expression levels of GFP having various tags in insect cells. Relative values with respect to the expression level of non-tagged GFP, which is taken as 1, are shown.

As a result, as shown in FIG. 15, when GFPs having various peptide tags were expressed in insect cells, the proteins having the PX12-20 tag or the PX12-20v7 tag showed higher expression levels than the non-tagged protein.

Figure 16:
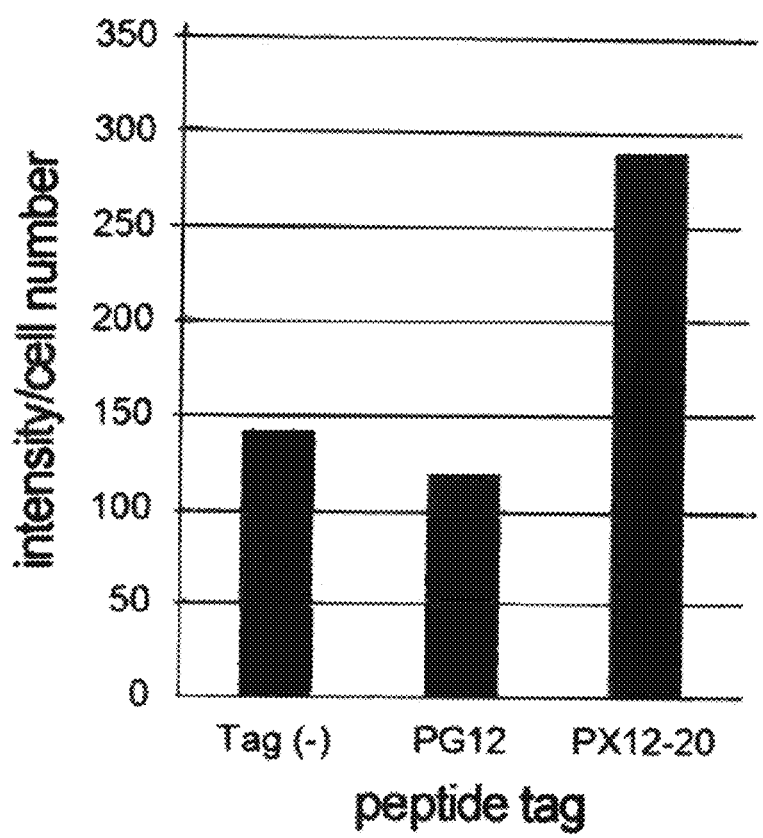
FIG. 16 is a diagram showing the expression levels of GFP having various tags in mammalian cells. Relative values with respect to the expression level of non-tagged GFP, which is taken as 1, are shown.

As a result, as shown in FIG. 16, when GFPs having various peptide tags were expressed in mammalian cells, the protein having the PX12-20 tag showed a higher expression level than the non-tagged protein.

INDUSTRIAL APPLICABILITY

The peptide tag of the present invention is useful in the fields of genetic engineering, protein engineering, and the like, and proteins having the peptide tag of the present invention are useful in the fields of medicine, research, food, animal husbandry, and the like.

The invention claimed is:

1. A peptide comprising the amino acid sequence of SEQ ID NO: 25, 28, 30, 32, 34, 36, 38, 40, 42, 44, 46, 48, 50, 54, 64, 66, 102, 104, 106, 112, 114, 116, 118, 122, 124, 132, 136, 140, 142, 147, 149, 151, 153, or 157.

2. A tagged protein comprising:
the peptide according to claim 1 and
a protein.

3. The tagged protein according to claim 2,
wherein the protein is selected from the group consisting of human growth hormone, interferon β, xylanase, esterase, and green fluorescent protein (GFP).

4. The tagged protein according to claim 2, wherein the peptide is linked to the protein through a protease recognition sequence.

5. The tagged protein according to claim 2, further comprising:
a secretion signal.

6. A DNA encoding the tagged protein according to claim 2.

7. A recombinant vector comprising:
the DNA according to claim 6.

8. A transformant prepared by transformation with the DNA according to claim 6.

9. The transformant according to claim 8,
wherein the transformant is yeast, E. coli, Brevibacillus, an insect cell, or a mammalian cell, and
wherein the mammalian cell comprises a human cultured cell, but does not comprise a human individual.

10. A method for producing a tagged protein, comprising:
culturing the transformant according to claim 8 to allow accumulation of the tagged protein, and
collecting the tagged protein.

11. A transformant prepared by transformation with the recombinant vector according to claim 7.

12. A peptide consisting of the amino acid sequence of SEQ ID NO: 52, 58, 60, 92, 94, 96, 100, 108, 110, 120, 128, 130, 134, 145, or 155.

13. The peptide of claim 12, wherein peptide consists of the amino acid sequence of SEQ ID NO: 52, 58, 60, 92, 94, 96, 100, 108, 110, 120, 130, 134, 145, or 155.

* * * * *